United States Patent
Sun et al.

(10) Patent No.: US 12,227,567 B2
(45) Date of Patent: Feb. 18, 2025

(54) TREATING CANCER BY BLOCKING THE INTERACTION OF TIM-3 AND ITS LIGAND

(71) Applicant: TRUEBINDING, INC, Foster City, CA (US)

(72) Inventors: Dongxu Sun, Los Altos, CA (US); Yan Wang, Concord, CA (US)

(73) Assignee: TrueBinding, Inc., Menlo Park, CA (US)

( * ) Notice: Subject to any disclaimer, the term of this patent is extended or adjusted under 35 U.S.C. 154(b) by 40 days.

(21) Appl. No.: 16/633,530

(22) PCT Filed: Jul. 24, 2018

(86) PCT No.: PCT/US2018/043513
§ 371 (c)(1),
(2) Date: Jan. 23, 2020

(87) PCT Pub. No.: WO2019/023247
PCT Pub. Date: Jan. 31, 2019

(65) Prior Publication Data
US 2020/0223921 A1    Jul. 16, 2020

Related U.S. Application Data

(60) Provisional application No. 62/536,886, filed on Jul. 25, 2017.

(51) Int. Cl.
| | |
|---|---|
| *A61K 39/00* | (2006.01) |
| *A61K 9/00* | (2006.01) |
| *A61K 39/395* | (2006.01) |
| *A61P 35/04* | (2006.01) |
| *C07K 16/28* | (2006.01) |
| *G01N 33/574* | (2006.01) |

(52) U.S. Cl.
CPC ........ *C07K 16/2803* (2013.01); *A61K 9/0019* (2013.01); *A61P 35/04* (2018.01); *G01N 33/57492* (2013.01); *A61K 2039/505* (2013.01); *C07K 2317/21* (2013.01); *C07K 2317/30* (2013.01); *C07K 2317/55* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,301,144 A | 11/1981 | Iwashita et al. |
| 4,495,285 A | 1/1985 | Shimizu et al. |
| 4,496,689 A | 1/1985 | Mitra |
| 4,609,546 A | 9/1986 | Hiratani |
| 4,640,835 A | 2/1987 | Shimizu et al. |
| 4,670,417 A | 6/1987 | Iwasaki et al. |
| 4,766,106 A | 8/1988 | Katre et al. |
| 4,791,192 A | 12/1988 | Nakagawa et al. |
| 5,208,020 A | 5/1993 | Chari et al. |
| 5,229,275 A | 7/1993 | Goroff |
| 5,270,202 A | 12/1993 | Raychaudhuri |
| 5,405,783 A | 4/1995 | Pirrung et al. |
| 5,412,087 A | 5/1995 | McGall et al. |
| 5,416,064 A | 5/1995 | Chari et al. |
| 5,445,934 A | 8/1995 | Fodor et al. |
| 5,567,610 A | 10/1996 | Borrebaeck et al. |
| 5,624,659 A | 4/1997 | Bigner et al. |
| 5,695,937 A | 12/1997 | Kinzler et al. |
| 5,928,885 A | 7/1999 | Nixon et al. |
| 5,936,078 A | 8/1999 | Kuga et al. |
| 5,948,626 A | 9/1999 | Hawkins et al. |
| 5,968,797 A | 10/1999 | Ni et al. |
| 5,969,108 A | 10/1999 | McCafferty et al. |
| 5,985,660 A | 11/1999 | Galy |
| 6,087,153 A | 7/2000 | Greenwald et al. |
| 6,150,584 A | 11/2000 | Kucherlapati et al. |
| 6,156,311 A | 12/2000 | Strickland et al. |
| 6,162,963 A | 12/2000 | Kucherlapati et al. |
| 6,174,708 B1 | 1/2001 | Sodoyer et al. |
| 6,187,287 B1 | 2/2001 | Leung et al. |
| 6,242,421 B1 | 6/2001 | Bowen et al. |
| 6,255,054 B1 | 7/2001 | Hugon et al. |
| 6,303,576 B1 | 10/2001 | Blaschuk et al. |
| 6,562,806 B1 | 5/2003 | Thurston et al. |
| 6,576,607 B1 | 6/2003 | Schachner |

(Continued)

FOREIGN PATENT DOCUMENTS

| | | |
|---|---|---|
| EP | 0 329 400 | 8/1989 |
| EP | 0 404 097 | 12/1990 |

(Continued)

OTHER PUBLICATIONS

US 10,308,710 B2, 06/2019, Grueninger et al. (withdrawn)

(Continued)

*Primary Examiner* — Maher M Haddad
(74) *Attorney, Agent, or Firm* — KNOBBE, MARTENS, OLSON & BEAR LLP

(57) ABSTRACT

Provided herein are methods of activating immune response and/or treating cancer in a patient comprising administering to the patient a Gal3:TIM-3 inhibitor that interferes with the interaction between Gal3 and TIM-3, where said inhibitor is administered in an amount sufficient to activate immune response. Also provided are a humanized anti-Gal3 antibodies that can block the interaction between Gal3 and TIM3 and methods of using the anti-Gal3 antibody to treat cancer. Methods for determining if a patient's cancer is suitable for treatment with a Gal3:TIM-3 inhibitor and methods for selecting compounds that can block interaction between Gal3 and TIM-3, activating immune response and/or treating cancer are also provided.

15 Claims, 18 Drawing Sheets

Specification includes a Sequence Listing.

(56) References Cited

U.S. PATENT DOCUMENTS

| | | |
|---|---|---|
| 6,608,192 B1 | 8/2003 | Thurston et al. |
| 6,677,116 B1 | 1/2004 | Blaschuk et al. |
| 6,716,821 B2 | 4/2004 | Zhao et al. |
| 6,727,075 B2 | 4/2004 | Fitzgerald et al. |
| 6,821,783 B1 | 11/2004 | Comely et al. |
| 6,825,164 B1 | 11/2004 | Stern et al. |
| 6,852,482 B1 | 2/2005 | Chrysler et al. |
| 6,884,869 B2 | 4/2005 | Senter et al. |
| 6,982,089 B2 | 1/2006 | Tobinick et al. |
| 7,014,855 B2 | 3/2006 | Schenk |
| 7,029,860 B2 | 4/2006 | Ota et al. |
| 7,049,311 B1 | 5/2006 | Thurston et al. |
| 7,067,511 B2 | 6/2006 | Thurston et al. |
| 7,115,260 B2 | 10/2006 | Dixit et al. |
| 7,186,681 B2 | 3/2007 | Liu et al. |
| 7,214,715 B2 | 5/2007 | Beck et al. |
| 7,244,724 B2 | 7/2007 | Liu et al. |
| 7,270,818 B2 | 9/2007 | Averback |
| 7,276,497 B2 | 10/2007 | Chari et al. |
| 7,409,040 B2 | 8/2008 | Cyrulnik |
| 7,416,855 B2 | 8/2008 | He et al. |
| 7,485,712 B2 | 2/2009 | Mandelkow et al. |
| 7,498,298 B2 | 3/2009 | Doronina et al. |
| 7,528,126 B2 | 5/2009 | Howard et al. |
| 7,582,732 B2 | 9/2009 | Horie et al. |
| 7,611,910 B2 | 11/2009 | Balin et al. |
| 7,612,062 B2 | 11/2009 | Gregson et al. |
| 7,659,241 B2 | 2/2010 | Senter et al. |
| 7,662,816 B2 | 2/2010 | Cumming et al. |
| 7,700,823 B2 | 4/2010 | Casas et al. |
| 7,704,924 B2 | 4/2010 | Thurston et al. |
| 7,732,568 B2 | 6/2010 | Mattner |
| 7,750,116 B1 | 7/2010 | Doronina et al. |
| 7,846,679 B2 | 12/2010 | St. George-Hyslop et al. |
| 7,858,642 B2 | 12/2010 | John et al. |
| 7,910,590 B2 | 3/2011 | Huang et al. |
| 7,935,252 B2 | 5/2011 | Mattner et al. |
| 7,935,348 B2 | 5/2011 | Mattner et al. |
| 7,951,373 B2 | 5/2011 | Schachner |
| 7,955,812 B2 | 6/2011 | Moir et al. |
| 7,964,566 B2 | 6/2011 | Doronina et al. |
| 7,989,597 B2 | 8/2011 | Chang et al. |
| 8,008,449 B2 | 8/2011 | Korman et al. |
| 8,022,180 B2 | 9/2011 | Mattner et al. |
| 8,034,353 B2 | 10/2011 | Yano et al. |
| 8,060,179 B1 | 11/2011 | Flynn |
| 8,105,597 B2 | 1/2012 | Davies et al. |
| 8,105,839 B2 | 1/2012 | Urakami et al. |
| 8,163,736 B2 | 4/2012 | Gauzy et al. |
| 8,168,188 B1 | 5/2012 | Hoshi et al. |
| 8,173,775 B2 | 5/2012 | Iwatsubo et al. |
| 8,192,954 B2 | 6/2012 | Klass et al. |
| 8,222,002 B2 | 7/2012 | Sugimura et al. |
| 8,232,373 B2 | 7/2012 | Wang |
| 8,257,740 B1 | 9/2012 | Sung et al. |
| 8,263,558 B2 | 9/2012 | Holzman et al. |
| 8,288,352 B2 | 10/2012 | Doronina et al. |
| 8,318,171 B2 | 11/2012 | Bush et al. |
| 8,318,687 B2 | 11/2012 | Tabira et al. |
| 8,323,925 B2 | 12/2012 | Chakravarthy |
| 8,338,379 B2 | 12/2012 | Yamaguchi et al. |
| 8,343,493 B2 | 1/2013 | VanMechelen et al. |
| 8,349,579 B2 | 1/2013 | Raz et al. |
| 8,357,781 B2 | 1/2013 | Johnson-Wooed et al. |
| 8,394,380 B2 | 3/2013 | Manucharyan et al. |
| 8,404,678 B2 | 3/2013 | Bouchard et al. |
| 8,409,575 B2 | 4/2013 | Lannfelt et al. |
| 8,426,402 B2 | 4/2013 | Li et al. |
| 8,481,701 B2 | 7/2013 | Jarrige et al. |
| 8,487,099 B2 | 7/2013 | Greenlee et al. |
| 8,501,934 B2 | 8/2013 | Howard et al. |
| 8,518,975 B2 | 8/2013 | Aslanian et al. |
| 8,613,920 B2 | 12/2013 | Lieberburg et al. |
| 8,617,549 B2 | 12/2013 | Sierks et al. |
| 8,618,123 B2 | 12/2013 | Sasikumar et al. |
| 8,623,365 B2 | 1/2014 | Davies et al. |
| 8,633,185 B2 | 1/2014 | Howard et al. |
| 8,642,044 B2 | 2/2014 | Schenk et al. |
| 8,663,650 B2 | 3/2014 | Nicolau et al. |
| 8,664,411 B2 | 3/2014 | Wu et al. |
| 8,672,857 B2 | 3/2014 | Muntendam |
| 8,697,688 B2 | 4/2014 | Howard et al. |
| 8,703,714 B2 | 4/2014 | Doronina et al. |
| 8,710,193 B2 | 4/2014 | Irie et al. |
| 8,722,042 B2 | 5/2014 | Relkin |
| 8,748,386 B2 | 6/2014 | Sigurdsson |
| 8,764,695 B2 | 7/2014 | Eliaz |
| 8,778,885 B2 | 7/2014 | Cashman et al. |
| 8,784,810 B2 | 7/2014 | Lieberburg et al. |
| 8,796,319 B2 | 8/2014 | Combs et al. |
| 8,802,667 B2 | 8/2014 | Li et al. |
| 8,809,010 B2 | 8/2014 | Hoffmann et al. |
| 8,809,320 B2 | 8/2014 | Li et al. |
| 8,852,874 B2 | 10/2014 | Olas et al. |
| 8,871,720 B2 | 10/2014 | Doronina et al. |
| 8,877,192 B2 | 11/2014 | Mjalli et al. |
| 8,877,207 B2 | 11/2014 | Cimini et al. |
| 8,912,145 B2 | 12/2014 | Terakawa et al. |
| 8,933,295 B2 | 1/2015 | Jung et al. |
| 8,936,910 B2 | 1/2015 | Mitsch et al. |
| 8,951,747 B2 | 2/2015 | Demotte et al. |
| 8,993,833 B2 | 3/2015 | Colton et al. |
| 9,034,334 B2 | 5/2015 | Gellerfors et al. |
| 9,066,928 B1 | 6/2015 | Estus et al. |
| 9,089,614 B2 | 7/2015 | Lin et al. |
| 9,133,267 B2 | 9/2015 | Lee et al. |
| 9,163,062 B2 | 10/2015 | Sarasa Barrio |
| 9,173,928 B2 | 11/2015 | Matsumoto |
| 9,217,036 B2 | 12/2015 | Strittmatter et al. |
| 9,234,038 B2 | 1/2016 | Jung et al. |
| 9,239,333 B2 | 1/2016 | Snider |
| 9,242,013 B2 | 1/2016 | Howard et al. |
| 9,295,707 B2 | 3/2016 | Shashoua |
| 9,320,436 B2 | 4/2016 | Russmann et al. |
| 9,347,085 B2 | 5/2016 | Gan et al. |
| 9,382,316 B2 | 7/2016 | Yoon |
| 9,580,494 B2 | 2/2017 | Shafer et al. |
| 9,618,511 B2 | 4/2017 | Querfurth |
| 9,637,552 B2 | 5/2017 | Cashman et al. |
| 9,645,155 B2 | 5/2017 | Cai et al. |
| 9,737,505 B2 | 8/2017 | Denis et al. |
| 9,751,912 B2 | 9/2017 | Hoshi |
| 9,757,398 B2 | 9/2017 | Vigo et al. |
| 9,777,056 B2 | 10/2017 | Sigurdsson et al. |
| 9,790,253 B2 | 10/2017 | Shair et al. |
| 9,821,114 B2 | 11/2017 | Cabrera Aquino et al. |
| 9,879,076 B2 | 1/2018 | Samira et al. |
| 9,903,855 B2 | 2/2018 | Cheresh et al. |
| 9,907,485 B2 | 3/2018 | Hartlep et al. |
| 9,921,230 B2 | 3/2018 | Chodobski et al. |
| 9,933,440 B2 | 4/2018 | Goetzl |
| 9,937,248 B2 | 4/2018 | Arya |
| 9,999,624 B2 | 6/2018 | May et al. |
| 10,011,653 B2 | 7/2018 | Hayashi et al. |
| 10,028,962 B2 | 7/2018 | Brodney et al. |
| 10,117,895 B2 | 11/2018 | Monsonego |
| 10,131,708 B2 | 11/2018 | Nitsch et al. |
| 10,203,342 B2 | 2/2019 | Goetzl |
| 10,213,462 B2 | 2/2019 | Eliaz |
| 10,232,056 B2 | 3/2019 | Uchida et al. |
| 10,323,084 B2 | 6/2019 | Hillen et al. |
| 10,358,503 B2 | 7/2019 | Sigurdsson |
| 10,364,286 B2 | 7/2019 | Fog et al. |
| 10,377,834 B2 | 8/2019 | De Strooper et al. |
| 10,393,757 B2 | 8/2019 | Hashimoto et al. |
| 10,420,923 B1 | 9/2019 | Katz |
| 10,421,958 B2 | 9/2019 | Poma et al. |
| 10,472,414 B2 | 11/2019 | Christensen et al. |
| 10,473,672 B2 | 11/2019 | Lin et al. |
| 10,532,104 B2 | 1/2020 | Elmaleh |
| 10,570,196 B2 | 2/2020 | Ghochikyan et al. |
| 10,654,917 B2 | 5/2020 | Volker et al. |
| 10,662,226 B2 | 5/2020 | Nowick et al. |
| 10,662,239 B2 | 5/2020 | Groves et al. |

(56) References Cited

U.S. PATENT DOCUMENTS

| | | | |
|---|---|---|---|
| 10,662,246 B2 | 5/2020 | Wisniewski et al. |
| 10,670,613 B2 | 6/2020 | Umek et al. |
| 10,718,785 B2 | 7/2020 | Pike et al. |
| 10,730,937 B2 | 8/2020 | Okazawa et al. |
| 10,738,107 B2 | 8/2020 | Gnauer et al. |
| 10,792,349 B2* | 10/2020 | Jaffee ................ A61K 39/0005 |
| 10,815,230 B2 | 10/2020 | Pike et al. |
| 10,815,469 B2 | 10/2020 | Poma et al. |
| 10,822,402 B2 | 11/2020 | Dengl et al. |
| 10,828,413 B2 | 11/2020 | Eliaz |
| 10,836,814 B2 | 11/2020 | Goshima et al. |
| 10,837,966 B2 | 11/2020 | Hodi et al. |
| 10,842,871 B2 | 11/2020 | Ferrero et al. |
| 10,851,156 B2 | 12/2020 | Mercken et al. |
| 10,859,582 B2 | 12/2020 | Sigurdsson et al. |
| 10,874,725 B2 | 12/2020 | Henco et al. |
| 10,888,600 B2 | 1/2021 | Tanzi et al. |
| 10,894,822 B2 | 1/2021 | Chain |
| 10,919,971 B2 | 2/2021 | Collinge et al. |
| 10,934,348 B2 | 3/2021 | Pedersen et al. |
| 10,941,205 B2 | 3/2021 | Duerr et al. |
| 10,941,215 B2 | 3/2021 | Dennis et al. |
| 10,954,306 B2 | 3/2021 | Greenfield et al. |
| 10,976,319 B2 | 4/2021 | Pugia |
| 10,981,989 B2 | 4/2021 | Eisenbach et al. |
| 10,988,528 B2 | 4/2021 | Sigurdsson |
| 11,084,873 B2 | 8/2021 | Shie et al. |
| 11,085,935 B2 | 8/2021 | Barthelemy et al. |
| 11,091,552 B2 | 8/2021 | Fontayne et al. |
| 11,098,106 B2 | 8/2021 | Novák et al. |
| 11,111,290 B2 | 9/2021 | Pedersen et al. |
| 11,135,313 B2 | 10/2021 | Wilson et al. |
| 11,181,533 B2 | 11/2021 | Shi et al. |
| 11,214,835 B1 | 1/2022 | Patel et al. |
| 11,219,627 B2 | 1/2022 | Davis et al. |
| 11,236,155 B2 | 2/2022 | Van et al. |
| 11,278,620 B2 | 3/2022 | Liang et al. |
| 11,286,297 B2 | 3/2022 | Groves et al. |
| 11,312,751 B2 | 4/2022 | Poma et al. |
| 11,319,372 B2 | 5/2022 | Calzone et al. |
| 11,365,223 B2 | 6/2022 | Poma et al. |
| 11,370,833 B2 | 6/2022 | Le et al. |
| 11,389,476 B2 | 7/2022 | Eliaz |
| 11,395,796 B2 | 7/2022 | Romanelli et al. |
| 11,396,553 B2 | 7/2022 | Oostindie et al. |
| 11,413,282 B2 | 8/2022 | Sampath et al. |
| 11,434,302 B2 | 9/2022 | Raum et al. |
| 11,439,665 B2 | 9/2022 | Yao et al. |
| 11,446,398 B2 | 9/2022 | Barrett et al. |
| 11,459,404 B2 | 10/2022 | Bacac et al. |
| 11,459,405 B2 | 10/2022 | Sasisekharan et al. |
| 11,466,099 B2 | 10/2022 | Garcia et al. |
| 11,471,490 B2 | 10/2022 | Andresen et al. |
| 11,472,858 B2 | 10/2022 | Yao et al. |
| 11,478,554 B2 | 10/2022 | Lerchen et al. |
| 11,505,609 B2 | 11/2022 | Qin et al. |
| 11,512,137 B2 | 11/2022 | Oostindie et al. |
| 11,518,810 B2 | 12/2022 | Song et al. |
| 11,525,007 B2 | 12/2022 | Bruenker et al. |
| 11,535,838 B2 | 12/2022 | Rosenblum et al. |
| 11,583,594 B2 | 2/2023 | Xie |
| 11,584,793 B2 | 2/2023 | Dengl et al. |
| 11,590,128 B2 | 2/2023 | Sampath et al. |
| 11,596,699 B2 | 3/2023 | Fotin-Mleczek |
| 11,597,772 B2 | 3/2023 | Oestergaard et al. |
| 11,603,411 B2 | 3/2023 | Duerr et al. |
| 11,608,369 B2 | 3/2023 | Yao et al. |
| 11,608,376 B2 | 3/2023 | Georges et al. |
| 11,618,778 B2 | 4/2023 | Yao et al. |
| 11,633,430 B2 | 4/2023 | Yao et al. |
| 11,634,486 B2 | 4/2023 | Jefferies et al. |
| 11,654,143 B2 | 5/2023 | Hamdy et al. |
| 11,660,351 B2 | 5/2023 | Lerchen et al. |
| 11,666,642 B2 | 6/2023 | Suri et al. |
| 11,679,127 B2 | 6/2023 | Stubenrauch et al. |
| 11,685,714 B2 | 6/2023 | Lerchen et al. |
| 11,713,358 B2 | 8/2023 | Schellenberger et al. |
| 11,718,680 B2 | 8/2023 | Bacac et al. |
| 11,746,161 B2 | 9/2023 | Chen et al. |
| 11,753,466 B2 | 9/2023 | West et al. |
| 11,768,203 B2 | 9/2023 | Chaudhary |
| 11,771,696 B2 | 10/2023 | Hamdy et al. |
| 11,788,205 B2 | 10/2023 | Klein et al. |
| 11,833,214 B2 | 12/2023 | Hilderbrand et al. |
| 11,857,628 B2 | 1/2024 | Poma et al. |
| 11,866,507 B2 | 1/2024 | Eckelman |
| 11,867,696 B2 | 1/2024 | Schwartz |
| 11,873,332 B2 | 1/2024 | Soto et al. |
| 11,873,342 B2 | 1/2024 | Li et al. |
| 11,891,444 B2 | 2/2024 | Gauthier et al. |
| 11,912,759 B2 | 2/2024 | Liu et al. |
| 11,913,945 B2 | 2/2024 | Schaefer et al. |
| 2002/0076738 A1 | 6/2002 | Woo |
| 2002/0155513 A1 | 10/2002 | Hsu et al. |
| 2003/0133939 A1 | 7/2003 | Ledbetter et al. |
| 2004/0022397 A1* | 2/2004 | Warren ................. H04R 3/005 381/92 |
| 2004/0223971 A1 | 11/2004 | Chang |
| 2005/0032673 A1 | 2/2005 | John et al. |
| 2005/0084915 A1 | 4/2005 | Woo |
| 2005/0158321 A1 | 7/2005 | Hurez et al. |
| 2006/0148712 A1 | 7/2006 | Liu et al. |
| 2006/0240551 A1 | 10/2006 | Jiang |
| 2006/0246496 A1 | 11/2006 | Ahmed et al. |
| 2006/0257359 A1 | 11/2006 | Francois et al. |
| 2006/0257946 A1 | 11/2006 | Ding et al. |
| 2008/0219973 A1 | 9/2008 | Sasaki et al. |
| 2009/0280116 A1 | 11/2009 | Smith et al. |
| 2009/0311193 A1 | 12/2009 | Mauro et al. |
| 2010/0061992 A1 | 3/2010 | Anderson et al. |
| 2010/0098683 A1 | 4/2010 | Kufe |
| 2010/0104587 A1 | 4/2010 | Chavan et al. |
| 2010/0143954 A1 | 6/2010 | Muntendam |
| 2010/0196882 A1 | 8/2010 | Raz et al. |
| 2010/0330602 A1 | 12/2010 | Van Meir et al. |
| 2011/0038861 A1 | 2/2011 | Rosenthal et al. |
| 2011/0293608 A1* | 12/2011 | Jaffee .................... C07K 16/18 424/133.1 |
| 2012/0046181 A1 | 2/2012 | Harb et al. |
| 2012/0225114 A1 | 9/2012 | Francois et al. |
| 2012/0253160 A1 | 10/2012 | Mauro et al. |
| 2013/0029900 A1 | 1/2013 | Widdison |
| 2013/0029955 A1* | 1/2013 | Muntendam ......... A23L 29/231 435/7.1 |
| 2013/0045882 A1 | 2/2013 | Klass et al. |
| 2013/0065258 A1 | 3/2013 | Watanabe et al. |
| 2013/0323268 A1 | 12/2013 | Chari et al. |
| 2014/0086836 A1 | 3/2014 | Burnham et al. |
| 2014/0086932 A1* | 3/2014 | Traber ............... C07K 16/2818 424/144.1 |
| 2014/0099254 A1 | 4/2014 | Chang et al. |
| 2014/0105997 A1 | 4/2014 | Eliaz |
| 2014/0235495 A1 | 8/2014 | Pugia |
| 2014/0286970 A1 | 9/2014 | Jeffrey et al. |
| 2014/0294862 A1 | 10/2014 | Chavan et al. |
| 2014/0294868 A1 | 10/2014 | Howard et al. |
| 2014/0370521 A1 | 12/2014 | Porter et al. |
| 2015/0105539 A1 | 4/2015 | Miao et al. |
| 2015/0105540 A1 | 4/2015 | Miao et al. |
| 2015/0150945 A1 | 6/2015 | Francois et al. |
| 2015/0218274 A1 | 8/2015 | Sabatos-Peyton et al. |
| 2015/0301058 A1 | 10/2015 | Schettini et al. |
| 2015/0329636 A1 | 11/2015 | Dennis et al. |
| 2015/0377905 A1 | 12/2015 | Burns et al. |
| 2016/0068577 A1 | 3/2016 | Poma et al. |
| 2016/0166686 A1 | 6/2016 | McNeel et al. |
| 2016/0177284 A1 | 6/2016 | Poma et al. |
| 2016/0199470 A1 | 7/2016 | Chavan et al. |
| 2016/0376328 A1 | 12/2016 | Poma et al. |
| 2017/0002046 A1 | 1/2017 | Poma et al. |
| 2017/0014446 A1 | 1/2017 | Rolke et al. |
| 2017/0056498 A1 | 3/2017 | Krause et al. |
| 2017/0153241 A1 | 6/2017 | Pugia |
| 2017/0275353 A1 | 9/2017 | Sheng et al. |

(56) References Cited

U.S. PATENT DOCUMENTS

| | | |
|---|---|---|
| 2017/0355756 A1 | 12/2017 | Julien |
| 2017/0363620 A1 | 12/2017 | Beshiri et al. |
| 2017/0363637 A1 | 12/2017 | Takata et al. |
| 2017/0370944 A1 | 12/2017 | Muntendam et al. |
| 2018/0000899 A1 | 1/2018 | Francois et al. |
| 2018/0243432 A1 | 8/2018 | Poma et al. |
| 2018/0256747 A1 | 9/2018 | Hawthorne et al. |
| 2018/0291359 A1 | 10/2018 | Poma et al. |
| 2019/0153044 A1 | 5/2019 | Poma et al. |
| 2019/0175649 A1 | 6/2019 | Novik |
| 2019/0248902 A1 | 8/2019 | Nioi |
| 2019/0265235 A1 | 8/2019 | Schwartz et al. |
| 2019/0374650 A1 | 12/2019 | Moon et al. |
| 2020/0024312 A1 | 1/2020 | Poma et al. |
| 2020/0055938 A1 | 2/2020 | Desai |
| 2020/0078398 A1 | 3/2020 | Eliaz |
| 2020/0085866 A1 | 3/2020 | Eliaz |
| 2020/0085867 A1 | 3/2020 | Eliaz |
| 2021/0001032 A1 | 1/2021 | Eliaz |
| 2021/0032350 A1 | 2/2021 | Spriggs et al. |
| 2021/0102948 A1 | 4/2021 | Hodi et al. |
| 2021/0115123 A1 | 4/2021 | Sheng et al. |
| 2021/0132067 A1 | 5/2021 | Schwartz |
| 2021/0177794 A1 | 6/2021 | Steineger et al. |
| 2021/0246211 A1 | 8/2021 | Goldberg et al. |
| 2021/0324056 A1 | 10/2021 | Luthman et al. |
| 2021/0363255 A1 | 11/2021 | Sun et al. |
| 2021/0371533 A1 | 12/2021 | Sun et al. |
| 2021/0401985 A1 | 12/2021 | Biel et al. |
| 2022/0002420 A1* | 1/2022 | Sun .................. A61P 35/00 |
| 2022/0025071 A1 | 1/2022 | Capon |
| 2022/0040172 A1 | 2/2022 | Li et al. |
| 2022/0088013 A1 | 3/2022 | Hamdy et al. |
| 2022/0088195 A1 | 3/2022 | Klein et al. |
| 2022/0098329 A1 | 3/2022 | Santich et al. |
| 2022/0125942 A1 | 4/2022 | Musick et al. |
| 2022/0127366 A1 | 4/2022 | Fotakis et al. |
| 2022/0133711 A1 | 5/2022 | Chari et al. |
| 2022/0135678 A1 | 5/2022 | Chaudhary |
| 2022/0162316 A1 | 5/2022 | Pandit et al. |
| 2022/0168418 A1 | 6/2022 | Haegel et al. |
| 2022/0184127 A1 | 6/2022 | Wang et al. |
| 2022/0195043 A1 | 6/2022 | Li et al. |
| 2022/0195057 A1 | 6/2022 | Li et al. |
| 2022/0195071 A1 | 6/2022 | Jones |
| 2022/0204582 A1 | 6/2022 | Chaudhary |
| 2022/0211696 A1 | 7/2022 | Sampath et al. |
| 2022/0211865 A1 | 7/2022 | Fischer et al. |
| 2022/0226514 A1 | 7/2022 | Vasiljeva et al. |
| 2022/0233705 A1 | 7/2022 | Le Scolan et al. |
| 2022/0242936 A1 | 8/2022 | Feng et al. |
| 2022/0242949 A1 | 8/2022 | Desnoyers et al. |
| 2022/0244271 A1 | 8/2022 | Reed et al. |
| 2022/0251231 A1 | 8/2022 | Oostindie et al. |
| 2022/0257762 A1 | 8/2022 | Liang et al. |
| 2022/0259306 A1 | 8/2022 | Duan et al. |
| 2022/0259321 A1 | 8/2022 | Cascino |
| 2022/0265642 A1 | 8/2022 | Sampath et al. |
| 2022/0267460 A1 | 8/2022 | Lansing et al. |
| 2022/0275067 A1 | 9/2022 | Dolan, III et al. |
| 2022/0281945 A1 | 9/2022 | Yao et al. |
| 2022/0288123 A1 | 9/2022 | Yao et al. |
| 2022/0289173 A1 | 9/2022 | Sun et al. |
| 2022/0289858 A1 | 9/2022 | Benatuil et al. |
| 2022/0306761 A1 | 9/2022 | Duerr et al. |
| 2022/0324940 A1 | 10/2022 | Yao et al. |
| 2022/0332757 A1 | 10/2022 | Zhang et al. |
| 2022/0340640 A1 | 10/2022 | Yao et al. |
| 2022/0340677 A1 | 10/2022 | Zhang et al. |
| 2022/0354938 A1 | 11/2022 | Poma et al. |
| 2022/0357340 A1 | 11/2022 | Brady et al. |
| 2022/0370441 A1 | 11/2022 | Sampath et al. |
| 2022/0372142 A1 | 11/2022 | Baliga et al. |
| 2022/0372156 A1 | 11/2022 | Lechner et al. |
| 2022/0380473 A1 | 12/2022 | Sun et al. |
| 2022/0380480 A1 | 12/2022 | Lechner et al. |
| 2022/0389116 A1 | 12/2022 | Klein et al. |
| 2022/0389449 A1 | 12/2022 | Paul et al. |
| 2022/0396632 A1 | 12/2022 | Novobrantseva et al. |
| 2022/0402998 A1 | 12/2022 | Liu et al. |
| 2022/0403001 A1 | 12/2022 | Suri et al. |
| 2022/0403027 A1 | 12/2022 | Ast et al. |
| 2023/0039927 A1 | 2/2023 | Cascino |
| 2023/0046007 A1 | 2/2023 | Bauer et al. |
| 2023/0048390 A1 | 2/2023 | Liebowitz |
| 2023/0052521 A1 | 2/2023 | Bacac et al. |
| 2023/0074330 A1 | 3/2023 | Suri et al. |
| 2023/0074657 A1 | 3/2023 | Song et al. |
| 2023/0081117 A1 | 3/2023 | Oakes et al. |
| 2023/0082273 A1 | 3/2023 | Song et al. |
| 2023/0084763 A1 | 3/2023 | Chen et al. |
| 2023/0091653 A1 | 3/2023 | Bindman et al. |
| 2023/0094463 A1 | 3/2023 | Sun et al. |
| 2023/0094471 A1 | 3/2023 | Chari et al. |
| 2023/0099756 A1 | 3/2023 | Hirata et al. |
| 2023/0103667 A1 | 4/2023 | Muntendam et al. |
| 2023/0104705 A1 | 4/2023 | Yao et al. |
| 2023/0107479 A1 | 4/2023 | Muntendam |
| 2023/0121775 A1 | 4/2023 | Schellenberger et al. |
| 2023/0140802 A1 | 5/2023 | Chaudhary |
| 2023/0151104 A1 | 5/2023 | Yan et al. |
| 2023/0190638 A1 | 6/2023 | Romanelli et al. |
| 2023/0192884 A1 | 6/2023 | Raum et al. |
| 2023/0192898 A1 | 6/2023 | Zhou et al. |
| 2023/0197278 A1 | 6/2023 | Griffin et al. |
| 2023/0201364 A1 | 6/2023 | Pattabiraman et al. |
| 2023/0201365 A1 | 6/2023 | Kreft et al. |
| 2023/0203117 A1 | 6/2023 | Gorby et al. |
| 2023/0203169 A1 | 6/2023 | Qin et al. |
| 2023/0203199 A1 | 6/2023 | Wei et al. |
| 2023/0203467 A1 | 6/2023 | Rosenblum et al. |
| 2023/0203532 A1 | 6/2023 | Iikow et al. |
| 2023/0212255 A1 | 7/2023 | Yao et al. |
| 2023/0212303 A1 | 7/2023 | Umana et al. |
| 2023/0212319 A1 | 7/2023 | Chaudhary |
| 2023/0220071 A1 | 7/2023 | Dengl et al. |
| 2023/0220113 A1 | 7/2023 | Garcia et al. |
| 2023/0220115 A1 | 7/2023 | Capon |
| 2023/0220116 A1 | 7/2023 | Capon |
| 2023/0221333 A1 | 7/2023 | Sandoval et al. |
| 2023/0226045 A1 | 7/2023 | Sampath et al. |
| 2023/0227553 A1 | 7/2023 | Wei et al. |
| 2023/0235075 A1 | 7/2023 | Chen et al. |
| 2023/0235092 A1 | 7/2023 | Wei et al. |
| 2023/0242613 A1 | 8/2023 | Yao et al. |
| 2023/0255959 A1 | 8/2023 | Sampath et al. |
| 2023/0256092 A1 | 8/2023 | Tanaka et al. |
| 2023/0265204 A1 | 8/2023 | Shao |
| 2023/0270875 A1 | 8/2023 | Hirata et al. |
| 2023/0272092 A1 | 8/2023 | Paller et al. |
| 2023/0279120 A1 | 9/2023 | Sun et al. |
| 2023/0285588 A1 | 9/2023 | Shahar et al. |
| 2023/0287040 A1 | 9/2023 | Schellenberger et al. |
| 2023/0287118 A1 | 9/2023 | Ast et al. |
| 2023/0295327 A1 | 9/2023 | Lee et al. |
| 2023/0295334 A1 | 9/2023 | Schellenberger et al. |
| 2023/0295336 A1 | 9/2023 | Eckelman et al. |
| 2023/0322935 A1 | 10/2023 | Chen et al. |
| 2023/0322950 A1 | 10/2023 | Darowski et al. |
| 2023/0324389 A1 | 10/2023 | Schellenberger et al. |
| 2023/0331839 A1 | 10/2023 | Jefferies et al. |
| 2023/0338559 A1 | 10/2023 | Lerchen et al. |
| 2023/0340155 A1 | 10/2023 | Chen et al. |
| 2023/0340160 A1 | 10/2023 | Ast et al. |
| 2023/0348600 A1 | 11/2023 | Timmer et al. |
| 2023/0348611 A1 | 11/2023 | Oestergaard |
| 2023/0348612 A1 | 11/2023 | Lin et al. |
| 2023/0348628 A1 | 11/2023 | Meux et al. |
| 2023/0348995 A1 | 11/2023 | Paulson et al. |
| 2023/0357431 A1 | 11/2023 | Darowski et al. |
| 2023/0365705 A1 | 11/2023 | Chen et al. |
| 2023/0366884 A1 | 11/2023 | Zettl et al. |
| 2023/0372479 A1 | 11/2023 | Bacac et al. |
| 2023/0381321 A1 | 11/2023 | Lyski et al. |

(56) References Cited

U.S. PATENT DOCUMENTS

| | | |
|---|---|---|
| 2023/0390338 A1 | 12/2023 | Stubenrauch et al. |
| 2023/0399414 A1 | 12/2023 | Oostindie et al. |
| 2023/0406930 A1 | 12/2023 | Ji et al. |
| 2023/0414750 A1 | 12/2023 | Filippou-Frye et al. |
| 2023/0416365 A1 | 12/2023 | Georges et al. |
| 2023/0416412 A1 | 12/2023 | Leclercq-Cohen et al. |
| 2024/0000776 A1 | 1/2024 | Sampath et al. |
| 2024/0002546 A1 | 1/2024 | Codarri et al. |
| 2024/0018204 A1 | 1/2024 | Kim et al. |
| 2024/0018260 A1 | 1/2024 | Schellenberger et al. |
| 2024/0026009 A1 | 1/2024 | Spriggs et al. |
| 2024/0033351 A1 | 2/2024 | Brunetta |
| 2024/0043379 A1 | 2/2024 | Lerchen et al. |
| 2024/0043535 A1 | 2/2024 | Amann et al. |
| 2024/0043554 A1 | 2/2024 | Maller et al. |
| 2024/0050562 A1 | 2/2024 | Fujimura et al. |
| 2024/0058443 A1 | 2/2024 | Haegel et al. |
| 2024/0059785 A1 | 2/2024 | Liu et al. |
| 2024/0059798 A1 | 2/2024 | Xu et al. |
| 2024/0158512 A1 | 5/2024 | Sun et al. |
| 2024/0182564 A1 | 6/2024 | Sun et al. |

FOREIGN PATENT DOCUMENTS

| | | |
|---|---|---|
| EP | 1 074 634 B1 | 2/2001 |
| EP | 0 651 809 B1 | 12/2001 |
| EP | 0 728 215 B1 | 2/2002 |
| EP | 0 817 969 B1 | 7/2002 |
| EP | 0 935 457 B1 | 1/2004 |
| EP | 0 610 254 B1 | 9/2004 |
| EP | 0 783 523 B1 | 10/2004 |
| EP | 0 792 458 B1 | 10/2004 |
| EP | 1 221 480 B1 | 5/2005 |
| EP | 0 846 171 B1 | 9/2005 |
| EP | 1 156 811 B1 | 12/2005 |
| EP | 1 490 692 B1 | 1/2006 |
| EP | 0 699 755 | 3/2006 |
| EP | 1 104 307 B1 | 6/2006 |
| EP | 0 909 316 B1 | 8/2006 |
| EP | 0 890 105 B1 | 11/2006 |
| EP | 1 481 007 B1 | 1/2007 |
| EP | 1 161 524 B1 | 2/2007 |
| EP | 1 172 377 B1 | 4/2007 |
| EP | 1 697 370 B1 | 4/2007 |
| EP | 0 970 203 B1 | 5/2007 |
| EP | 1 379 546 B1 | 6/2007 |
| EP | 1 402 034 B1 | 6/2007 |
| EP | 1 485 410 B1 | 6/2007 |
| EP | 1 392 728 B1 | 8/2007 |
| EP | 1 516 189 B1 | 11/2007 |
| EP | 1 385 531 B1 | 5/2008 |
| EP | 1 781 644 B1 | 5/2008 |
| EP | 1 617 849 B1 | 6/2008 |
| EP | 0 932 674 B1 | 7/2008 |
| EP | 1 379 882 B1 | 7/2008 |
| EP | 1 521 774 B1 | 8/2008 |
| EP | 1 353 691 B1 | 1/2009 |
| EP | 1 476 757 B1 | 1/2009 |
| EP | 1 590 673 B1 | 4/2009 |
| EP | 1 623 719 B1 | 7/2009 |
| EP | 0 911 390 B1 | 8/2009 |
| EP | 0 966 533 B1 | 9/2009 |
| EP | 1 891 215 B1 | 10/2009 |
| EP | 1 497 661 B1 | 11/2009 |
| EP | 1 721 008 B1 | 2/2010 |
| EP | 1 180 938 B1 | 3/2010 |
| EP | 1 355 949 B1 | 3/2010 |
| EP | 1 797 123 B1 | 3/2010 |
| EP | 1 255 824 B1 | 4/2010 |
| EP | 1 423 704 B1 | 4/2010 |
| EP | 0 996 463 B1 | 5/2010 |
| EP | 1 596 809 B1 | 5/2010 |
| EP | 1 896 430 B1 | 11/2010 |
| EP | 1 891 241 B1 | 1/2011 |
| EP | 1 524 994 B1 | 4/2011 |
| EP | 1 404 710 B1 | 6/2011 |
| EP | 1 879 613 B1 | 11/2011 |
| EP | 1 885 886 B1 | 11/2011 |
| EP | 1 636 268 | 2/2012 |
| EP | 1 480 666 B1 | 6/2012 |
| EP | 1 554 311 B1 | 6/2012 |
| EP | 2 140 247 B1 | 6/2012 |
| EP | 1 838 854 B1 | 10/2012 |
| EP | 2 297 196 B1 | 11/2012 |
| EP | 1 842 859 B1 | 1/2013 |
| EP | 2 185 592 B1 | 1/2013 |
| EP | 1 765 388 B1 | 4/2013 |
| EP | 2 240 602 B1 | 5/2013 |
| EP | 2 356 996 B1 | 6/2013 |
| EP | 2 380 583 B1 | 8/2013 |
| EP | 1 776 591 B1 | 10/2013 |
| EP | 2 165 714 B1 | 10/2013 |
| EP | 2 345 411 B1 | 10/2013 |
| EP | 1 670 943 B1 | 11/2013 |
| EP | 2 207 885 B1 | 11/2013 |
| EP | 2 364 719 B1 | 11/2013 |
| EP | 1 976 877 B1 | 1/2014 |
| EP | 2 423 311 B1 | 1/2014 |
| EP | 1 937 720 B1 | 4/2014 |
| EP | 2 182 983 B1 | 5/2014 |
| EP | 2 379 563 B1 | 7/2014 |
| EP | 1 678 505 B1 | 8/2014 |
| EP | 1 891 234 B1 | 12/2014 |
| EP | 2 354 795 B1 | 12/2014 |
| EP | 1 669 085 B1 | 1/2015 |
| EP | 2 365 976 B1 | 4/2015 |
| EP | 1 594 969 B1 | 5/2015 |
| EP | 1 781 703 B1 | 5/2015 |
| EP | 2 441 847 B1 | 9/2015 |
| EP | 1 420 032 B2 | 12/2015 |
| EP | 2 262 526 B1 | 12/2015 |
| EP | 2 470 211 B1 | 1/2016 |
| EP | 2 116 556 B1 | 3/2016 |
| EP | 2 500 361 B1 | 3/2016 |
| EP | 2 593 475 B1 | 3/2016 |
| EP | 2 470 911 B1 | 4/2016 |
| EP | 2 454 599 B1 | 5/2016 |
| EP | 2 238 160 B1 | 6/2016 |
| EP | 2 330 113 B1 | 6/2016 |
| EP | 1 877 442 B1 | 8/2016 |
| EP | 2 443 149 B1 | 8/2016 |
| EP | 2 104 682 B1 | 9/2016 |
| EP | 2 011 513 B1 | 10/2016 |
| EP | 2 051 734 B1 | 10/2016 |
| EP | 2 842 967 B1 | 11/2016 |
| EP | 2 819 700 B1 | 12/2016 |
| EP | 2 694 124 B1 | 1/2017 |
| EP | 2 550 361 B1 | 2/2017 |
| EP | 2 462 161 B1 | 3/2017 |
| EP | 1 989 308 B1 | 5/2017 |
| EP | 2 207 568 B1 | 5/2017 |
| EP | 2 299 812 B1 | 7/2017 |
| EP | 2 149 584 B1 | 12/2017 |
| EP | 2 828 660 B1 | 12/2017 |
| EP | 2 463 368 B1 | 1/2018 |
| EP | 2 788 761 B1 | 2/2018 |
| EP | 2 740 744 B1 | 3/2018 |
| EP | 3 043 802 B1 | 4/2018 |
| EP | 3 121 277 B1 | 4/2018 |
| EP | 2 514 823 B1 | 5/2018 |
| EP | 2 307 457 B1 | 6/2018 |
| EP | 2 356 144 B1 | 7/2018 |
| EP | 3 050 898 B1 | 8/2018 |
| EP | 3 056 510 B1 | 10/2018 |
| EP | 2 758 077 B1 | 12/2018 |
| EP | 2 802 602 B1 | 3/2019 |
| EP | 2 994 160 B1 | 7/2019 |
| EP | 3 003 356 B1 | 7/2019 |
| EP | 3 066 475 B1 | 7/2019 |
| EP | 3 013 355 B1 | 8/2019 |
| EP | 2 789 695 B1 | 10/2019 |
| EP | 2 834 270 B1 | 10/2019 |
| EP | 2 961 426 B1 | 10/2019 |
| EP | 3 274 010 B1 | 10/2019 |

(56) References Cited

FOREIGN PATENT DOCUMENTS

| | | |
|---|---|---|
| EP | 3 269 736 B1 | 11/2019 |
| EP | 3 339 323 B1 | 11/2019 |
| EP | 3 083 680 B1 | 1/2020 |
| EP | 3 164 152 B1 | 2/2020 |
| EP | 3 225 251 B1 | 2/2020 |
| EP | 2 814 963 B1 | 4/2020 |
| EP | 2 224 000 B1 | 5/2020 |
| EP | 2 831 584 B1 | 6/2020 |
| EP | 2 968 548 B1 | 9/2020 |
| EP | 3 324 186 B1 | 9/2020 |
| EP | 3 221 349 B1 | 11/2020 |
| EP | 2 448 968 B1 | 1/2021 |
| EP | 3 166 970 B1 | 3/2021 |
| EP | 3 436 010 B1 | 3/2021 |
| EP | 3 102 230 B1 | 4/2021 |
| EP | 3 197 445 B1 | 4/2021 |
| EP | 3 281 614 B1 | 6/2021 |
| EP | 2 408 807 B1 | 7/2021 |
| EP | 3 070 100 B1 | 7/2021 |
| EP | 3 353 214 B1 | 8/2021 |
| EP | 1 812 062 B1 | 3/2022 |
| EP | 4 129 335 A1 | 2/2023 |
| EP | 4 176 900 A1 | 5/2023 |
| EP | 4 186 926 A1 | 5/2023 |
| FR | 2994803 | 3/2014 |
| JP | 2012507724 A | 3/2012 |
| WO | WO 1993/011161 A1 | 6/1993 |
| WO | WO 1994/013804 A1 | 6/1994 |
| WO | WO 00/24782 | 5/2000 |
| WO | WO 02/025246 A2 | 4/2002 |
| WO | WO 2005/033144 A2 | 4/2005 |
| WO | WO 06/06198 A2 | 6/2006 |
| WO | WO 08/068048 | 6/2008 |
| WO | WO 08/085564 | 7/2008 |
| WO | WO 08/112559 | 9/2008 |
| WO | WO 10/005858 A1 | 1/2010 |
| WO | WO 10/056722 A1 | 5/2010 |
| WO | WO 10/095042 A2 | 8/2010 |
| WO | WO 10/147969 A2 | 12/2010 |
| WO | WO 13/017891 | 2/2013 |
| WO | WO 13/169890 | 11/2013 |
| WO | WO 14/140317 | 9/2014 |
| WO | WO 15/038426 | 3/2015 |
| WO | WO 15/051850 | 4/2015 |
| WO | WO 15/052345 | 4/2015 |
| WO | WO 15/117002 | 8/2015 |
| WO | WO 15/138438 | 9/2015 |
| WO | WO 16/004093 | 1/2016 |
| WO | WO 16/059453 A1 | 4/2016 |
| WO | WO 17/080973 | 5/2017 |
| WO | WO 18/058098 A1 | 3/2018 |
| WO | WO 18/115003 | 6/2018 |
| WO | WO 18/19188 | 7/2018 |
| WO | WO 18/119351 | 7/2018 |
| WO | WO 18/209276 | 11/2018 |
| WO | WO 2019/023247 A1 | 1/2019 |
| WO | WO 19/024784 A1 | 2/2019 |
| WO | WO 19/028357 | 2/2019 |
| WO | WO 19/074840 A1 | 4/2019 |
| WO | WO 19/079496 A2 | 4/2019 |
| WO | WO 19/084332 A1 | 5/2019 |
| WO | WO 19/089080 | 5/2019 |
| WO | WO 19/094679 A1 | 5/2019 |
| WO | WO 19/134481 A1 | 7/2019 |
| WO | WO 19/137922 A1 | 7/2019 |
| WO | WO 19/143125 A1 | 7/2019 |
| WO | WO 19/150183 A1 | 8/2019 |
| WO | WO 19/152895 | 8/2019 |
| WO | WO 19/161384 A1 | 8/2019 |
| WO | WO 19/165240 A1 | 8/2019 |
| WO | WO 19/165421 | 8/2019 |
| WO | WO 2019/165233 A1 | 8/2019 |
| WO | WO 19/168403 A2 | 9/2019 |
| WO | WO 19/173795 A2 | 9/2019 |
| WO | WO 19/186276 | 10/2019 |
| WO | WO 19/191518 A1 | 10/2019 |
| WO | WO 19/198825 A1 | 10/2019 |
| WO | WO 19/207159 A1 | 10/2019 |
| WO | WO 2019/195621 A1 | 10/2019 |
| WO | WO 19/222441 A1 | 11/2019 |
| WO | WO 19/243453 A1 | 12/2019 |
| WO | WO 19/246422 A1 | 12/2019 |
| WO | WO 20/023530 | 1/2020 |
| WO | WO 20/037258 A1 | 2/2020 |
| WO | WO 20/045646 A1 | 3/2020 |
| WO | WO 20/055975 A1 | 3/2020 |
| WO | WO 20/059847 A1 | 3/2020 |
| WO | WO 20/069621 A1 | 4/2020 |
| WO | WO 20/070225 A1 | 4/2020 |
| WO | WO 20/079244 A1 | 4/2020 |
| WO | WO 20/084346 A1 | 4/2020 |
| WO | WO 20/092107 A1 | 5/2020 |
| WO | WO 20/092202 A2 | 5/2020 |
| WO | WO 20/112889 | 6/2020 |
| WO | WO 20/117560 A1 | 6/2020 |
| WO | WO 20/123492 A1 | 6/2020 |
| WO | WO 20/138402 A1 | 7/2020 |
| WO | WO 20/154475 | 7/2020 |
| WO | WO 20/160156 | 8/2020 |
| WO | WO 20/163730 A2 | 8/2020 |
| WO | WO 20/171724 | 8/2020 |
| WO | WO 20/172621 | 8/2020 |
| WO | WO 20/1654353 A1 | 8/2020 |
| WO | WO 20/185676 A1 | 9/2020 |
| WO | WO 20/219646 A1 | 10/2020 |
| WO | WO 20/219868 A1 | 10/2020 |
| WO | WO 20/225799 A2 | 11/2020 |
| WO | WO 20/227376 | 11/2020 |
| WO | WO 20/257745 A1 | 12/2020 |
| WO | WO 20/263862 A1 | 12/2020 |
| WO | WO 20/264211 A1 | 12/2020 |
| WO | WO 21/002312 A1 | 1/2021 |
| WO | WO 21/007110 A1 | 1/2021 |
| WO | WO 21/011673 | 1/2021 |
| WO | WO 21/012082 A1 | 1/2021 |
| WO | WO 21/028590 A1 | 2/2021 |
| WO | WO 21/048619 A2 | 3/2021 |
| WO | WO 21/055583 A1 | 3/2021 |
| WO | WO 21/052361 A2 | 4/2021 |
| WO | WO 21/068879 A1 | 4/2021 |
| WO | WO 21/071830 A1 | 4/2021 |
| WO | WO 21/078942 A1 | 4/2021 |
| WO | WO 21/081101 A1 | 4/2021 |
| WO | WO 21/084274 A1 | 5/2021 |
| WO | WO 21/08809 A1 | 6/2021 |
| WO | WO 21/113527 | 6/2021 |
| WO | WO 21/146218 | 7/2021 |
| WO | WO 21/157634 A1 | 8/2021 |
| WO | WO 21/163346 A2 | 8/2021 |
| WO | WO 21/163681 A2 | 8/2021 |
| WO | WO 21/167723 A1 | 8/2021 |
| WO | WO 21/184404 A1 | 9/2021 |
| WO | WO 21/186079 A1 | 9/2021 |
| WO | WO 21/190558 A1 | 9/2021 |
| WO | WO 21/190562 A1 | 9/2021 |
| WO | WO 21/195020 | 9/2021 |
| WO | WO 21/195770 A1 | 10/2021 |
| WO | WO 21/207273 A1 | 10/2021 |
| WO | WO 21/207312 | 10/2021 |
| WO | WO 21/236809 A2 | 11/2021 |
| WO | WO 21/242545 A1 | 12/2021 |
| WO | WO 21/242776 | 12/2021 |
| WO | WO 21/247217 | 12/2021 |
| WO | WO 21/248081 A1 | 12/2021 |
| WO | WO 21/256710 A1 | 12/2021 |
| WO | WO 21/260193 A1 | 12/2021 |
| WO | WO 22/005590 A1 | 1/2022 |
| WO | WO 22/026740 A1 | 2/2022 |
| WO | WO 22/031342 A1 | 2/2022 |
| WO | WO 22/032166 A1 | 2/2022 |
| WO | WO 22/060424 A1 | 3/2022 |
| WO | WO 22/060488 A1 | 3/2022 |
| WO | WO 22/072538 | 4/2022 |
| WO | WO 22/150642 | 7/2022 |

(56) References Cited

FOREIGN PATENT DOCUMENTS

| | | |
|---|---|---|
| WO | WO 22/150644 | 7/2022 |
| WO | WO 22/164886 | 8/2022 |
| WO | WO 22/178367 | 8/2022 |
| WO | WO 22/198232 | 9/2022 |
| WO | WO 22/200412 | 9/2022 |
| WO | WO 22/200478 | 9/2022 |
| WO | WO 22/200525 | 9/2022 |
| WO | WO 22/204282 | 9/2022 |
| WO | WO 22/212918 | 10/2022 |
| WO | WO 22/226100 | 10/2022 |
| WO | WO 22/231978 | 11/2022 |
| WO | WO 22/235622 | 11/2022 |
| WO | WO 22/240741 | 11/2022 |
| WO | WO 22/241148 | 11/2022 |
| WO | WO 22/241446 | 11/2022 |
| WO | WO 22/251850 | 12/2022 |
| WO | WO 22/253867 | 12/2022 |
| WO | WO 22/258015 | 12/2022 |
| WO | WO 22/258662 | 12/2022 |
| WO | WO 22/258673 | 12/2022 |
| WO | WO 22/258678 | 12/2022 |
| WO | WO 22/258691 | 12/2022 |
| WO | WO 22/261113 | 12/2022 |
| WO | WO 22/266539 | 12/2022 |
| WO | WO 22/266540 | 12/2022 |
| WO | WO 22/268050 | 12/2022 |
| WO | WO 22/268192 | 12/2022 |
| WO | WO 23/001884 | 1/2023 |
| WO | WO 23/288252 | 1/2023 |
| WO | WO 23/288267 | 1/2023 |
| WO | WO 23/019216 | 2/2023 |
| WO | WO 23/051727 | 4/2023 |
| WO | WO 23/056969 | 4/2023 |
| WO | WO 23/061388 | 4/2023 |
| WO | WO 23/068818 A1 | 4/2023 |
| WO | WO 23/077099 A1 | 5/2023 |
| WO | WO 23/086768 | 5/2023 |
| WO | WO 23/094413 A1 | 6/2023 |
| WO | WO 23/109942 | 6/2023 |
| WO | WO 23/116880 | 6/2023 |
| WO | WO 23/125611 | 7/2023 |
| WO | WO 23/138551 | 7/2023 |
| WO | WO 23/141611 | 7/2023 |
| WO | wo 23/153759 | 8/2023 |
| WO | WO 23/163187 | 8/2023 |
| WO | WO 23/166322 | 9/2023 |
| WO | WO 23/174396 | 9/2023 |
| WO | WO 23/180533 | 9/2023 |
| WO | WO 23/183923 | 9/2023 |
| WO | WO 23/196785 | 10/2023 |
| WO | WO 23/196786 | 10/2023 |
| WO | WO 23/196996 | 10/2023 |
| WO | WO 23/198195 | 10/2023 |
| WO | WO 23/198635 | 10/2023 |
| WO | WO 23/215674 | 11/2023 |
| WO | WO 23/215740 | 11/2023 |
| WO | WO 23/227660 | 11/2023 |
| WO | WO 23/232752 | 12/2023 |
| WO | WO 24/001641 | 1/2024 |
| WO | WO 24/015830 | 1/2024 |
| WO | WO 24/026407 | 2/2024 |
| WO | WO 24/030577 | 2/2024 |
| WO | WO 24/036148 | 2/2024 |
| WO | WO 24/036329 | 2/2024 |
| WO | WO 24/040194 | 2/2024 |

OTHER PUBLICATIONS

US 11,331,347 B2, 05/2022, Yao et al. (withdrawn)
US 11,339,200 B2, 05/2022, Yao et al. (withdrawn)
US 11,732,039 B2, 08/2023, Sun et al. (withdrawn)
Liu et al. Modulation of Functional Properties of Galectin-3 by Monoclonal Antibodies Binding to the Non-Lectin Domains. Biochemistry, 1996, 35, 60-6079. (Year: 1996).*
Blanchard et al. Galectin-3 inhibitors: a patent review (2008—present). Expert Opin. Ther. Patents (2014) 24(10):1053-106. (Year: 2014).*
Linch et al. Galectin-3 inhibition using novel inhibitor GR-MD02 improves survival and immune function while reducing tumor vasculature Journal for ImmunoTherapy of Cancer 2015, 3(Suppl 2):p. 306 (Year: 2015).*
Edwards et al., The remarkable flexibility of the human antibody repertoire; isolation of over one thousand different antibodies to a single protein, BLyS. J Mol Biol. Nov. 14, 2003;334(1): 103-18. (Year: 2003).*
Lloyd et al., Modelling the human immune response: performance of a 1011 human antibody repertoire against a broad panel of therapeutically relevant antigens. Protein Eng Des Sel. Mar. 2009;22(3):159-68. (Year: 2009).*
Goel et al., Plasticity within the antigen-combining site may manifest as molecular mimicry in the humoral immune response. J Immunol. Dec. 15, 2004; 173(12):7358-67. (Year: 2004).*
Kanyavuz et al., Breaking the law: unconventional strategies for antibody diversification. Nat Rev Immunol. Jun. 2019; 19(6):355-368. (Year: 2019).*
Busby et al. Systematic comparison of monoclonal versus polyclonal antibodies for mapping histone modifications by ChIP-seq. Epigenetics & Chromatin (2016) 9:49. (Year: 2016).*
Guha et al. Cod glycopeptide with picomolar affinity to galectin-3 suppresses T-cell apoptosis and prostate cancer metastasis. PNAS Mar. 26, 2013 110 (13) 5052-5057. (Year: 2013).*
Owens RJ, Young RJ. The genetic engineering of monoclonal antibodies. J Immunol Methods. 168(2):149-165, 1994. (Year: 1994).*
Halimi H, Rigato A, Byrne D, Ferracci G, Sebban-Kreuzer C, et al. (2014) Glycan Dependence of Galectin-3 Self-Association Properties. PLoS ONE 9(11):e111836. (Year: 2014).*
Agarwal et al., Jan. 2, 2013, A Pictet-Spengler ligation for protein chemical modification, PNAS, 110(1): 46-51.
Axup et al., Oct. 2, 2012, Synthesis of site-specific antibody-drug conjugates using unnatural amino acids, PNAS 109(40):16101-16106.
Bio-techne, Feb. 7, 2018, Human galectin-3 antibody, product description, 1 p.
Blaney, et al., 2002, Traceless solid-phase organic synthesis, Chem. Rev. 102:2607-2024.
Brinkmann et al., 2017, The making of bispecific antibodies, MABS, 9(2):182-212.
Casi et al., 2012, Site-specific traceless coupling of potent cytotoxic drugs to recombinant antibodies for pharmacodelivery, JACS 134(13):5887-5892.
Chatal et al., 1985, Clinical prospective study with radioiodinated monoclonal antibodies directed against colorectal cancer, Monoclonal Antibodies for Cancer Detection and Therapy, Baldwin and Byers eds., pp. 159-180, 223-267, Academic Press.
Chothia et al., 1987, Canonical structures for the hypervariable regions of immunoglobulins, J Mol Biol, 196(4):901-917.
Chothia et al., 1989, Conformations of immunoglobulin hypervariable regions, Nature, 342:877-883.
Cortez-Retamozo et al., Apr. 15, 2004, Efficient cancer therapy with a nanobody-based conjugate, Cancer Research, 64:2853-2857.
Dawson et al., May 14, 1997, Modulation of Reactivity in Native Chemical Ligation through the Use of Thiol Additives, J. Am. Chem. Sec. 119(19):4325-4329.
Dawson et al., Nov. 4, 1994, Synthesis of proteins by native chemical ligation, Science, 266:776-779.
Ebrahim et al., Sep. 2014, Galectins in cancer: carcinogenesis, diagnosis and therapy, Annals of Translational Medicine, 2(9):88.
Fredericks et al., 2004, Identification of potent human anti-IUL-IR$_1$, antagonist antibodies, Protein Engineering, Design & Selection, 17(1):95-106.
George et al., Aug. 2020, Pulmonary fibrosis and COVID-19: the potential role for antifibrotic therapy, The Lancet, 8:207-215.
Glaser et al., Oct. 15, 1992, Dissection of the combining site in a humanized anti-tax antibody, J. Immunol. 149:2607-2614.

(56) References Cited

OTHER PUBLICATIONS

Goplen et al., Apr. 14, 2020, Tissue-resident CD8+ T cells drive age-associated chronic lung sequelae following viral pneumonia, bioRxiv preprint doi: https://doi/org/10.1101/2020.04.13.041096, 46 pp.
Gump et al., 2001, An antibody to p16INK4A recognizes a modified form of galectin-3, Hybridoma, 20(3):167-174.
Hackeng et al., Aug. 1999, Protein synthesis by native chemical ligation: Expanded scope by using straightforward methodology., Proc. Natl. Acad. Sci. USA, 96:10068-10073.
Hejesen et al., 2013, A traceless aryl-triazene linker for DNA-directed chemistry, Org Biomol Chem, 11(15):2493-2497.
Johnson et al., 2000, Kabat database and its applications: 30 years after the first variability plot, Nucleic Acids Res., 28(1):214-218.
Korndorfer et al., 2003, Crystallographic analysis of an "anticalin" with tailored specificity for fluorescein reveals high structural plasticity of the lipocalin loop region, Proteins: Structure, Function, and Bioinformatics, 53(1):121-129.
Kunik et al., 2012, Paratome: an online tool for systematic identification of antigen-binding regions in antibodies based on sequence or structure, Nucl Acids Res., 40:W521-W524.
Lam, 1997, Application of combinatorial library methods in cancer research and drug discovery, Anticancer Drug Des. 12:145-167.
Larrick et al., May 15, 1989, Rapid cloning of rearranged immunoglobulin genes from human hybridoma cells using mixed primers and the polymerase chain reactions, Biochem. Biophys. Res. Commun., 160(3):1250-1255.
Lefranc et al., 2003, IMGT unique numbering for immunoglobulin and T cell receptor variable domains and Ig superfamily V-like domains, Dev Comp Immunol. 27:55-77.
Levitt et al., 1983, Molecular dynamics of native protein I. Computer simulation of trajectories, J. Mol. Biol., 168:595-620.
Linch et al., Nov. 4, 2015, Galectin-3 inhibition using novel inhibitor GR-MD-02 improves survival and immune function while reducing tumor vasculature, Journal for Immunotherapy of Cancer, 3(Suppl 2):p. 306.
Liu et al., May 4, 2020, Neutralizing antibodies isolated by a site-directed screening have potent protection on SARS-CoV-2 infection, bioRxiv preprint doi:https//doi.org/10.1101/2020.04.02.074914, 33 pp.
Loimaranta et al., 2018, Galectin-3-binding protein: a multitask glycoprotein with innate immunity functions in viral and bacterial infections, Journal of Leukocyte Biology, 104:777-785.
MacCallum et al., 1996, Antibody-antigen interactions; contact analysis and binding site topography, J. Mol. Biol., 5:732-745.
MacKinnon et al., Mar. 1, 2012, Regulation of transforming growth factor-β1-driven lung fibrosis by galectin-3, Am J Respir Crit Care Med, 185(5):537-546.
Makabe et al., Jan. 11, 2008, Thermodynamic consequences of mutations in vernier zone residues of a humanized anti-human epidermal growth factor receptor murine antibody, 528, Journal of Biological Chemistry, 283(2):1156-1166.
Martin et al., Dec. 1989, Modeling antibody hypervariable loops; a combined algorithm, Proc Natl Acad Sci (USA), 86:9268-9272.
Martins et al., 2011, Targeting the insulin-like growth factor pathway in phabdomyosarcomas: rationale and future perspectives, Sarcoma, 2011:1-11.
Olafsen et al., 2004, Characterization of engineered anti-p185[HER-2] (scFv-$C_H$3)$_2$ antibody fragments (minibodies) for tumor targeting, Protein Eng Des Sel., 17(4):315-323.
Olsnes et al., 1982, Chimeric Toxins, Pharmac. Ther. 15:355-381.
Orlandi et al., May 1989, Cloning immunoglobulin variable domains for expression by the polymerase chain reaction, Proc. Natl. Acad. Sci. U.S.A., 86: 3833-3837.
Powers et al., 2001, Expression of single-chain Fv-Fc fusions in pichia pastoris, Journal of Immunological Methods, 251:123-135.
Rasool et al., Nov. 9-12, 2021, Novel therapeutic efficacy of galectin-3 antibody for treating Alzheimer's disease, Conference Poster Brochure, Clinical Trials on Alzheimer's Disease, Boston, MA, p. 30.
Redmond, Feb. 7, 2017, Immunotherapy plus a galectin-3 inhibitor improves anti-tumor immunity: insights from mice in a first-in-human phase I clinical trial, Earle A. Chiles Research Institute, 33 pp.
Roque et al., 2004, Antibodies and genetically engineered related molecules: production and purification, Biotechnol. Prog. 20:639-654.
Samudrala et al., 1999, Ab Initio Protein Structure Prediction Using a Combined Hierarchical Approach, Proteins, Structure, Function and Genetics Suppl., 3:194-198.
Sastry et al., 1989, Cloning of the immunological repertoire in *Escherichia coli* for generation of monoclonal catalytic antibodies: construction of a heavy chain variable region-specific cDNA library, Proc. Natl. Acad. Sci., U.S.A. 86: 5728-5732.
Shaiaby et al.,1992, Development of humanized bispecific antibodies reactive with cytotoxic lymphocytes and tumor cells overexpressing the HER2 protooncogene, J. Exp. Med. 175:217-225.
Strop et al., 2013, Location matters: site of conjugation modulates stability and pharmacokinetics of antibody drug conjugates, Chemistry and Biology, 20(2):161-167.
Sun et al., Apr. 1, 2014, Myosin Va mediates Rab8A-regulated GLUT4 vesicle exocytosis in insulin-stimulated muscle ceils, Molecular Biology of the Cell, 25:1159-1170.
Sun et al., Mar. 27, 2020, Macrophage galectin-3 enhances initimal translocation of vascular calcification in diabetes mellitus, Am J. Physiol Heart Circ Physiol, 318:H1068-H1079.
Tao et al., 2020, Galectin-3 promotes Aβ oligomerization and Aβ toxicity in a mouse model of Alzheimer's disease, Cell Death & Differentiation, 27:192-209.
Tempest et al., Mar. 1991, Reshaping a human monoclonal antibody to inhibit human respiratory syncytial virus infection in vivo, Biotechnology 9:266-271.
Thijssen et al., Oct. 15, 2007, Galectins in the tumor endothelium: opportunities for combined cancer therapy, Blood, 119(0):2819-2827.
Thomas et al., Sep. 12, 2018, Galectin-3 mediated glial crosstalk drives oligodendrocyte differention and (re)myelination, Frontiers in Cellular Neuroscience, 12(12):1-16.
Tunduguru et al., Sep. 25, 2017, The actin-related p41ARC subunit contributes to p21-activated kinase-1 (PAK1)-mediated glucose uptake into skeletal muscle cells, J. Biol. Chem., 292(46):19034-19043.
Varsateh et al., 2021, Imaging atherosclerotic plaques by targeting galectin-3 and activiate macrophages using ($^{89}$Zr)-DFO-Galectin3-F(ab')$_2$ mAb, Theranostics, 11(4):1864-1876.
Vuong et al., Apr. 1, 2019, An orally active galectin-3 antagonist inhibits lung adenocarcinoma growth and augments response to PD-L1 blockade, Cancer Research, 79(7):1480-1492.
Wu et al., Mar. 3, 2009, Site-specific chemical modification of recombinant proteins produced in mammalian cells by using the genetically encoded aldehyde tag, PNAS, 106(9):3000-3005.
Wu, et al. 2006, Building complex glycopeptides: Development of a cysteine-free native chemical ligation protocol, Angew. Chem. Int. Ed. 45:4116-4125.
Xiong et al., 2020, Transcriptomic characteristics of bronchoalveolar lavage fluid and peripheral blood mononuclear cells in COVID-19 patients, Emerging Microbes & Infections, 9:761-770.
Yip et al., Jan. 27, 2017, Galectin-3 released in response to traumatic brain injury acts as an alarmin orchestrating brain immune response and promoting neurodegeneration, Sci. Rep. 27, 13 pp.
Zapata et al., 1995, Engineering linear F(ab')$_2$ fragments for efficient production in *Escherichia coli* and enhanced antiproliferative activity, Protein Eng., 8(10):1057-1062.
Holliger, P et al. "Diabodies": small bivalent and bispecific antibody fragments. PNAS. Jul. 1993. Vo. 90, p. 6444-6448.
Swartz, MA et al. Tumor Microenvironment Complexity: Emerging Roles in Cancer Therapy. Cancer Research. Mar. 2012. 72(10);2473-80.
Baines MG & Thorpe R. Purification of Immunoglobulin G (IgG). Methods in Mol. Biol. 1992. vol. 10.
Bird RE et al. Single-Chain Antigen-Binding Proteins. Science. Oct. 1988; 242(4877):423-6.

(56) References Cited

OTHER PUBLICATIONS

Carter PJ. Potent antibody therapeutics by design. Nat. Rev. Immunol. May 2006; 6(5):343-57.
Cedeno-Laurent, F et al. Galectins and their Ligands: Negative Regulators of Anti-Tumor Immunity. Glycoconjugate Journal. Dec. 2012, vol. 29, No. 8-9, pp. 619-625.
Green LL et al. Antigen-specific human monoclonal antibodies from mice engineered with human Ig heavy and light chain YACs. Nat. Genet. May 1994; 7(1):13-21.
Holliger, P et al. Engineered antibody fragments and the rise of single domains. Nat. Biotechnol. Sep. 2005; 23(9):1126-36.
Huang, Y-H et al. CEACAM1 regulates TIM-3-mediated tolerance and exhaustion. Nature. Oct. 2014; 517(7534):386-90.
Huston, JS et al. Protein engineering of antibody binding sites: Recovery of specific activity in an anti-digoxin single-chain Fv analogue produced in *Escherichia coli*. PNAS. Aug. 1988. vol. 85, p. 5879-5883.
International Preliminary Report on Patentability dated Jan. 28, 2020 in Application No. PCT/US2018/043513.
International Search Report and Written Opinion dated Oct. 25, 2018 in Application No. PCT/US2018/043513.
Kang, H et al. Imaging-based tumor treatment response evaluation: Review of conventional, new and emerging concepts. Korean J. Radiol. Jun. 2018; 13(4):371-390.
Köhler, G & Milstein, C. Continuous cultures of fused cells secreting antibody of predefined specificity. Nature. Aug. 1975; 256:495-497.
Leitner, J et al. TIM-3 Does Not Act as a Receptor for Galectin-9. PLoS Pathog. Mar. 2013. 9(3):e1003253.
Leung, SO et al. Chimerization of LL2, a rapidly internalizing antibody specific for B cell lymphoma. Hybridoma. Dec. 1994; 13(6):469-76.
Li, P et al. Design and Synthesis of Paclitaxel Conjugated with an ErbB2-Recognizing Peptide, EC-1. Biopolymers. Nov. 2007; 87(4):225-30.
Liu, D-Z et al. Synthesis of 2'-paclitaxel methyl 2-glucopyranosyl succinate for specific targeted delivery to cancer cells. Bioorg. Med. Chem. Lett. Feb. 2007; 17(3):617-20.
Lonberg, N et al. Antigen-specific human antibodies from mice comprising four distinct genetic modifications. Nature. Apr. 1994; 368(6474):856-9.
McCafferty, J et al. Phage antibodies: filamentous phage displaying antibody variable domains. Nature. Dec. 1990; 348(6301):552-4.
Takaya, T et al. Importance of dissolution process on systemic availability of drugs delivered by colon delivery system. J Control Release. Jan. 1998; 50(1-3):111-22.
Tomlinson I & Holliger P. Methods for Generating Multivalent and Bispecific Antibody Fragments. Methods Enzymol. 2000; 326:461-79.
Ward, ES et al. Binding activities of a repertoire of single immunoglobulin variable domains secreted from *Escherichia coli*. Nature. Oct. 1989; 341:544-546.
Zhu, C et al. The Tim-3 Ligand Galectin-9 Negatively Regulates T Help Type 1 Immunity. Nature Immunology. Nov. 13, 2005, vol. 6, No. 12, pp. 1245-1252.
Ajjan et al., 2006, Coagulation and atherothrombotic disease, Atherosclerosis, 186:240-259.
Andrade et al., 2009, Rechallenge in drug-induced liver injury: the attractive hazard, Expert Opin. Drug Saf., 8(6):709-714.
Ashraf et al., Jun. 2018, Investigation of Gal-3 expression pattern in serum and cerebrospinal fluid of patients suffering from neurodegenerative disorders, Frontiers in Neuroscience, 12:Article 430, 8 pp.
Banks et al., Mar. 2007, Outcomes validity and reliability of the modified Rankin scale; implications for stroke clinical trials, Stroke, 38:1091-1096.
Barua et al., 2010, Effects of cigarette smoke exposure on clot dynamics and fibrin structure,: an ex vivo investigation, Arterioscler Thromb Vasc Biol, 30:75-79.

Benjamin et al., Mar. 7, 2017, Heart disease and stroke statistics-2017 update: a report from the American Heart Association, Circulation, 135:e146-e603.
Boza-Serrano et al., Apr. 20, 2019, Galectin-3, a novel endogenous TREM2 ligand, detrimentally regulates inflammatory response in Alzheimer's disease, Acta Neuropathologica, 23 pp.
Brott et al., Jul. 1989, Measurements of acute cerebral infarction: a clinical examination scale, Stroke, 20(7):864-870.
Burguillos et al., Mar. 10, 2015 Microglia-secreted galectin-3 acts as a toll-like receptor 4 ligand and contributes to microglial activation, Cell Reports, 10:1626-1638.
Carter et al., Dec. 2007, Heritability of clot formation, morphology, and lysis: the EuroCLOT study, Arterioscler Thromb Vasc Biol, 27:2783-2789.
Centers for Disease Control and Prevention, 2015, Report to Congress on traumatic brain injury in the United States, epidemiology and rehabilitation, National Center for injury Prevention and Control: Division of Unintentional Injury Prevention, Atlanta, GA, 72 pp.
Chistiakov et al., 2017, The role of monocytosis and neutrophilia in atherosclerosis, J. Cell. Mol. Med, XX(X):1-17.
Collet et al., Nov. 2006, Altered fibrin architecture is associated with hypofribinolysis and premature coronary atherothrombosis, Arterioscler Thromb Vasc Biol, 26:2567-2573.
Corrado et al., 2010, An update on the role of markers of inflammation in atherosclerosis, Journal of Atherosclerosis and Thrombosis, 17(1):1-11.
De Pascalis et al., 2002, Grafting of abbreviated complementarity determining regions containing specificity determining residues essential for ligan contact to engineer a less immunogenic humanized monoclonal antibody, Journal of Immunology, 169:3076-3084.
Donkor, 2018, Stroke in the 21$^{st}$ century: a snapshot of the burden, epidemiology, and quality of life, Stroke Research and Treatment, vol. 2018, article ID 3238165, 10 pp.
Dunn et al., 2005, The influence of type 2 diabetes on fibrin structure and function, Diabetologia, 48:1198-1206.
Dunn et al., 2006, Molecular mechanisms involved in the resistance of fibrin to clot lysis by plasmin in subjects with type 2 diabetes mellitus, Diabetologia, 49:1071-1080.
Fang et al., Sep. 2010, Trends in thrombolytic use for ischemic stroke in the United States, Journal of Hospital Medicine, 5(7):406-409.
Fatkhullina et al., 2016, The role of cytokines in the development of atherosclerosis, Biochemistry (Moscow), 81(11):1358-1370.
Freynhofer et al., 2012, The role of platelets in athero-thrombotic events. Current Pharmaceutical Design, 18:5197-5214.
Fugl-Meyer et al., 1975, The post-stroke hemiplegic patient, Scand J. Rehab Med, 7:13-31.
Go et al., Jan. 21, 2014, Heart disease and stroke statistics—2014 update: a report from the American Heart Association, Circulation, 129:e28-e292.
Goldstein et al., Jun. 1989, Interrater reliability of the NIH stroke scale, Arch Neurol, 46:660-662.
Goulay et al., Nov. 28, 2019, From stroke to dementia: a comprehensive review exposing tight interactions between stroke and amyioid-β formation, Translational Stroke Research, 14 pp.
Green et al., 2005, Free radical trapping as a therapeutic approach to neuroprotection in stroke; experimental and clinical studies with NXY-059 and free radical scavengers, Current Drug Targets: CNS & Neurological Disorders, 4(2):109-118.
Hachinski et al., Sep. 2006, National Institute of Neurological Disorders and Stroke—Canadian Stroke Network Vascular Cognitive Impairment Harmonization Standards, Stroke, pp. 2220-2241.
Hunt, 2010 Mitochondrial and immunoaiiergic injury increase risk of positive drug rechallenge after drug-induced liver injury: a systematic review, Hepatology, 52(6):2216-2222.
Inoue et al., 2021, Current management and therapeutic strategies for cerebral amyloid angiopathy, International Journal of Molecular Sciences, 22:3869.
Jin et al., 2013 Spatial and temporal expression, and statin responsiveness of galectin-1 and galectin-3 in murine atherosclerosis, Korean Circulation Journal, pp. 223-230.

(56) References Cited

OTHER PUBLICATIONS

Khan et al., 2014, Adjustable Locks and Flexible Keys: Plasticity of Epitope-Paratope Interactions in Germline Antibodies, J. Immunol. 192:5398-5405.

Leander et al., 2012, Impaired fibrinolytic capacity and increased fibrin formation associate with myocardial infarction, Blood Coagulation, Fibrinolysis and Cellular Haemostasis, Thrombosis and Haemostasis: 107(6):1092-1100.

Lee et al., 2013, Spatial and temporal expression, and statue responsiveness of galectin-1 and galectin-3 in murine atherosclerosis, Korean Circulation Journal, 43:223-230.

Liu et al., Jul. 21, 2020, Association of the total white blood cell, neutrophils, and monocytes count with the presence, severity, and types of carotid atherosclerotic plaque, Frontiers in Medicine, 7:Article 313, 10 pp.

Lu et al., 2017, Modified citrus pectin inhibits galectin-3 function to reduce atherosclerotic lesions in apoE-deficient mice, Molecular Medicine Reports, 16:647-653.

Madrigal-Matute, 2014, Galectin-3 a biomarker linking oxidative stress and inflammation with the clinical outcomes of patients with atherothrombosis, Journal of the American Heart Association, 114:1-13.

Mariuzza et al., 1987, The Structural Basis of Antigen-Antibody Recognition Annu. Rev. Biophys. Biphys. Chem., 16:139-159.

Mauris et al., 2014, Molecular basis for MMP9 induction and disruption of epithelial cell-cell contacts by galectin-3, Journal of Cell Science, 127:3141-3148.

Mazurek et al., Oct. 1, 2011, A galectin-3 sequence polymorphism confers TRAIL sensitivity to human breast cancer cells, Cancer, 117(19):4375-4380.

McKee, 2014, Military-related traumatic brain injury and neurodegeneration, Alzheimer's & Dementia, 10:S242-S253.

Mehndiratta et al., Apr. 2012, Cerebral amyloid angiopathy-associated intracerebral hemorrhage: pathology and management, Neurosurg Focus, 32(4):E7, 14 pp.

Mills et al., 2002, Altered fibrin clot structure in the healthy relatives of patients with premature coronary artery disease, Circulation, 106:1938-1942.

Murphy et al., Dec. 2009, Plasticity during stroke recovery: from synapse to behavior, Nature Reviews, 10:861-872.

Nachtigal et al., May 1998, Galectin-3 expression in human atherosclerotic lesions, American Journal of Pathology, 152(5):1199-1208.

Nangia-Makker et al., 2010, Cleavage of galectin-3 by matrix metalloproteases induces angiogenesis in breast cancer, Int. J. Cancer, 127:2530-2541.

Nangia-Makker et al., Dec. 15, 2007, Galectin-3 cleavage: a novel surrogate marker for matrix metalloproteinase activity in growing breast cancers, Cancer Res., 67(24):11760-11768.

Nasreddine et al., Apr. 2005, The Montreal cognitive assessment, MoCA: a brief screening tool for mild cognitive impairment, JAGS, 53(4):695-699.

Nishikawa et al., 2018, Possible role of inflammation and galectin-3 in brain injury after subarachnoid hemorrhage, Brain Sci., 8:30, 11 pp.

O'Collins e al., 2006, 1,026 experimental treatments in acute stroke 59:467-477.

Ochieng et al., 1998, Modulation of the biological functions of gelactin-3 by matrix metalloproteinases, Biochimica et Biophysica Acta, 1379:97-106.

Osmancik et al., 2012, High leukocyte count and interleukin-10 predict high on-treatment-platelet-reactivity in patients treated with clopidogrel, J. Thromb Thrombolysis, 33:340-354.

Page et al., Jun. 2012, Clinically important differences for the upper-extremity Fugl-Meyer scale in people with minimal to moderate impairment due to chronic stroke, Physical Therapy, 92(6):791-798.

Papaspyridonos et al., 2008, Galectin-3 is an amplifier of inflammation in atherosclerotic plaque progression through macrophage activation and monocyte chemoattraction, Arterioscler Thromb Vasc Biol., 28:433-440.

Papay et al., 2009, Drug-induced liver injury following positive drug rechallenge, Regulatory Toxicology and Pharmacology, 54:84-90.

Paul et al., Aug. 6, 2007, Fibrin deposition accelerates neurovascular damage and neuroinflammation in mouse models of Alzheimer's disease, Journal of Experimental Medicine, 204(8):1999-2008.

Poosarla et al., 2017, Computational De Novo Design of Antibodies Binding to a Peptide With High Affinity, Biotech. Bioeng. 114(6):1331-1342.

Powers et al., 2018, 2018 guidelines for the early management of patients with acute ischemic stroke, Stroke, 49:046-99.

Pulgdellivol et al., Jun. 2020, Sialylation and galectin-3 in microglia-mediated neuroinflammation and neurodegeneration, Frontiers in Cellular Neuroscience, 14:Article 162, 11 pp.

Reijmer et al., May 6, 2015, Ischemic brain injury in cerebral amyloid angiopathy, Journal of Cerebral Blood Flow & Metabolism, 10 pp.

Rodrigues et al., 2018, The Edinburgh CT and genetic diagnostic criteria for lobar intracerebral haemorrhage associated with cerebral amyloid angiopathy: model development and diagnostic test accuracy study, Lancet Neurol, 17:232-240.

Sanford et al., Jul. 1993, Reliability of the Fugl-Meyer assessment for testing motor performance in patients following stroke, Physical Therapy, 73(7):447-454.

Satoh et al., 2011, Galectin-3 expression in delayed neuronal death of hippocampal CA 1 following transient forebrain ischemia, and its inhibition by hypothermia, Brain Research, 1382:266-274.

Scott et al., 2004, Genetic and environment determinants of fibrin structure and function: relevance to clinical disease, Arterioscler Thromb Vasc Biol, 24:1558-1566.

Shan et al., 2014, A new panel of blood biomarkers for the diagnosis of mild traumatic brain injury/concussion in adults, Journal of Neurotrauma, 30 pp.

Shen et al., 2016, The change of plasma galectin-3 concentrations after traumatic brain injury, Clinica Chimica Acta, 456:75-80.

Toglia et al., May 2011, The mini-mental state examination and Montreal cognitive assessment in persons with mild subacute stroke: relationship to functional outcome, Arch Phys Med Rehabil, 92:792-798.

Undas et al., 2007, Altered fibrin clot structure in patients with advanced coronary artery disease: a role of c-reactive protein, lipoprotein(a) and homocysteine, J Thromb Haemost, 5:1988-1990.

Undas et al., 2008, Altered fibrin clot properties in patients on long-term haemodialysis: relation to cardiovascular mortality, 23:2010-2015.

Undas et al., 2008, Reduced clot permeability and susceptibility to lysis in patients with acute coronary syndrome: effects of inflammation and oxidative stress, Atherosclerosis, 196:551-557.

Van Swieten et al., May 1988, Interobserver agreement for the assessment of handicap in stroke patients, Stroke, 19(5):604-697.

Veerbeek et al., Feb. 2014, What is the evidence for physical therapy poststroke? A systematic review and meta-analysis, PLOS One, 9(2):e87987.

Virani et al., Mar. 3, 2020, Heart disease and stroke statistics-2020 update: a report from the American Heart Association, Circulation, 141:e139-e596.

Viswanathan et al., 2011, Cerebral amyloid angiopathy in the elderly, Ann Neurol, 70:871-880.

Wang et al., 2013, Elevated galectin-3 levels in the serum of patients with Alzheimer's disease, American Journal of Alzheimer's Disease & Other Dementias, 4 pp.

Wang et al., Apr. 19, 2021, Galectin-3 mediated inflammatory response contributes to neurological recovery by QiShenYiQi in subacute stroke model, Frontiers in Pharmacology; 12:Article 588587, 16 pp.

Wang et al., Mar. 12, 2020, A human monoclonal antibody blocking SARS-CoV-2 infections, bioRxiv, https://biorxiv.org/content/10.1101/2020.03.11.987958v1, 24 pp.

(56) References Cited

OTHER PUBLICATIONS

Weisel et al., Jan. 10, 2013, Mechanisms of fibrin polymerization and clinical implications, Blood, 31 pp.
Yan et al., 2009, Galectin-3 mediates post-ischemic tissue remodeling, Brain Research, 1288:116-124.
Yip et al., 2017, Galectin-3 released in response to traumatic brain injury acts as an alarmin orchestrating brain immune response and promoting neurodegeneration, Scientific Reports, 7:41689, 13 pp.
Yoo et al., 2008, Undernutrition as a predictor of poor clinical outcomes in acute ischemic stroke patients, Arch Neurol, 61(1):39-43.
International Search Report and Written Opinion dated Aug. 6, 2020 in Application No. PCT/US20/15692.
Office action dated Dec. 9, 2021 in U.S. Appl. No. 17/384,542.
International Search Report and Written Opinion dated Apr. 14, 2021 in Application No. PCT/US20/63134.
International Search Report and Written Opinion dated Jan. 6, 2022 in Application No. PCT/US21/034096.
International Search Report and Written Opinion dated May 19, 2021 in Application No. PCT/US21/13136.
Balan et al., Dec. 15, 2008, Racial disparity in breast cancer and functional germ line mutation in galectin-3 (rs4644): a pilot study, Cancer Res. 68(24)10045-10050.
Bio-techne, 2022, Human galectin-3 antibody, product details, 7 pp.
Supplement to Bio-techne Reference Submission Regarding MAB1154, 2pp.
Inufusa et al., 2001, Role of galectin-3 in adenocarcimona liver metastasis, International Journal of Oncology, 19(5);913-991.
Ngiow et al., 2011, Anti-TIM3 antibody promotes T cell IFN-γ-mediated antitumor immunity and suppresses established tumors, Cancer Research, 71(10):35403551.
Notice of Reasons for Refusal dated Sep. 6, 2022 in Japanese patent application No. 2020-527838.
International Search Report and Written Opinion dated Sep. 13, 2022 in Application No. PCT/US2022/026005.
International Search Report and Written Opinion dated Nov. 15, 2022 in Application No. PCT/US22/32527.
International Search Report and Written Opinion dated Nov. 30, 2022 in Application No. PCT/US22/073694.
Glinskii et al. Mechanical entrapment is insufficient and intercellular adhesion is essential for metastatic cell arrest in distant organs. Neoplasia. May 2005; 7(5), 522-527.
Ngiow et al., Anti-TIM3 Antibody Promotes T Cell IFN-g-Mediated Antitumor Immunity and Suppresses Established Tumors. Cancer Research. May 2011; 71(10), 3540-3551.
Xu et al., Recent developments in galectin-3 and its inhibitors. Chinese Journal of Biochemical Pharmaceutics. Dec. 2011; 32(5), 417-420.
Decision of Rejection dated Mar. 15, 2023 in Japanese patent application No. 2020-527838.
First Office Action and Search Report in Chinese Application No. 2018800616946.6.
Fichorova et al., Jan. 8, 2016, Trichomonas vaginalis lipopophosphoglycan exploits binding to galectin-1 and -3 to modulate epithelial immunity, J. Biol. Chem, 291 (2):998-1013.
Second Office Action and Search Report dated Jul. 31, 2023 in Chinese Application No. 2018800616946.6.
First Office Action and Search Report dated Jun. 15, 2023 in Chinese Application No. 202080025814.4.
First Office Action dated Jul. 6, 2023 in Chinese Application No. 202211069802.9.
European Search Reporot dated Nov. 29, 2022 in patent application No. 20749738.9, 21 pp.
Office Action dated Jun. 23, 2023 in U.S. Appl. No. 17/303,268.
Office action dated Jul. 6, 2023 in U.S. Appl. No. 17/812,159.
Abcam, Sep. 27, 2023, Anti-Galectin 3 antibody ab2785, product data sheet, 7 pp.
Almagro JC, Fransson J. Humanization of antibodies. Front Biosci. Jan. 1, 2008;13:1619-33. (Year: 2008).
Kussie et al. A single engineered amino acid substitution changes antibody fine specificity.J Immunol. Jan. 1, 1994;152(1):146-52. (Year: 1994).
Li et al., Nov. 3, 2016, Hematopoietic-derived galectin-3 causes cellular and systemic insulin resistance, Cell, 167(4):973-984.
Razpotnik R, Novak N, Gurin Serbec V, Rajcevic U. Targeting Malignant Brain Tumors with Antibodies. Front Immunol. Sep. 25, 2017;8:1181. (Year: 2017).
Shi et al., 2022, Anti-galectin-3 antibodies induce skin vascular inflammation via promoting local production of IL-1β in systemic lupus erythematosus, Int. Immunopharm., 112:109197.
Office Action dated Oct. 3, 2023 in U.S. Appl. No. 17/303,268.
Examination Report dated Oct. 27, 2023 in Canadian patent application No. 3070446.
Decision to grant patent in Japanese patent application No. 2020-527838.
Herold et al., Sep. 2017, Determinants of the assembly and function of antibody variable domains, Scientific Reports, 7:12276, 17 pp.
Kranz et al., Sep. 1981, Restricted reassociation of heavy and light chains from hapten-specific monoclonal antibodies, PNAS, 78(9)5807-5811.
Third Office Action dated Dec. 21, 2023 in Chinese Application No. 2018800616946.6.
Office action dated Jan. 5, 2024 in U.S. Appl. No. 17/813,578.
Requisition by the examiner dated Oct. 19, 2023 in Canadian patent application No. 3,127,113.
Examination Report dated Dec. 12, 2023 in patent application No. 20749738.9.
Notice of Reasons for Refusal dated Jan. 16, 2024 in Japanese patent application No. 2021-544701.
Requisition by the examiner dated Oct. 18, 2023 in Canadian patent application No. 3,164,060.
Extended supplemental European search report dated Nov. 17, 2023 in application No. 20896254.8.
Office action dated Jan. 24, 2024 in U.S. Appl. No. 17/812,159.
Requsition by the examiner dated Oct. 20, 2023 in Canadian patent application No. 3,166,552.
Office action dated Feb. 2, 2024 in U.S. Appl. No. 17/834,703.
International Search Report and Written Opinion dated Nov. 30, 2022 in Application No. PCT/US22/073594.
Cerel et al., 2019, Inhibition of sialidase activity and galectin binding reduced xengeneic neutrophil-endothelial adhesion, American Journal of Transplantation, 19(Supplement 3), abstract only, 2 pp.
Chen et al., Jun. 15, 1995, Enhancement and destruction of antibody function by somatic mutation: unequal occurrence is controlled by V gene combinatorial association, EMBO J., 14(12)2784-2794.
Koenig et al. Jan. 5, 2017, Mutational landscape of antibody variable domains reveals a switch modulating the interdomain conformational dynamics and antigen binding, PNAS, 114(4):E486-E495.
Linden et al., 2013, The role of galectin-3 in phagocytosis of Candida albicans and Candida parapsilosis by human neutrophils, Cellular Microbiology, 15(7):1127-1142.
Priglinger et al., Jul. 29, 2013, Galectin-3 induced clustering of CD147 and integrin-beta 1 transmembrane glycoprotein receptors on the RPE cell surface. Plos One, Article e70011, abstract only.
Shi et al., 2019, 032-II-1b is essential for anti-galectin3 antibody induced cutaneous vasculitis in systems lupus erythematosus, Journal of Investigative Dermatology, 2019 Meeting Abstract Supplement, 2 pp.
Volarevic et al., 2015, Gal-3 regulates the capacity of dendritic cells to promote NKT-cell-induced liver injury, European Journal of Immunlogy, 45:531-543.
Examination Report No. 1 dated Jun. 21, 2024 in Australian patent application No. 2018308088.
Notice of Reasons for Refusal dated Jun. 25, 2024 in Japanese patent application No. 2023-118382.
Translation of Decision of Rejection Apr. 12, 2024 in Chinese patent application No. 2018800616946.6.
Translation of decision of rejection received Dec. 4, 2023 in Chinese Application No. 202080025814.4.

(56) References Cited

OTHER PUBLICATIONS

Translation of Second office action received May 23, 2024 in Chinese Application No. 202080025814.4.
Translation of second office action received Nov. 30, 2023 in Chinese Application No. 202211069802.9.
Translation of decision of rejection received May 21, 2024 in Chinese Application No. 2022113436441.
Partial supplemental European search report dated Aug. 17, 2023 in application No. 20896254.8.
Office Action dated Apr. 9, 2024 in U.S. Appl. No. 17/303,268.
Partial supplemental European search report dated Jun. 11, 2024 in application No. 21812182.0.
Office action dated Jun. 20, 2024 in U.S. Appl. No. 17/812,159.
Translation of First Office Action dated Apr. 28, 2024 in Chinese patent application No. 202180022171.2.
International Search Report and Written Opinion dated Mar. 14, 2024 in Application No. PCT/US23/75268.

\* cited by examiner

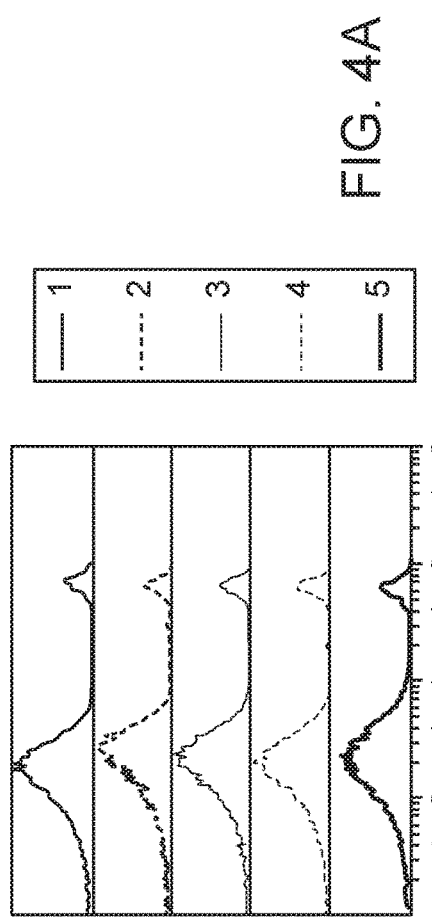
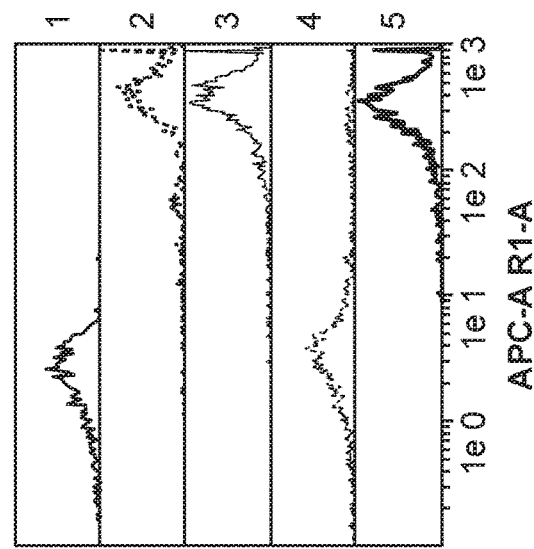
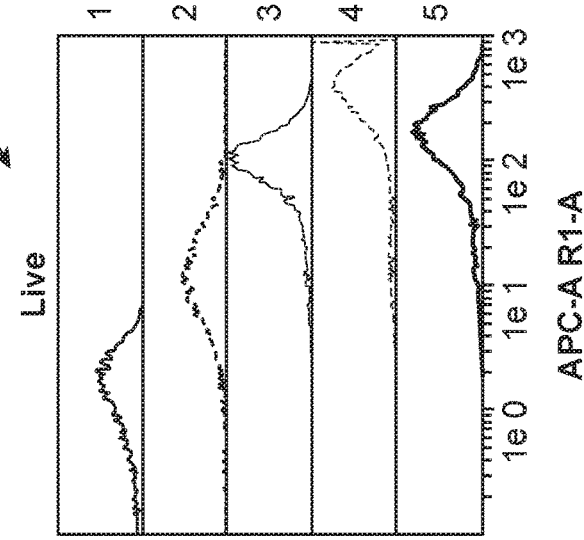
FIG. 4A
FIG. 4B
FIG. 4C peptide_1 ADNFSLHDALSGSGNPNPQG (SEQ ID NO: 27)
peptide_2 SGSGNPNPQGWPGAWGNQPA (SEQ ID NO: 28)
peptide_3 WPGAWGNQPAGAGGYPGASY (SEQ ID NO: 29)
peptide_4 GAGGYPGASYPGAYPGQAPP (SEQ ID NO: 30)
peptide_5 PGAYPGQAPPGAYPGQAPPG (SEQ ID NO: 5)
peptide_6 GAYPGQAPPGAYPGAPGAYP (SEQ ID NO: 6)
peptide_7 AYPGAPGAYPGAPAPGVYPG (SEQ ID NO: 31)
peptide_8 GAPAPGVYPGPPSGPGAYPS (SEQ ID NO: 32)
peptide_9 PPSGPGAYPSSGQPSATGAY (SEQ ID NO: 33)
peptide_10 SGQPSATGAYPATGPYGAPA (SEQ ID NO: 34)
peptide_11 PATGPYGAPAGPLIVPYNLP (SEQ ID NO: 35)
peptide_12 GPLIVPYNLPLPGGVVPRML (SEQ ID NO: 36)
peptide_13 LPGGVVPRMLITILGTVKPN (SEQ ID NO: 37)
peptide_14 ITILGTVKPNANRIALDFQR (SEQ ID NO: 38)
peptide_15 ANRIALDFQRGNDVAFHFNP (SEQ ID NO: 39)
peptide_16 GNDVAFHFNPRFNENNRRVI (SEQ ID NO: 40)
peptide_17 RFNENNRRVIVCNTKLDNNW (SEQ ID NO: 41)
peptide_18 VCNTKLDNNWGREERQSVFP (SEQ ID NO: 42)
peptide_19 GREERQSVFPFESGKPFKIQ (SEQ ID NO: 43)
peptide_20 FESGKPFKIQVLVEPDHFKV (SEQ ID NO: 44)
peptide_21 VLVEPDHFKVAVNDAHLLQY (SEQ ID NO: 45)
peptide_22 AVNDAHLLQYNHRVKKLNEI (SEQ ID NO: 46)
peptide_23 NHRVKKLNEISKLGISGDID (SEQ ID NO: 47)
peptide_24 SKLGISGDIDLTSASYTMI (SEQ ID NO: 48)

FIG. 11A

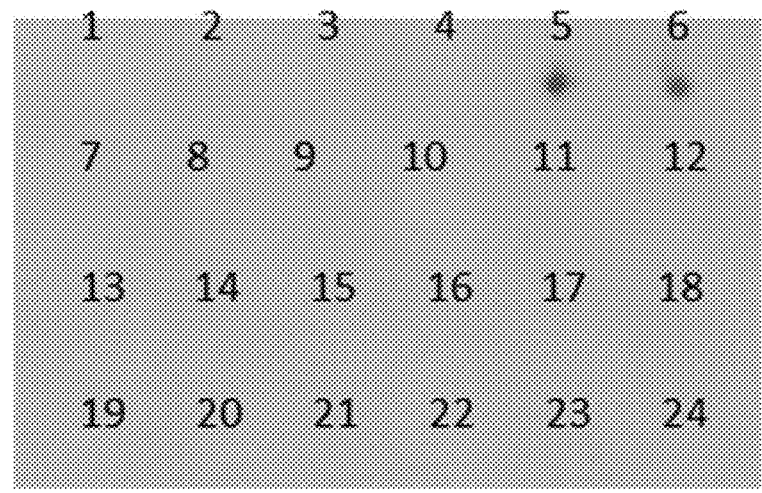

FIG. 11B

Gal3 peptides

Pep-1 PGAYPGQAPP (SEQ ID NO: 49)
Pep-2 GQAPPGAYPG (SEQ ID NO: 8)
Pep-3 GAYPGQAPPGA (SEQ ID NO: 50)
Pep-4 APPGAYPGAP (SEQ ID NO: 51)
Pep-5 YPGAPGAYP (SEQ ID NO: 52)
Pep-6 APPGAY (SEQ ID NO: 53)
Pep-7 GAYPGQ (SEQ ID NO: 54)
Pep-8 PGQAPP (SEQ ID NO: 55)

TREATING CANCER BY BLOCKING THE INTERACTION OF TIM-3 AND ITS LIGAND

RELATED APPLICATION

This application is a U.S. National Phase of PCT International App. No. PCT/US2018/043513, filed on Jul. 24, 2018, designating the United States of America and published in the English language, which claims the benefit of U.S. Provisional Application No. 62/536,886, filed on Jul. 25, 2017. Said provisional application is herein incorporated by reference in its entirety for all purposes.

REFERENCE TO SEQUENCE LISTING

The present application is being filed along with a Sequence Listing in electronic format. The Sequence Listing is provided as a file entitled SeqListingIMMUTOO2NP.TXT created Jan. 23, 2020, which is 28,423 bytes in size. The information in the electronic format of the Sequence Listing is incorporated herein by reference in its entirety.

BACKGROUND OF THE INVENTION

Human cancers harbor numerous genetic and epigenetic alterations, generating neoantigens potentially recognizable by the immune system. Although endogenous immune response to cancer is observed in preclinical models and patients, the response is ineffective and established cancers are often viewed as "self" and tolerated by the immune system. In addition, tumors may exploit several distinct mechanisms to actively suppress the host immune response. Among these mechanisms, immune checkpoints, involving various negative regulators of the immune system, which normally terminate immune responses to mitigate collateral tissue damage, can be used by tumors to evade immune destruction.

T-cell immunoglobulin and mucin-domain containing-3 (TIM-3) is known as one of such negative regulators of T cell activation, however the mechanism of TIM-3 suppression of T cell activation is largely unknown. Earlier efforts have been exerted toward identifying ligands for TIM-3 in this regulation, however the data have been inconsistent and unreliable. For example, it was reported in 2005 that galectin-9 (Gal9) can bind to TIM-3 (Zhu et al., Nature Immunology 6, 1245); however, later reports showed that the interaction of TIM-3 and Gal9 is non-specific in nature (Leitner et al. PLoS Pathog 9(3): e1003253). CEACAM1 was also reported as a TIM-3 ligand to regulate T cell tolerance and exhaustion (Huang et al. Nature 517, 386). However, Huang's results are inconsistent with inventors' own data which show that TIM-3 does not bind to CEACAM1 (see below).

BRIEF SUMMARY OF THE INVENTION

This invention is based on the surprising discovery that TIM-3 interacts with a novel ligand galectin-3 (Gal3) and the interaction leads to suppression of immune response, e.g., T cell activation. The invention provides novel compositions and methods that block the interaction, activate immune response, and thus cure cancer.

In some embodiments, the disclosure provides a method of activating immune response in a patient comprising administering to the patient a Gal3:TIM-3 inhibitor that interferes with the interaction between the Gal3 and TIM-3 in the patient, where said inhibitor is administered in an amount sufficient to activate immune response. In some embodiments, the patient hosts a cancer and the interaction between Gal3 and TIM-3 occurs in a tumor microenvironment. In some embodiments, the activation of the immune response decreases the cancer load of the patient. In some embodiments, the TIM-3 is present on the immune cells. In some embodiments, the patient hosts a cancer and Gal3 is overexpressed in the tumor microenvironment and the Gal3:TIM-3 inhibitor is administered in an amount sufficient to decrease the cancer load of the patient. In some embodiments, the cancer comprises cancer cells overexpressing Gal3 on their surface. In some embodiments, the immune cells on which the TIM-3 is expressed are T cells and/or NK cells.

In some embodiments, the disclosure provides a method of activating T-cells in a patient hosting a cancer comprising cells in a tumor microenvironment, wherein the cells overexpress Gal3, the method comprising administering to the patient a Gal3:TIM-3 inhibitor that interferes with the interaction between the Gal3 and TIM-3 on the T-cells where said inhibitor is administered in an amount sufficient to decrease the cancer load of the patient by activation of the T-cells.

Optionally, the cells in the tumor microenvironment comprises cancer cells. Optionally the cells in the tumor microenvironment comprises tumor-associated macrophages (TAMs), e.g., M2 TAMs.

In some embodiments, the Gal3:TIM-3 inhibitor binds to TIM-3. In some embodiments, the Gal3:TIM-3 inhibitor binds to Gal3.

In some embodiments, the disclosure provides a method for determining if a patient's cancer is suitable for treatment with a Gal3:TIM-3 inhibitor, said method comprising: combining cells obtained from a tumor microenvironment of a known type from a patient with an antibody specific for the Gal3; determining the level of Gal3 on the surface of the primary cancer cells in the sample; comparing the level of Gal3 on the surface of the cells with a first threshold activity value of Gal3; and determining the patient's cancer as suitable for treatment with a Gal3:TIM-3 inhibitor if the level of Gal3 on the surface of the primary cancer cells is higher than the first threshold activity value.

In some embodiments, the first threshold activity value of Gal3 is derived from a cohort of at least 100 test individuals with the same type of cancer as the patient sample. In some embodiments, the first threshold activity value of Gal3 is based on the average, mean, or median level of Gal3 on the surface of cells of similar tissue type from healthy individuals.

In some embodiments, this disclosure provides a sterile solution that is able to interfere with the interaction between the Gal3 and TIM-3 on T-cells in a cancer patient, where the solution comprises between 10 µg and 100 mg of antibody per kilogram of patient body weight in a solution of 100 ml suitable for intravenous delivery over a 1-4 hour period, wherein the antibody can interfere with the interaction between the Gal3 and TIM-3 on the T-cells. In some embodiments, the sterile solution further comprises one or more other checkpoint inhibitor antibodies. In some embodiments, the one of more other checkpoint inhibitor antibodies is selected from the group consisting of anti PD-1 and anti CTLA-4 antibodies.

In some embodiments, this disclosure provides a method of producing an anti-Gal3 antibody that can interfere with the interaction between Gal3 and TIM-3, the method comprising: introducing a peptide comprising any one of the sequences as set forth in SEQ ID NOs: 5-8 to an animal, wherein the animal produces the anti-Gal3 antibody.

In some embodiments, this disclosure provides a humanized anti-Gal3 antibody, wherein the antibody comprises (1) a light chain variable region comprising a complementary determining region (CDR) L1, a CDR L2, and a CDR L3 and (2) a heavy chain variable region comprising a CDR H1, a CDR H2, and a CDR H3, wherein the CDR L1 comprises the amino acid sequence of SEQ ID NO:17, the CDR L2 comprises the amino acid sequence of SEQ ID NO:18, the CDR L3 comprises the amino acid sequence of SEQ ID NO:19, the CDR H1 comprises the amino acid sequence of SEQ ID NO:9, the CDR H2 comprises the amino acid of SEQ ID NO:10, and the CDR H3 comprises the amino acid sequence of SEQ ID NO:11.

In some embodiments, the heavy chain variable region of the humanized antibody has a sequence having at least 90% identity to the amino acid sequence of SEQ ID NO: 25. In some embodiments, the light chain variable region of the humanized antibody has a sequence having at least 90% identity to the amino acid sequence of SEQ ID NO: 26.

In some embodiments, the humanized antibody is capable of blocking the interaction between Gal3 and TIM-3, thereby activating immune response.

In some embodiments, the disclosure provides a method of selecting compounds that can block interaction between Gal3 and TIM-3, activating immune response and/or treating cancer in a patient comprising (a) contacting a library of compounds with Gal3 and TIM-3, and (b) selecting one or more candidate compounds from the library that are capable of blocking the interaction between Gal3 and TIM-3. In some embodiments, the method further comprises (c) contacting the one or more candidate compounds selected from step (b) with a mixture comprising T cells, and allogeneic antigen presenting cells, and identifying one or more compounds that are capable of stimulating the T cells, and/or (d) administering the one or more candidate compounds selected from (b) to a mammal hosting a tumor and identifying one or more compounds that are capable of reducing tumor load of the mammal, and optionally (e) administering an effective amount of a compound that is capable of stimulating the T cells and/or capable of reducing tumor load of the mammal to the patient, thereby activating immune response and/or treating cancer in the patient. In some embodiments, the compounds are antibodies.

In some embodiments, the disclosure provides a Gal3:TIM-3 inhibitor, as disclosed in any of the embodiments above, for use in a methods of activating immune response in a patient comprising administering to the patient a Gal3:TIM-3 inhibitor that interferes with the interaction between Gal3 and TIM-3, wherein said inhibitor is administered in an amount sufficient to activate immune response. Optionally, the Gal3:TIM inhibitor is a humanized anti-Gal3 antibody as described above.

In some embodiments, the disclosure provides use of a Gal3:TIM-3 inhibitor, as disclosed in any of the embodiments above, in manufacturing a medicament (i.e., a pharmaceutical composition) for activating immune response and/or treating cancer. Optionally, the Gal3:TIM inhibitor is a humanized anti-Gal3 antibody as described above.

BRIEF DESCRIPTION OF THE DRAWINGS

FIG. 1A shows TIM-3 expression in the 293T cells co-transfected with a plasmid encoding a HA-tagged hTIM-3 and a plasmid encoding hGal3, hGal9, or hCEACAM1. FIG. 1B shows expression of hGal9, hGal3, or hCEACAM1. FIG. 1C shows that hGal3, but not CEACAM1, pulled down the-HA-tagged hTIM-3 in the co-transfected 293T cells. The results also show that human Gal9 (hGal9) pulled down hTIM-3, but the pull down was accompanied with protein aggregation (FIG. 1B), indicating the binding between hGal9 and hTIM-3 might be non-specific.

FIG. 4A shows live A20 cells (the peak on the left) and dead A20 cells (the peak on the right) by flow cytometry analysis. FIG. 4B and FIG. 4C show the results of flow cytometry analysis of the live cells (FIG. 4B) and dead cells (FIG. 4C) that are stained with anti hFc APC antibody. In group 1, A20 Gal3 cells were incubated without mTIM-3 Fc protein as control; in group 2, A20 Gal3 cells were incubated with mTIM-3 Fc protein; in groups 3, 4, 5, in addition to mTIM-3 Fc protein, anti-mouse TIM-3 polyclonal antibody (R&D System, Minneapolis, Minn.) (group 3), monoclonal antibody RMT3-23 (Bio X cell, West Lebanon, N.H.) (group 4), monoclonal antibody 215015 (R&D Systems) (group 5), were also added to test if these antibodies could block Gal3 and Tim3 binding.

In FIG. 5A, plates were coated with mGal3 at 10 ug/ml, mGal3 polyclonal antibody (mGal3 pAb) and monoclonal antibody IMT001, but not monoclonal antibody M3/38, were shown to block the interaction between Gal3 and Tim3. FIG. 5B shows that lactose blocked Gal9, but not Gal3 from binding to TIM-3, indicating that the binding between Gal3 and Tim3 is sugar-independent binding. FIG. 5C shows that antibody RMT3-23 blocked phosphatidylserine (PS), but not Gal3 from binding to Tim3, indicating the epitopes on TIM-3 that bind to Gal3 is different from those that bind to PS.

FIG. 6A shows that mouse A20 cell clones #41, #31, and #15 overexpress Gal3. FIG. 6B shows that when these cells were mixed with mouse DO11.10 T cells, much less IL-2 was produced as compared to parental A20 cells (FIG. 6B).

FIG. 7A shows high expression of Gal3 on B16F10 tumor cells. FIG. 7B shows representative images of the whole lung from three treated groups. FIG. 7C shows numbers of metastatic colonies on surface of the left lung lobe (Mean±SEM). FIG. 7D and FIG. 7E show lung weight and body weight of different treatment groups (Mean±SEM). As compared to animals that were treated with the isotype control, animals treated with the monoclonal anti-human Gal3 antibody showed significant reduction of tumor number (p<0.01) (FIG. 7B) and much less tumor burden as indicated by lung weight (p<0.05) (FIG. 7D). However, animals treated with PD1 antibody did not show significant reduction of tumor number or burden in this lung metastasis model (p>0.05). FIG. 7E shows that animals treated with either the PD1 antibody or the Gal3 antibody had similar body weight as the control group, indicating that there were no adverse effects associated with administration of either antibody.

FIG. 8A shows the images of metastasized tumor colonies on the lung of mice that have been implanted with 4T1 cells and then treated with either control antibody ("isotype") or IMT001. The antibodies were administered intraperitoneally on day 0, 3, 7, 10 and 14 during a period of 30 days. The images were taken at the day 30 when the mice were sacrificed. FIG. 8B shows the body weight measurements of these mice during the same period. FIG. 8C shows the number of metastasized tumor colonies on the surface of the left lobe of these mice at day 30.

FIGS. 11A-11D show the results of epitope mapping. A peptide array derived from hGal3 protein sequence was synthesized (FIG. 11A) and dot blotted with anti Gal3 antibody IMT001 (FIG. 11B). Peptides 5 and 6 showed good signal, indicating that the anti Gal3 monoclonal antibody, IMT001, can bind to these peptides. To further map the binding epitopes of IMT001 on these peptides, several shorter peptides derived from these peptide sequences were synthesized (FIG. 11C) and their binding to IMT001 was measured by ELISA (FIG. 11D). Peptide with sequence GQAPPGAYPG (SEQ ID NO: 8) produced the highest signal.

FIG. 13A shows the results from staining squamous cell carcinoma and FIG. 13B shows the results from staining of adenocarcinoma.

DETAILED DESCRIPTION OF THE INVENTION

Definitions

Figure 1:
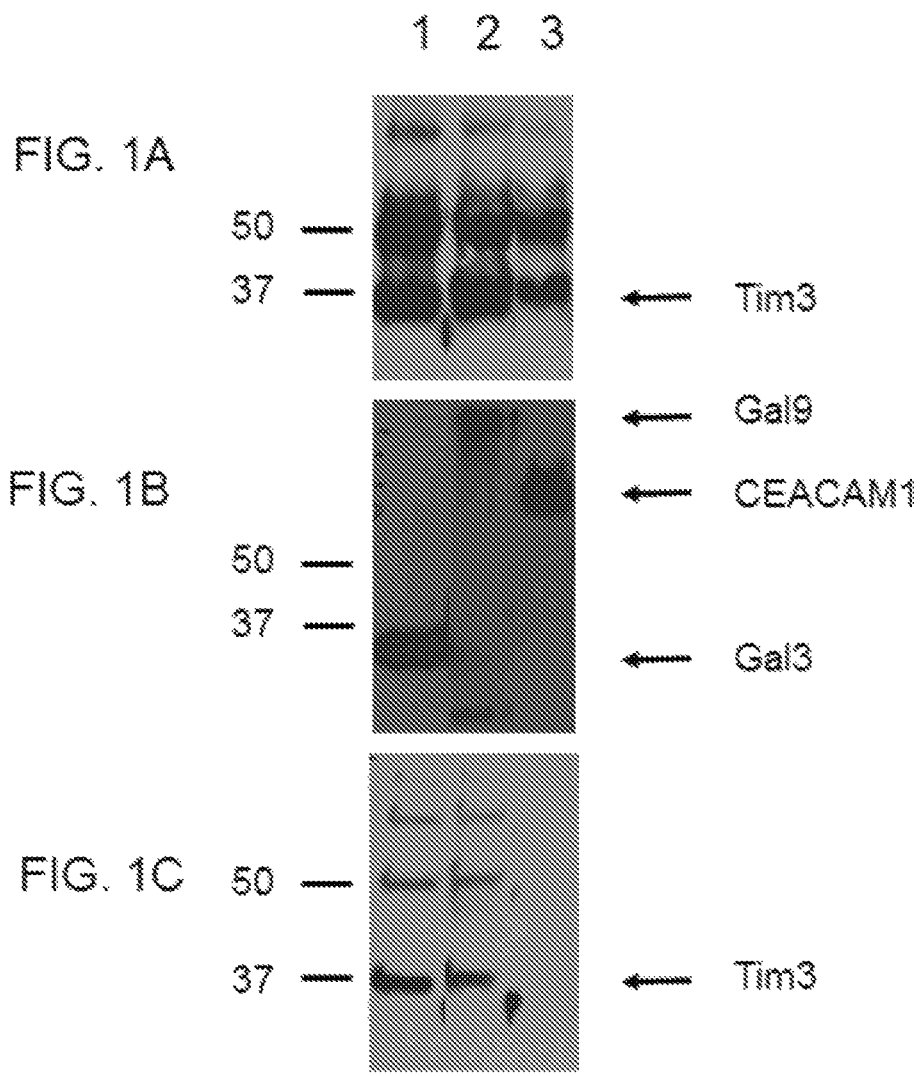
FIG. 1 shows the results of co-immunoprecipitation assay indicating that human Gal3 (hGal3) specifically pulled down human TIM-3 (hTIM-3).

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "comprise" refers to that the compositions include the recited elements, but not excluding others. Therefore, comprises can also mean the composition include only the recited elements. For example, a light chain comprises SEQ ID NO: 24, include the scenario that the light chain has the sequence as shown in SEQ ID NO: 24.

The terms "subject", "patient" or "individual" are used herein interchangeably to refer to a human or animal. For example, the animal subject may be a mammal, a primate (e.g., a monkey), a livestock animal (e.g., a horse, a cow, a sheep, a pig, or a goat), a companion animal (e.g., a dog, a cat), a laboratory test animal (e.g., a mouse, a rat, a guinea pig, a bird), an animal of veterinary significance, or an animal of economic significance.

The terms "polypeptide," "peptide," and "protein" are used interchangeably herein to include a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" includes naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs include compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" include chemical compounds that have a structure that is different from the general chemical structure of an amino acid, but that functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

The term "therapeutically effective amount" or "effective mount" includes an amount or quantity effective, at dosages and for periods of time necessary, to achieve the desired therapeutic or prophylactic result.

The term "administering" includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. One skilled in the art will know of additional methods for administering a therapeutically effective amount of the Gal3: TIM-3 inhibitor described herein to interfere with the interaction between Gal3 and TIM-3 on the T-cells to decrease the caner load of a patient. By "co-administer" it is meant that a first compound described herein is administered at the same time, just prior to, or just after the administration of a second compound described herein.

The term "tumor" and the term "cancer" are used interchangeably and both refer to an abnormal growth of tissue that results from excessive cell division.

The term "tumor microenvironment" refers to a cellular environment in which the tumor exists, including tumor cells and surrounding blood vessels, immune cells, fibroblasts, bone marrow-derived inflammatory cells, lymphocytes, signaling molecules and the extracellular matrix.

The term "immune cells" refers to cells of hematopoietic origin that are involved in the specific recognition of antigens. Immune cells include antigen presenting cells (APCs), such as dendritic cells or macrophages, B cells, T cells, natural killer cells, and myeloid cells, such as monocytes, macrophages, eosinophils, mast cells, basophils, and granulocytes.

The term "immune response" refers to T cell-mediated and/or B cell-mediated immune responses. Exemplary immune responses include B cell responses (e.g., antibody production) T cell responses (e.g., cytokine production, and cellular cytotoxicity) and activation of cytokine responsive cells, e.g., macrophages. The term "activating immune response" refers to enhancing the level of T-cell-mediated and/or B cell-mediated immune response, using methods known to one of skilled in the art. In one embodiment, the level of enhancement is at least 20 50%, alternatively at least 60%, at least 70%, at least 80%, at least 90%, at least 100%, at least 120%, at least 150%, or at least 200%.

The term "recognizes" refers to a phenomenon that a molecule is able to specifically and selectively bind to a second molecule. Typically, a specific or selective binding will be at least twice background signal or noise and more typically more than 10 to 100 times background.

The term "Gal3:TIM-3 inhibitor" refers to a molecule that inhibits the interaction between Gal3 and TIM-3 and the inhibition results in T cell activation.

The term "TIM-3:Gal3" or "Gal3:TIM-3" pathway refers to the signal pathway in which TIM-3 binds to Gal3, and the interaction suppresses T cell activation.

The term "activating T cells" refers to phenomenon that T cells are activated and engaged in signaling pathways that promote immune responses. The activation of T cells is typically accompanied with T cell proliferation and/or release of cytokines, e.g., interferon-gamma, IL-2, IL-5, IL-10, IL-12, or transforming growth factor (TGF)-beta.

The term "cancer over expressing Gal3" refers to a cancer in which expresses a higher level of Gal 3 on cell surface relative to the control cells. In some cases, the control cells are cells from similar tissue in a healthy individual. In some cases, the control cells are non-cancerous cells from the same individual that hosts the cancer.

The term "cancer load," "tumor load," or "tumor burden" generally refers to the number of cancer cells, the size of a tumor, or the amount of cancer in the body in a subject at any given time. Tumor load can be detected by e.g., measuring the expression of tumor specific genetic markers and measuring tumor size by a number of well-known, biochemical or imaging methods disclosed herein, infra.

The term "threshold activity value" refers to an expression level or an activity level, a comparison with which may aid the determination whether a diagnosis can be made or a treatment can be prescribed. In some embodiments, the threshold activity value is the median expression level of Gal3 on the cancer cells from a heterogeneous population having the same type of cancer as the patient being treated. In some embodiments, the threshold activity value is the level of Gal3 on the non-cancerous tissue of the patient that hosts the cancer. In some embodiments, the threshold activity level is the expression level or activity level of Gal3 on cells of similar tissue type on healthy individuals.

The term "antibody" is used in the broadest sense and specifically covers monoclonal antibodies, polyclonal antibodies, multispecific antibodies, e.g., bispecific antibodies, chimeric antibodies, humanized antibodies, fully synthetic antibodies and antibody fragments so long as they exhibit the desired biologic activity, i.e., binding specificity. An antibody is a monomeric or multimeric protein comprising one or more polypeptide chains. An antibody binds specifically to an antigen and can be able to modulate the biological activity of the antigen. The term "antibody" also includes antibody fragments. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883), (viii) bispecific single chain Fv dimers (PCT/US92/09965) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448). In certain embodiments, antibodies are produced by recombinant DNA techniques. Other examples of antibody formats and architectures are described in Holliger & Hudson, 2006, Nature Biotechnology 23(9):1126-1136, and Carter 2006, Nature Reviews Immunology 6:343-357 and references cited therein, all expressly incorporated by reference. In additional embodiments, antibodies are produced by enzymatic or chemical cleavage of naturally occurring antibodies.

The term "humanized antibody" refers to antibodies in which CDR sequences derived from the germline of another mammalian species, such as a mouse, have been grafted onto human framework sequences. Framework region modifications may be made within the human framework sequences.

The term "framework" refers to variable domain residues other than hypervariable region residues. The "framework regions" or "FRs" of different light or heavy chains are relatively conserved within a species. The framework of a variable domain generally consists of four FR domains: FR1, FR2, FR3, and FR4. framework region modifications may be made within the human framework sequences. The framework region of an antibody, which is the combined framework regions of the constituent light and heavy chains, serves to position and align the CDRs in three-dimensional space. Framework sequences can be obtained from public DNA databases or published references that include germline antibody gene sequences. For example, germline DNA sequences for human heavy and light chain variable region genes can be found in the "VBASE2" germline variable gene sequence database for human and mouse sequences.

The terms "variable region" and "variable domain" as used herein refer to the portions of the light and heavy chains of an antibody that include amino acid sequences of complementary determining regions (CDRs, e.g., CDR H1, CDR H2, CDR H3, CDR L1, CDR L2, and CDR L3) and framework regions (FRs). The amino acid positions assigned to CDRs and FRs may be defined according to Chothia, Kabat (Sequences of Proteins of Immunological Interest, 5th Ed. Public Health Service, National Institutes of Health, Bethesda, Md. (1991)), or international ImMunoGeneTics database (IMGT). The variable region in an antibody heavy chain or light chain is derived from a germline Variable (V) gene, Diversity (D) gene, or Joining (J) gene (and not derived from a Constant (Cμ and Cδ) gene segment), and gives an antibody its specificity for binding to an antigen. Typically, an antibody variable region comprises four conserved "framework" regions interspersed with three hypervariable "complementarity determining regions."

As used herein, the terms "complementary determining regions" and "CDRs" refer to the regions of an antibody variable region which are hypervariable in sequence and/or form structurally defined loops. A CDR is also known as a hypervariable region. The light chain and heavy chain variable regions each has three CDRs. The light chain variable region contains CDR L1, CDR L2, and CDR L3. The heavy chain variable region contains CDR H1, CDR H2, and CDR H3. Each CDR may include amino acid residues from a complementarity determining region as defined by Chothia, Kabat (Sequences of Proteins of Immunological Interest, 5th Ed. Public Health Service, National Institutes of Health, Bethesda, Md. (1991)), or international ImMunoGeneTics database (IMGT).

The term "human antibody" refers to an antibody that possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "chimeric antibody" refers to antibodies in which the variable region sequences are derived from one species and the constant region sequences are derived from another species, such as an antibody in which the variable region sequences are derived from a mouse antibody and the constant region sequences are derived from a human antibody.

The term "a checkpoint inhibitor therapy" refers to a therapy that suppresses a checkpoint pathway. Non-limiting examples of checkpoint inhibitor therapies include therapies that inhibit the PD1 signaling pathway and therapies that inhibit the CTLA4 signaling pathway. A checkpoint inhibitor therapy can be a peptide, an antibody, a nucleoside analog (e.g., an aptamer), a small molecule compound, or combinations thereof.

The term "primary cancer" refers to a cancer that is at a location of the body or a tissue where the particular cancer starts. Primary cancer is often referred to as the first or original cancer. Primary cancer is the opposite of metastasis, which refers to the migration of cancer cells from the original tumor site to produce cancer in other tissues.

The term "metastatic cancer" refers to a cancer that has spread from the site of origin (where it started) into different area(s) of the body.

The term "primary cancer cells" refers to cancer cells that are isolated from a cancer patient, e.g., a cancer biopsy, and have not been cultured in vitro.

The term a cancer is "suitable for treatment of a Gal3:TIM-3 inhibitor" refers a cancer that is likely to respond to treatment with a Gal3:TIM-3 inhibitor, for example, the patient receiving the Gal3:TIM-3 inhibitor is likely to have a beneficial clinical outcome, such as, overall survival rate, time to progression, disease-free survival, progression-free survival, tumor load reduction, or any of other beneficial clinical outcome as disclosed below or those according to the RECIST criteria.

Overview

This invention is based on the surprising discovery that TIM-3 binds specifically to the Gal3 protein and the interaction results in suppression of T cell activation. The disclosure provides methods that restore T cell activation by administering an inhibitor that interferes with the interaction between Gal3 and TIM-3 to treat patients hosting a cancer, especially the cancer types that overexpresses Gal3. The disclosure additionally provides methods of determining if a cancer is suitable for treatment using the Gal3:TIM-3 therapy by determining the level of Gal3 on the surface of the cells in the tumor microenvironment, e.g., cancer cells and tumor-associated macrophages, and comparing the level of Gal3 with a threshold activity value.

1. Select Patient Population

Gal3, also known as Galectin-3, is expressed in several cell types and involved in a broad range of physiological and pathological processes, which include cell adhesion, cell activation and chemoattraction, cell cycle, apoptosis, cell growth and differentiation, and tumor progression and metastasis. Gal3 expresses on tumors cells and cells in the tumor microenvironment, e.g., tumor-associated macrophages, especially M2 macrophages, as described below.

TIM-3 is a molecule expressed on immune cells, especially on T cells and can suppress immune response, e.g., T cell signaling, through the interaction with Gal3. The Gal3:TIM-3 inhibitors disclosed herein can interfere with the interaction between Gal3 and TIM-3 and activate immune response. The Gal3:TIM-3 inhibitor disclosed herein can be used to treat cancers or other diseases that could benefit from activation of immune response.

Cancer cells in a solid tumor are able to form a tumor microenvironment in their surroundings to support the growth and metastasis of the cancer cells. A tumor microenvironment is the cellular environment in which the tumor exists, including surrounding blood vessels, immune cells, fibroblasts, other cells, soluble factors, signaling molecules, an extracellular matrix, and mechanical cues that can promote neoplastic transformation, support tumor growth and invasion, protect the tumor from host immunity, foster therapeutic resistance, and provide niches for dormant metastases to thrive. The tumor and its surrounding microenvironment are closely related and interact constantly. Tumors can influence their microenvironment by releasing extracellular signals, promoting tumor angiogenesis and inducing peripheral immune tolerance, while the immune cells in the microenvironment can affect the growth and evolution of cancerous cells. See Swarts et al. "Tumor Microenvironment Complexity: Emerging Roles in Cancer Therapy," Cancer Res, vol., 72, pages 2473-2480, 2012.

Tumors are often associated with an immune infiltrate as part of the reactive stroma that is enriched for macrophages. Tumor-associated macrophages (TAMs) play an important role in facilitating tumor growth by promoting neovascularization and matrix degradation. When associated with tumors, macrophages demonstrate functional polarization towards one of two phenotypically different subsets of macrophages: M1 macrophages (also known as TH1) or M2 macrophages (also known as TH2). M1 macrophages are known to produce pro-inflammatory cytokines and play an active role in cell destruction while M2 macrophages primarily scavenge debris and promote angiogenesis and would repair. Consequently, many tumors with a high number of TAMs have an increased tumor growth rate, local proliferation and distant metastasis. The M2 macrophage population is phenotypically similar to the TAM population that promotes tumor growth and development. In addition to expressing Gal3, M2 macrophages may also express one or more cell surface markers selected from the group consisting of CD206, IL-4r, IL-1ra, decoy IL-1rII, IL-10r, CD23, macrophage scavenging receptors A and B, Ym-1, Ym-2, Low density receptor-related protein 1 (LRP1), IL-6r, CXCR1/2, CD136, CD14, CD1a, CD1b, CD93, CD226, (FcyR) and PD-L1.

The Gal3:TIM-3 inhibitors disclosed herein can be used to treat a cancer that overexpresses Gal3 in a tumor microenvironment. In some cases, the cancer comprises cancer cells that overexpress Gal3 on their surface. In some cases, the cancer comprises other types of cells that are included in the tumor microenvironment, e.g., tumor-associated macrophages, blood vessels, stroma cells, fibroblasts, that overexpress Gal 3 on the surface. In some cases, the cancer overexpresses Gal3 and the Gal3 exists as a soluble protein to the tumor microenvironment. Unless otherwise noted, the term "overexpress" refers to the at least 10%, at least 20%, at least 30%, at least 40%, or at least 50% above the expression levels in controls, e.g., similar cells, tissues, or regions of the body from healthy individuals.

In some embodiments, the Gal3:TIM-3 inhibitors disclosed herein are useful for treating various types of cancers having a higher level of Gal3 on the surface of cells in the tumor microenvironment, e.g., the cancer cells or tumor-associated macrophages, as compared to control cells. Expression level of Gal3 on the cell surface can be measured by methods well known in the art, including, but not limited to, flow cytometry and immunohistochemistry. Typically, detecting the expression level of Gal3 in the tumor microenvironment comprises combining a sample comprising cells from the tumor microenvironment, including the cancer cells and/or tumor-associated macrophages (e.g., M2 TAMs), with an anti-Gal3 antibody and the level of Gal3 on the cell surface is indicated by the amount of Gal3 antibody that is able to bind the cell surface. In some embodiments, the level of Gal3 is determined by measuring a detectable label conjugated to the Gal3 antibody.

In some embodiments, a labeled secondary antibody that binds to the Gal3 antibody is used and the Gal3 expression level is determined by measuring the signals from the labels on the secondary antibody. Alternatively, the antibody can be conjugated with biotin, and detectably labeled avidin (a polypeptide that binds to biotin) can be used to detect the presence of the biotinylated antibody. Appropriate detectable labels that can be used include, without limitation, radionuclides (e.g., $^{125}$I, $^{131}$I, $^{35}$S, $^{3}$H, or $^{32}$P), enzymes (e.g., alkaline phosphatase, horseradish peroxidase, luciferase, or .beta.-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.).

In some embodiments, the Gal3 expression level of the cancer that has been determined is compared with a threshold activity level to determine if the cancer is suitable for treatment with a Gal3:TIM-3 inhibitor disclosed herein. In some embodiments, the threshold activity level is expression level or activity level of Gal3 in cells of the non-cancerous tissue of the patient that hosts the cancer. In some embodiments, the threshold activity level is the expression level or activity level of Gal3 on cells of similar tissue type on healthy individuals. In some embodiments the threshold activity level is from individual median expression level of Gal3 on a cohort of patients having the same type of cancer and the cohort of patients are of a heterogeneous population with regard to the expression level of Gal3. The test cohort preferably comprises at least 25, 50, 100, 200, 1000 individuals or more including all values and ranges thereof. In some embodiments, the expression levels of Gal3 in the patient and the threshold activity levels are normalized before comparison.

Thus, in some embodiments, the disclosure provides a method of determining if a patient's cancer is suitable for treatment with a Gal3:TIM-3 inhibitor and the method comprises obtaining a sample containing the cancer cells from the patient, determining the level of Gal3 on the cell surface in the sample, comparing the levels of the Gal3 on the cells with a threshold activity level, and determining that the patient's cancer is suitable for treatment with a Gal3: TIM-3 inhibitor if the Gal3 surface expression on the cancer cells of the patient is at least 15%, at least 25%, at least 50%, at least 75%, at least 2-fold, at least 5-fold, at least 10-fold, at least 100-fold, at least 1000-fold, or at least 10000-fold higher than the threshold activity value. In some embodiments, the threshold activity level used for the comparison can be based on the average, mean, or median level of the Gal3 on the surface of the cancer cells of the same cancer type from at least 100, 200, 300, 500 cancer patients. In some embodiments, the threshold activity level based on the average, mean, or median level of Gal3 on the surface of cells of similar tissue type from healthy individuals. In some embodiments, the cancer cells in the sample used for determination whether a cancer is suitable for treatment with a Gal3:TIM-3 are primary cancer cells.

A number of cancer types will overexpress Gal3 on the surface, including those that are metastatic, and thus are suitable for being treated using the method disclosed herein. These cancer types include, but not limited to, lung cancer, liver cancer, ovarian cancer, cervical cancer, skin cancer, bladder cancer, colon cancer, breast cancer, glioma, renal carcinoma, stomach cancer, esophageal cancer, oral squamous cell cancer, head/neck cancer, melanoma, sarcoma, renal cell tumor, hepatocellular tumor, glioblastoma, neuroendocrine tumor, bladder cancer, pancreatic cancer, gall bladder cancer, gastric cancer, prostate cancer, endometrial cancer, thyroid cancer and mesothelioma. Thus, in some cases, the cancers that are suitable for being treated using the methods disclosed herein are metastatic cancers that originate from the tumor as described above, e.g., metastatic lung cancer 2. Gal3:TIM-3 Inhibitor The disclosure provides a method to treat cancer by administration to the patient an therapeutically effective amount of at least one Gal3:TIM-3 inhibitor. A Gal3:TIM-3 inhibitor can be any molecule that inhibits the interaction between Gal3 and TIM-3 and said inhibition results in activation of T cells. In some embodiments, the Gal3:TIM-3 inhibitor binds to the TIM-3 protein and such inhibitor is referred to as the TIM-3 inhibitor in this disclosure. In some embodiments, the Gal3:TIM-3 inhibitor binds to the Gal3 protein and such inhibitor is referred to as the Gal3 inhibitor. The Gal3:TIM-3 inhibitor can be a protein (e.g., an antibody) or a small molecule. An antibody that is a Gal3:TIM-3 inhibitor is referred to as GIA in this disclosure.

i. Gal3:TIM-3 Inhibitor Antibodies ("GIA")

In one embodiment, the method for treating cancer comprises administering a Gal3:TIM-3 inhibitor antibody. Such an antibody can block the interaction between Gal3 and TIM-3 and activate T cells. In some embodiments, the Gal3:TIM-3 inhibitor antibody is a Gal3 inhibitor antibody. In some embodiments, the Gal3:TIM-3 inhibitor antibody is a TIM-3 inhibitor antibody.

Generating GIAs

GIAs can be developed using methods well known in the art. See, for example, Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991). Monoclonal antibodies can be obtained by injecting mice with a composition comprising an antigen, e.g. a Gal3 or an epitope of thereof, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures. In some embodiments, the epitope of Gal3 that is used to produce the Gal3 inhibitor antibodies is: SEQ ID NO: 5 (PGAYPGQAPPGAYPGQAPPG), SEQ ID NO 6 (GAYPGQAPPGAYPGAPGAYP) SEQ ID NO: 7: (PGAYPGQAPPGAYPGQAPPGAYPGAPGAYP), SEQ ID NO:8 (GQAPPGAYPG).

Monoclonal antibodies produced can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992). After the initial raising of antibodies to the target protein, the antibodies can be sequenced and subsequently prepared by recombinant techniques. Humanization and chimerization of murine antibodies and antibody fragments are well known to those skilled in the art. See, for example, Leung et al. Hybridoma 13:469 (1994); US20140099254 A1.

Human antibodies can be produced using transgenic mice that have been genetically engineered to produce specific human antibodies in response to antigenic challenge using the target protein. See Green et al., *Nature Genet.* 7: 13 (1994), Lonberg et al., Nature 368:856 (1994). Human antibodies against the target protein can also be constructed by genetic or chromosomal transfection methods, phage display technology, or by in vitro activated B cells. See e.g., McCafferty et al., 1990, Nature 348: 552-553; U.S. Pat. Nos. 5,567,610 and 5,229,275.

In some embodiments, the GIA is an anti-Gal3 antibody. In some embodiments, the GIA binds to a peptide having the sequence of SEQ ID NO: 5, 6, 7 or 8. In some embodiments, the GIA is an antibody that is capable of binding to Gal3 and interfering with the interaction between TIM-3 and Gal3. In some embodiments, the GIA is an antibody that is capable of binding to a peptide comprising a sequence selected from any of SEQ ID NOs: 5-8 and interfering with the interaction between TIM-3 and Gal3. In some embodiments, the GIA is an antibody that is capable of blocking a known GIA from binding to Gal3 and interfering with the interaction between TIM-3 and Gal3. In some cases, the administration of a Gal3:TIM-3 inhibitor as disclosed herein, e.g., an Gal3 inhibitor antibody, may reduce tumor burden by at least 20%, e.g., at least 30%, at least 40%, or at least 46% in a mouse model over the treatment period, e.g., a period of three to twelve weeks.

In some embodiments, the GIA is an anti-Gal3 antibody. In some embodiments, the anti-Gal3 antibody is of IgG4 isotype. In some embodiments, the anti-Gal3 antibody comprises a heavy chain variable region complementarity-determining regions CDRs 1, 2, and 3 (CDR H1, CDR H2, and CDR H3), wherein the CDR H1 comprises the amino acid sequence of SEQ ID NO: 9, the CDR H2 comprises the amino acid sequence of SEQ ID NO: 10, and/or the CDR H3 comprises SEQ ID NO: 11. In some embodiments, the heavy chain variable region of the anti-Gal3 antibody comprises framework regions 1-4 (FR H1, FR H2, FR H3, and FR H4), wherein the FR H1 comprises the amino acid sequence of SEQ ID NO: 12, the FR H2 comprises the amino acid sequence of SEQ ID NO: 13, the FR H3 comprises the amino acid sequence of SEQ ID NO: 14, and/or the FR H4 comprises the amino acid sequence of SEQ ID NO: 15. In some embodiments, the heavy chain of the anti-Gal3 antibody comprises the amino acid sequence of SEQ ID NO: 16.

In some embodiments, the anti-Gal3 antibody comprises a light chain variable region complementarity-determining regions CDRs 1, 2, and 3 (CDR L1, CDR L2, and CDR L3), wherein CDR L1 comprises the amino acid sequence of SEQ ID NO: 17, a CDR L2 comprises the amino acid sequence of SEQ ID NO: 18, and/or a CDR L3 comprises SEQ ID NO: 19. In some embodiments, the heavy chain variable region of the anti-Gal3 antibody comprises frame regions 1-4 (FR L1, FR L2, FR L3, and FR L4), wherein the FR L1 comprises the amino acid sequence of SEQ ID NO: 20, the FR L2 comprises the amino acid sequence of SEQ ID NO: 21, the FR L3 comprises the amino acid sequence of SEQ ID NO: 22, and/or the FR L4 comprises the amino acid sequence of SEQ ID NO: 23. In some embodiments, the light chain of the anti-Gal3 antibody comprises the amino acid sequence of SEQ ID NO: 24.

In some embodiments, the anti-Gal3 antibody comprises a heavy chain variable region comprising the amino acid sequence of SEQ ID NO: 25. In some embodiments, the anti-Gal3 antibody comprises a light chain variable region comprising the amino acid sequence of SEQ ID NO: 26.

Modifying GIAs

GIAs may also be produced by introducing conservative modifications relative to the existing GIAs. For example, a modified GIA may comprise heavy and light chain variable regions, and/or a Fc region that are homologous to the counterparts of an antibody produced above. The modified GIA that can be used for the method disclosed herein must retain the desired functional properties of being able to block the Gal3:TIM-3 signaling pathway.

GIAs described herein can be linked to another functional molecule, e.g., another peptide or protein (albumin, another antibody, etc.), toxin, radioisotope, cytotoxic or cytostatic agents. For example, the antibodies can be linked by chemical cross-linking or by recombinant methods. The antibodies may also be linked to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; or 4,179,337. The antibodies can be chemically modified by covalent conjugation to a polymer, for example, to increase their circulating half-life. Exemplary polymers and methods to attach them are also shown in U.S. Pat. Nos. 4,766,106; 4,179,337; 4,495,285; and 4,609,546.

GIAs may also be produced by altering protein modification sites. For example, sites of glycosylation of the antibody can be altered to produce an antibody lacking glycosylation and the so modified GIAs typically have increased affinity of the antibody for antigen. Antibodies can also be pegylated by reacting with polyethylene glycol (PEG) under conditions in which one or more PEG groups become attached to the antibody. Pegylation can increase the biological half-life of the antibody. Antibodies having such modifications can also be used to treat the Gal3-overexpressing tumors so long as it retains the desired functional properties of blocking the TIM3-Gal3 pathways.

The antibodies may also be tagged with a detectable, or functional, label. Detectable labels include radiolabels such as $^{131}$I or $^{99}$Tc, which may also be attached to antibodies using conventional chemistry. Detectable labels also include enzyme labels such as horseradish peroxidase or alkaline phosphatase. Detectable labels further include chemical moieties such as biotin, which may be detected via binding to a specific cognate detectable moiety, e.g., labeled avidin.

In another aspect, the present invention features bispecific molecules comprising an anti-Gal3 or anti-TIM-3 antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results. In one illustrative embodiment, the bispecific antibody can be created using the knobs-into-holes strategy. The strategy typically involves first creating a first half of the antibody that recognizes a first antigen, e.g., Gal3, and a second half of the antibody that recognizes a second antigen and then joining the two halves to create the bispecific antibody.

Accordingly, the present invention includes bispecific molecules comprising at least one first binding specificity for Gal3 or TIM-3 and a second binding specificity for a second target. In some embodiments, the second target is a known cancer target, for example, PD-L1. In some embodiments, the second target epitope is TIM-3 or Gal3 and the bispecific molecule is capable of binding to TIM-3 and Gal3 simultaneously. In some embodiments, the second target is an Fc receptor, e.g., human Fc.gamma.RI (CD64) or a human Fc.alpha. receptor (CD89). Therefore, the invention includes bispecific molecules capable of binding both to Fc.gamma.R or Fc.alpha.R expressing effector cells (e.g., monocytes, macrophages or polymorphonuclear cells (PMNs)), and to target cells expressing Gal3. These bispecific molecules target Gal3 expressing cells to effector cell and trigger Fc receptor-mediated effector cell activities, such as phagocytosis of an PD-1 expressing cells, antibody dependent cell-mediated cytotoxicity (ADCC), cytokine release, or generation of superoxide anion.

ii. Other Gal3:TIM-3 Inhibitor Molecules

In another embodiment, the Gal3:TIM-3 inhibitor disclosed herein is a small molecule, non-protein compound that interferes with the interaction between Gal3 and TIM-3 and thus antagonizes a TIM-3's immune suppression function. These small molecules typically are organic molecules having a molecular weight between 50 daltons to 2500 daltons. The compounds can also be identified using any of the numerous approaches in combinatorial library methods known in the art and disclosed in, e.g., European patent application EP2360254. The cominatorial libraries include: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

iii. Evaluating Candidate Gal3:TIM-3 Inhibitors

A number of well-known assays can be used to assess whether a candidate, e.g., an antibody generated by immunizing an animal with an antigen comprising a Gal3 protein or a test compound from combinatorial libraries, can block interaction between Gal3 and TIM-3. Typically, it involves evaluations of the candidate using one or more of the following types of assays: i) binding assays to test whether the candidate binds to the target protein, i.e., Gal3 or TIM-3; ii) blocking assays to test whether the candidate can block the interaction between Gal3 and TIM-3; iii) cell-based functional assays to test whether the candidate, by blocking the interaction between Gal3 and TIM-3, can activate T cells; and iv) in vivo efficacy assays to test whether the candidate can reduce tumor load.

Binding Assays

Any of the assays that are used to evaluate interaction of two molecules can be used to determine whether the candidate can bind to the target protein. Non-limiting exemplar assays include binding assays—such as Enzyme-Linked Immunosorbent Assays (ELISAs), radioimmunoassays (RIA)—, Fluorescence-Activated Cell Sorting (FACS) analysis. In some cases, the target protein, i.e., Gal3 or TIM-3 protein, can be coupled with a radioisotope or enzymatic label such that binding of the target protein and the candidate can be determined by detecting the labeled target protein in a complex. For example, the target protein can be labeled with $^{125}I$, $^{35}S$, $^{14}C$, or $^{3}H$, either directly or indirectly, and the radioisotope detected by direct counting of radio-emission or by scintillation counting. Alternatively, the target protein molecules can be enzymatically labeled with, for example, horseradish peroxidase, alkaline phosphatase, or luciferase, and binding of the candidates to the target protein is determined by conversion of an appropriate substrate to product.

In some embodiments, immunoassays, such as Enzyme-linked immunosorbent assay (ELISA), can be used to evaluate a Gal3:TIM-3 inhibitor candidate's binding specificity to its target protein. In some embodiments, samples comprising the candidate are added to the plates that are pre-coated with the target protein and incubated for a period of time. A labeled secondary antibody that recognizes the candidate can be added and signal from the labeled secondary antibody are detected. In some cases, the secondary antibody is conjugated to an enzyme and the binding can be assessed by addition of substrate specific for the enzyme and read at appropriate wavelength according to manufacturer's instructions. Non-limiting examples of enzymes that can be used include horseradish peroxidase and alkaline phosphatase. For horseradish peroxidase, the ABTS substrate can be used and readings at 415-490 nm can be taken to evaluate the capability of the candidate's binding to Gal3 or TIM-3. Alternatively, the ELISA can also be performed by coating the candidate on the plate, adding the target protein to the plate and detecting the binding as described above.

The binding kinetics (e.g., binding affinity) of the candidates also can be assessed by standard assays known in the art, such as by Biacore analysis (Biacore A B, Uppsala, Sweden). In one exemplary assay, the target protein is covalently linked to a chip, e.g., a carboxy methyl dextran coated chip using standard amine coupling chemistry and kit provided by Biacore. Binding is measured by flowing the candidates in buffers (provided by Biacore AB) at appropriate concentrations a flow rate that is recommended by the manufacturer. The association kinetics and dissociate kinetics are recorded and the association kinetics and dissociate curves are fitted to a binding model using BIA evaluation software (Biacore AB). The $K_D$, $K_{on}$ and $K_{off}$ values of the interaction can be measured. Preferred Gal3:TIM-3 inhibitors can bind to their target protein with a Kd of $1 \times 10^{-7}$ M or less, e.g., $5 \times 10^{-7}$ M or less or $1 \times 10^{-8}$ M or less.

Blocking Assays

Candidates that have demonstrated the ability to bind the target protein are then evaluated for their ability to block the interaction between TIM-3 and Gal3 in a blocking assay. In some embodiments, the blocking assay is an immunoassay, e.g., an ELISA. In one embodiments, the method of determining if the candidate blocks the interaction between the TIM-3 and Gal3 involves coating the plates with one of the target protein, TIM-3 or Gal3, and adding a mixture of the candidate and the other target protein, i.e., Gal3 or TIM-3, to the coated plates, and detecting the signal corresponding to the binding of TIM-3 and Gal3. A decrease in signal as compared to control reactions, in which no candidate is added, indicates the candidate is capable of the blocking the interaction between Gal3 and TIM-3.

In some embodiments, the blocking assay is a flow cytometry assay. In general, the candidate is mixed with one of the target proteins, TIM-3 or Gal3, and the mixture is added to cells overexpressing the other target protein, Gal3 or TIM-3. The binding of the TIM-3 and Gal3 on the cell surface can be detected by fluorescently labeled antibodies. A decrease in signal in reactions containing the candidate as compared to control indicates that the candidate can block the interaction between TIM-3 and Gal3. Exemplary blocking assays that can be used to determine whether a candidate can block the interaction between the TIM-3 and Gal3 are described in Example 2.

Functional Assays

In some cases, candidates that have demonstrated binding to target proteins are further evaluated for its ability to activate T cells using the Mixed Lymphocyte Reaction (MLR) assay. One exemplary assay is described in U.S. Pat. No. 8,008,449, the relevant disclosure is hereby incorporated by reference in its entirety. The MLR assay can be used to measure T cell proliferation, production of IL-2 and/or IFN-γ. In one exemplary assay, a candidate is added to a number of purified T cells cultured with antigen presenting cells (APCs) at different concentrations. The cells are then cultured in the presence of the candidate for a period of between 4-7 days at 37° C. A certain volume of culture medium is then taken for cytokine measurement. The levels of IFN-gamma and other cytokines can be measured. Methods for measuring cytokine production are well known and commercial kits are readily available, e.g., OptEIA ELISA kits (BD Biosciences). In some embodiments, cells are cultured in the presence of $^{3}H$-thymidine for a period of between 12 to 24 hours, e.g., 18 hours, and analyzed for amount of incorporation of $^{3}H$-thymidine in the cells, which is positively correlated to cell proliferation. Results showing that, as compared to control, the culture containing the candidate shows increased T cell proliferation, increased production of IL-2, and/or IFN-gamma indicate the candidate is effective in activating T cells by blocking the interaction of TIM-3 and Gal3. One exemplary assay of MLR that can be used for evaluating the candidate's capability in activating T cells is disclosed in Example 11.

In Vivo Assays

In another embodiment, an in vivo assay is used to evaluate whether a candidate is effective in treating cancer. In vivo assays can be done in tumor models, such as mouse tumor models, according to well-established procedures. In brief, the animals, e.g., mice, are implanted subcutaneously with human tumor cell lines. When the tumors grow and reach a certain size, e.g., between 100 and 300 mm³, the candidate is administered to the mice at a predetermined frequency at appropriate dosages. The candidate can be administered by a number of routes, such as intraperitoneal injection or intravenous injection. The animals are monitored once or twice weekly for tumor growth for period of time which usually lasts 4 to 8 weeks. The tumors are measured three dimensionally (height×width×length) and tumor volumes are calculated. Mice are typically euthanized at the end of the experiment, when the tumors reach tumor end point, e.g., 1500 mm$^3$, or the mice show significant weight loss, e.g., greater than 15%, greater than 20%, or greater than 25% weight loss. A result showing that a slower tumor growth in the candidate treated group as compared to controls, or a longer mean time to reach the tumor end point volume is an indication that the candidate has activity in inhibiting cancer growth. One exemplary assay of in vivo efficacy assay that can be used for evaluating the candidate's capability in treating tumor is disclosed in Example 4.

4. Evaluate The Efficacy Of The Gal3:TIM-3 Inhibitor Therapy

The Gal3:TIM-3 inhibitor therapy disclosed herein can reduce the tumor load and confer beneficial, clinical outcome to cancer patients, especially those having Gal3-overexpressing cancer. Methods for measuring these responses are well-known to skilled artisans in the field of cancer therapy, e.g., as described in the Response Evaluation Criteria in Solid Tumors ("RECIST") guidelines, available at: ctep.cancer.gov/protocolDevelopment/docs/recist_guideline.pdf.

In one approach, the tumor load is measured by assaying expression of tumor-specific biomarkers. This approach is especially useful for metastatic tumors. A tumor-specific biomarker is a protein or other molecule that is unique to cancer cells or is much more abundant in them as compared to non-cancer cells. Useful biomarkers for various cancer are known, Non-limiting examples of tumor-specific genetic markers include, alpha-fetoprotein (AFP) for liver cancer, beta-2-microglobulin (B2M) for multiple myeloma; beta-human chorionic gonadotropin (beta-hCG) for choriocarcinoma and germ cell tumors; CA19-9 for pancreatic cancer, gall bladder cancer, bile duct cancer, and gastric cancer; CA-125 and HE4 for ovarian cancer; carcinoembryonic antigen (CEA) for colorectal cancer; chromogranin A (CgA) for neuroendocrine tumor; fibrin/fibrinogen for bladder cancer; prostate-specific antigen (PSA) for prostate cancer; and thyroglobulin for thyroid cancer. See, www.cancer.gov/about-cancer/diagnosis-staging/diagnosis/tumor-markers-fact-sheet.

Methods of measuring the expression levels of a tumor-specific genetic marker are well known. In some embodiments, mRNA of the genentic marker is isolated from the blood sample or a tumor tissue and real-time reverse transcriptase-polymerase chain reaction (RT-PCR) is performed to quantify expression of the genetic marker. In some embodiments, western blots, immunohistochemistry, or flow cytometry analysis are performed to evaluate the protein expression of the tumor-specific genetic marker. Typically the levels of the tumor-specific genetic marker are measured in multiple samples taken over time of the therapy of the invention, and a decrease in levels correlates with a reduction in tumor load.

In another approach, the reduction of tumor load by the Gal3:TIM-3 inhibitor therapy disclosed herein is shown by a reduction in tumor size or a reduction of amount of cancer in the body. Measuring tumor size is typically achieved by imaging-based techniques. For example, computed tomography (CT) scan can provide accurate and reliable anatomic information about not only tumor shrinkage or growth but also progression of disease by identifying either growth in existing lesions or the development of new lesions or tumor metastasis.

In yet another approach, a reduction of tumor load can be assessed by functional and metabolic imaging techniques. These techniques can provide earlier assessment of therapy response by observing alterations in perfusion, oxygenation and metabolism. For example, $^{18}$F-FDG PET uses radiolabeled glucose analogue molecules to assess tissue metabolism. Tumors typically have an elevated uptake of glucose, a change in value corresponding to a decrease in tumor tissue metabolism indicates a reduction in tumor load. Similar imaging techniques are disclosed in Kang et al., Korean J. Radiol. (2012) 13(4) 371-390.

A patient receiving the therapy disclosed herein may exhibit varying degrees of tumor load reduction. In some cases, a patient can exhibit a Complete Response (CR), also referred to as "no evidence of disease (NED)". CR means all detectable tumor has disappeared as indicated by tests, physical exams and scans. In some cases, a patient receiving the combination therapy disclosed herein can experience a Partial Response (PR), which roughly corresponds to at least a 50% decrease in the total tumor volume but with evidence of some residual disease still remaining. In some cases the residual disease in a deep partial response may actually be dead tumor or scar so that a few patients classified as having a PR may actually have a CR. Also many patients who show shrinkage during treatment show further shrinkage with continued treatment and may achieve a CR. In some cases, a patient receiving the therapy can experience a Minor Response (MR), which roughtly means a small amount of shrinkage that is more than 25% of total tumor volume but less than the 50% that would make it a PR. In some cases, a patient receiving the therapy can exhibit Stable Disease (SD), which means the tumors stay roughly the same size, but can include either a small amount of growth (typically less than 20 or 25%) or a small amount of shrinkage (Anything less than a PR unless minor responses are broken out. If so, then SD is defined as typically less 25%).

Desired beneficial or desired clinical results from the therapy may also include e.g., reduced (i.e., slowing to some extent and/or stop) cancer cell infiltration into peripheral organs; inhibited (i.e., slowing to some extent and/or stop) tumor metastasis; increased response rates (RR); increased duration of response; relieved to some extent one or more of the symptoms associated with the cancer; decreased dose of other medications required to treat the disease; delayed progression of the disease; and/or prolonged survival of patients and/or improved quality of life. Methods for evaluating these effects are well known and/or disclosed in, e.g., cancerguide.org/endpoints.html and RECIST guidelines, supra.

In some cases, the administration of a Gal3:TIM-3 inhibitor as disclosed herein may reduce tumor burden by at least 20%, at least 30%, at least 40%, or at least 46% within the treatment period.

4. Combination with Other Therapies

In some embodiments, combinations of a Gal3:TIM-3 inhibitor and one or more second anti-cancer agents ("second agents") may be employed to reduce the tumor load in the patient. By "combination therapy" or "in combination with", it is not intended to imply that the therapeutic agents must be administered at the same time and/or formulated for delivery together, although these methods of delivery are within the scope described herein. The Gal3:TIM-3 inhibitor and the second agent can be administered following the same or different dosing regimen. In some embodiments, the Gal3:TIM-3 inhibitor and the second agent are administered sequentially in any order during the entire or portions of the treatment period. In some embodiments, the Gal3:TIM-3 inhibitor and the second anti-cancer agent is administered simultaneously or approximately simultaneously (e.g., within about 1, 5, 10, 15, 20, or 30 minutes of each other). Non-limiting examples of combination therapies are as follows, with administration of the Gal3 and the second anti-cancer agent for example, Gal3:TIM-3 inhibitor is "A" and the second anti-cancer agent or compound, is "B":

|  |  |  |  |  |  |
|---|---|---|---|---|---|
|  | A/B/AB/A/BB/B/AA/A/BA/B/BB/A/AA/B/B | B/A/B/B | | | |
|  | B/B/B/A | B/B/A/B | A/A/B/B | A/B/A/B | A/B/B/A |
| B/B/A/A |  |  |  |  |  |
|  | B/A/B/A | B/A/A/B | A/A/A/B | B/A/A/A | A/B/A/A |
| A/A/B/A |  |  |  |  |  |

Administration of the second anti-cancer agents to a patient will follow general protocols for the administration of such compounds, taking into account the toxicity, if any, of the therapy. The following discloses some exemplar second agents that can be used in combination with the Gal3:TIM-3 inhibitor to treat cancer.

i. Targeted Therapy

In some embodiments, the second anti-cancer agent is a targeted therapeutic agent, i.e., includes agent is against specific molecular or genetic targets, such as those associated with receptor tyrosine kinases.

ii. Chemotherapy and Radiotherapy

Chemotherapeutic agents suitable for use in combination with the Gal3:TIM-3 inhibitors of the invention include agents that have the property of killing cancer cells or inhibiting cancer cell growth. As compared to targeted therapies as described above, chemotherapies function in a non-specific manner, for example, inhibiting the process of cell division known as mitosis, and generally excludes agents that more selectively block extracellular growth signals (i.e. blockers of signal transduction). These agents include, but are not limited to anti-microtubule agents (e.g., taxanes and vinca alkaloids), topoisomerase inhibitors and antimetabolites (e.g., nucleoside analogs acting as such, for example, Gemcitabine), mitotic inhibitors, alkylating agents, antimetabolites, anti-tumor antibiotics, mitotic inhibitors, anthracyclines, intercalating agents, agents capable of interfering with a signal transduction pathway, agents that promote apoptosis, proteosome inhibitors, and alike.

Alkylating agents are most active in the resting phase of the cell. These types of drugs are cell-cycle non-specific. Exemplary alkylating agents that can be used in combination with the GAL3:TIM-3 INHIBITOR of the invention include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Antitumor antibiotics are chemo agents obtained from natural products produced by species of the soil fungus Streptomyces. These drugs act during multiple phases of the cell cycle and are considered cell-cycle specific. There are several types of antitumor antibiotics, including but are not limited to Anthracyclines (e.g., Doxorubicin, Daunorubicin, Epirubicin, Mitoxantrone, and Idarubicin), Chromomycins (e.g., Dactinomycin and Plicamycin), Mitomycin and Bleomycin.

Antimetabolites are types of chemotherapy treatments that are cell-cycle specific. When the cells incorporate these antimetabolite substances into the cellular metabolism, they are unable to divide. These class of chemotherapy agents include folic acid antagonists such as Methotrexate; pyrimidine antagonists such as 5-Fluorouracil, Foxuridine, Cytarabine, Capecitabine, and Gemcitabine; purine antagonists such as 6-Mercaptopurine and 6-Thioguanine; Adenosine deaminase inhibitors such as Cladribine, Fludarabine, Nelarabine and Pentostatin.

Exemplary anthracyclines that can be used in combination with the GAL3:TIM-3 inhibitor of the invention include, e.g., doxorubicin (Adriamycin® and Rubex®); Bleomycin (Lenoxane®); Daunorubicin (dauorubicin hydrochloride, daunomycin, and rubidomycin hydrochloride, Cerubidine®); Daunorubicin liposomal (daunorubicin citrate liposome, DaunoXome®); Mitoxantrone (DHAD, Novantrone®); Epirubicin (Ellence); Idarubicin (Idamycin®, Idamycin PFS®); Mitomycin C (Mutamycin®); Geldanamycin; Herbimycin; Ravidomycin; and Desacetylravidomycin.

Antimicrotubule agents include vinca alkaloids and taxanes. Exemplary vinca alkaloids that can be used in combination with the GAL3:TIM-3 INHIBITOR of the invention include, but are not limited to, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®). Exemplary taxanes that can be used in combination with the GAL3:TIM-3 inhibitor of the invention include, but are not limited to paclitaxel and docetaxel. Non-limiting examples of paclitaxel agents include nanoparticle albumin-bound paclitaxel (ABRAXANE, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG105 (Angiopep-2 bound to three molecules of paclitaxel, marketed by ImmunoGen), paclitaxel-EC-1 (paclitaxel bound to the erbB2-recognizing peptide EC-1; see Li et al., Biopolymers (2007) 87:225-230), and glucose-conjugated paclitaxel (e.g., 2'-paclitaxel methyl 2-glucopyranosyl succinate, see Liu et al., Bioorganic & Medicinal Chemistry Letters (2007) 17:617-620).

Exemplary proteosome inhibitors that can be used in combination with the GAL3:TIM-3 inhibitor of the invention, include, but are not limited to, Bortezomib (Velcade®); Carfilzomib (PX-171-007, (S)-4-Methyl-N—((S)-1-(((S)-4-methyl-1-((R)-2-methyloxiran-2-yl)-1-oxope-ntan-2-yl)amino)-1-oxo-3-phenylpropan-2-yl)-2-((S)-2-(2-morpholinoacetamid-o)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(-2R)-2-methyl-2-oxiranyl]-2-oxo-1-(phenylmethy)ethyl]-L-serinamide (ONX-0912).

In some embodiments, the chemotherapeutic agent is selected from the group consisting of chlorambucil, cyclophosphamide, ifosfamide, melphalan, streptozocin, carmustine, lomustine, bendamustine, uramustine, estramustine, carmustine, nimustine, ranimustine, mannosulfan busulfan, dacarbazine, temozolomide, thiotepa, altretamine, 5-fluorouracil (5-FU), 6-mercaptopurine (6-MP), capecitabine, cytarabine, floxuridine, fludarabine, gemcitabine, hydroxyurea, methotrexate, pemetrexed, daunorubicin, doxorubicin, epirubicin, idarubicin, SN-38, ARC, NPC, campothecin, topotecan, 9-nitrocamptothecin, 9-aminocamptothecin, rubifen, gimatecan, diflomotecan, BN80927, DX-895 If, MAG-CPT, amsacrine, etoposide, etoposide phosphate, teniposide, doxorubicin, paclitaxel, docetaxel, gemcitabine, accatin III, 10-deacetyltaxol, 7-xylosyl-10-deacetyltaxol, cephalomannine, 10-deacetyl-7-epitaxol, 7-epitaxol, 10-deacetylbaccatin III, 10-deacetyl cephalomannine, gemcitabine, Irinotecan, albumin-bound paclitaxel, Oxaliplatin, Capecitabine, Cisplatin, docetaxel, irinotecan liposome, and etoposide, and combinations thereof.

In certain embodiments, the chemotherapeutic agent is administered at a dose and a schedule that may be guided by doses and schedules approved by the U.S. Food and Drug Administration (FDA) or other regulatory body, subject to empirical optimization.

In still further embodiments, more than one chemotherapeutic agent may be administered simultaneously, or sequentially in any order during the entire or portions of the treatment period. The two agents may be administered following the same or different dosing regimens.

Radiotherapy requires maximized exposure of the affected tissues while sparing normal surrounding tissues. Interstitial therapy, where needles containing a radioactive source are embedded in the tumor, has become a valuable new approach. In this way, large doses of radiation can be delivered locally while sparing the surrounding normal structures. Intraoperative radiotherapy, where the beam is placed directly onto the tumor during surgery while normal structures are moved safely away from the beam, is another specialized radiation technique. Again, this achieves effective irradiation of the tumor while limiting exposure to surrounding structures. Despite the obvious advantage of approaches predicated upon local control of the irradiation, patient survival rate is still very low.

iii. Others Therapies

The present methods involving Gal3:TIM-3 inhibitor can be combined with other means of treatment such as surgery, radiation, and/or hormonal therapy. Hormonal therapies can inhibit growth-promoting signals coming from classic endocrine hormones, for example, primarily estrogens for breast cancer and androgens for prostate cancer.

5. Pharmaceutical Compositions

The Gal3:TIM-3 inhibitors disclosed herein are useful in the manufacture of a pharmaceutical composition or a medicament for treating inflammatory diseases as described above. Pharmaceutical compositions or medicaments for use in the present invention can be formulated by standard techniques using one or more physiologically acceptable carriers or excipients. Suitable pharmaceutical carriers are described herein and in, e.g., "Remington's Pharmaceutical Sciences" by E. W. Martin. Gal3:TIM-3 inhibitor of the present invention and their physiologically acceptable salts and solvates can be formulated for administration by any suitable route, including, but not limited to, orally, topically, nasally, rectally, parenterally (e.g., intravenously, subcutaneously, intramuscularly, etc.), and combinations thereof. In some embodiments, the therapeutic agent is dissolved in a liquid, for example, water.

For oral administration, a pharmaceutical composition or a medicament disclosed herein can take the form of, e.g., a tablet or a capsule prepared by conventional means. Preferred are tablets and gelatin capsules comprising the active ingredient(s), together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, anhydrous colloidal silica, talcum, stearic acid, its magnesium or calcium salt (e.g., magnesium stearate or calcium stearate), metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulfate, and/or (f) absorbents, colorants, flavors and sweeteners. In some embodiments, the tablet contains a mixture of hydroxypropyl methylcellulose, polyethyleneglycol 6000 and titatium dioxide. vTablets may be either film coated or enteric coated according to methods known in the art.

Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For topical administration, the compositions of the present invention can be in the form of emulsions, lotions, gels, creams, jellies, solutions, suspensions, ointments, and transdermal patches. For delivery by inhalation, the composition can be delivered as a dry powder or in liquid form via a nebulizer. For parenteral administration, the compositions can be in the form of sterile injectable solutions and sterile packaged powders. Preferably, injectable solutions are formulated at a pH of about 4.5 to about 7.5.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

The compounds can be encapsulated in a controlled drug-delivery system such as a pressure controlled delivery capsule (see, e.g., Takaya et al., J. Control Rel., 50:111-122 (1998)), a colon targeted delivery system, a osmotic controlled drug delivery system, and the like. The pressure controlled delivery capsule can contain an ethylcellulose membrane. The colon target delivery system can contain a tablet core containing lactulose which is overcoated with an acid soluble material, e.g., Eudragit E®, and then overcoated with an enteric material, e.g., Eudragit L®. The osmotic controlled drug delivery system can be a single or more osmotic unit encapsulated with a hard gelatin capsule (e.g., capsule osmotic pump; commercially available from, e.g., Alzet, Cupertino, Calif.). Typically, the osmotic unit contains an osmotic push layer and a drug layer, both surrounded by a semipermeable membrane.

6. Dosage

Pharmaceutical compositions or medicaments can be administered to a subject at a therapeutically effective dose to treat the cancers as described herein. In some embodiments, the pharmaceutical composition or medicament is administered to a subject in an amount sufficient to elicit an effective therapeutic response in the subject.

Dose administered will vary depending on a number of factors, including, but not limited to, the subject's body weight, age, individual condition, surface area or volume of the area to be treated, and/or on the form of administration. The size of the dose also will be determined by the existence, nature, and extent of any adverse effects that accompany the administration of a particular compound in a particular subject. Preferably, the smallest dose and concentration required to produce the desired result should be used. Dosage should be appropriately adjusted for children, the elderly, debilitated patients, and patients with cardiac and/or liver disease. Further guidance can be obtained from studies known in the art using experimental animal models for evaluating dosage.

Dosage regimens are adjusted to provide the optimum desired response, e.g., a therapeutic response or minimal adverse effects. For administration of a Gal3:TIM-3 inhibitor antibody, the dosage ranges from about 0.0001 to about 100 mg/kg, usually from about 0.001 to about 20 mg/kg, or about 0.01 to about 40 mg/kg, and more usually from about 0.01 to about 10 mg/kg, of the subject's body weight. Preferably, the dosage is within the range of 0.1-10 mg/kg body weight. For example, dosages can be 0.1, 0.3, 1, 3, 5 or 10 mg/kg body weight, and more preferably, 0.3, 1, 3, or 10 mg/kg body weight.

The dosing schedule is typically designed to achieve exposures that result in sustained receptor occupancy (RO) based on typical pharmacokinetic properties of an Ab. An exemplary treatment regime entails administration once per week, once every two weeks, once every three weeks, once every four weeks, once a month, once every 3 months or once every three to 6 months. The dosage and scheduling may change during a course of treatment. For example, dosing schedule may comprise administering the Ab: (i) every two weeks in 6-week cycles; (ii) every four weeks for six dosages, then every three months; (iii) every three weeks; (iv) 3-10 mg/kg body weight once followed by 1 mg/kg body weight every 2-3 weeks. Considering that an IgG4 Ab typically has a half-life of 2-3 weeks, a preferred dosage regimen for a Gal3:TIM-3 inhibitor of the invention comprises 0.3-10 mg/kg body weight, preferably 3-10 mg/kg body weight, more preferably 3 mg/kg body weight via intravenous administration, with the Ab being given every 14 days in up to 6-week or 12-week cycles until complete response or confirmed progressive disease.

In some cases, two or more antibodies with different binding specificities are administered simultaneously, in which case the dosage of each Ab administered falls within the ranges indicated. Antibody is usually administered on multiple occasions. Intervals between single dosages can be, for example, weekly, every 2 weeks, every 3 weeks, monthly, every three months or yearly. Intervals can also be irregular as indicated by measuring blood levels of Ab to the target antigen in the patient. In some methods, dosage is adjusted to achieve a plasma Ab concentration of about 1-1000 mg/ml and in some methods about 25-300 mg/ml.

In some cases, the Gal3:TIM-3 inhibitor is a compound and may be administered for multiple days at the therapeutically effective daily dose and the treatment may continue for a period ranging from three days to two weeks or longer. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every day, every other day, or, if higher dose ranges are employed and tolerated by the subject, twice a week.

In some embodiments, the disclosure provides a unit dosage for oral administration to an individual of about 50 to 70 kg may contain between about 20 and 300 mg of the active ingredient. Typically, a dosage of the Gal3:TIM-3 is a dosage that is sufficient to achieve the desired effect. Optimal dosing schedules can be calculated from measurements of agent accumulation in the body of a subject. In general, dosage may be given once or more daily, weekly, or monthly. Persons of ordinary skill in the art can easily determine optimum dosages, dosing methodologies, and repetition rates.

Thus, in some embodiments, the pharmaceutical composition provided herein is a sterile solution comprising an antibody that is able to interfere with the interaction between the Gal3 and TIM-3 on T cells in a cancer patient, the solution comprising 10 μg-100 mg, e.g., 10 μg-40 mg, 100 μg-40 mg, or 1 mg-10 mg of antibody per kilogram of patient body weight in a solution of 100 ml suitable for intravenous delivery over a time period, e.g., 1-4 hour period. The antibody in the sterile solution can be an anti-Gal3 antibody or an anti-TIM-3 antibody. In some embodiments, the sterile solution further comprises one or more the targeted therapy agents, e.g., one or more check point inhibitor therapy agents as described above. In some embodiments, the sterile solution further comprises one or more nanoparticles having a diameter between 10 and 100 nm, e.g., between 40 and 100 nm, or between 50 and 80 nm.

In some embodiments, the compositions of the invention are administered for one or more weeks, e.g., 1, 2, 3, 4, 5, 6, 7, 8, 9, 10, 11, 12, 13, 14, or more weeks. In yet other embodiments, the compounds are administered for one or more months, e.g., 1, 2, 3, 4, 5, 6, 7, 8, 9, 10, 11, 12, or more months.

Alternatively, the Ab can be administered as a sustained release formulation, in which case less frequent administration is required. Dosage and frequency vary depending on the half-life of the Ab in the patient. In general, human Abs shows the longest half-life, followed by humanized Abs, chimeric Abs, and nonhuman Abs. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

The dosage of a composition of the present invention can be monitored and adjusted throughout treatment, depending on severity of symptoms, frequency of recurrence, and/or the physiological response to the therapeutic regimen. Those of skill in the art commonly engage in such adjustments in therapeutic regimens.

Non-Limiting Exemplary Embodiments

This invention is further illustrated by the following, non-limiting, exemplary embodiments.
1. A method of activating immune response in a patient comprising administering to the patient a Gal3:TIM-3 inhibitor that interferes with the interaction between Gal3 and TIM-3 in the patient, where said inhibitor is administered in an amount sufficient to activate immune response.
2. The method of embodiment 1, wherein the TIM-3 is expressed on immune cells in the patient.
3. The method of any of the preceding embodiments, wherein the patient hosts a cancer, wherein the interaction between Gal3 and TIM-3 occurs in a tumor microenvironment and the Gal3:TIM-3 inhibitor is administered in an amount sufficient to decrease the cancer load of the patient.
4. The method of embodiment 3, wherein the cancer comprises cells in a tumor microenvironment, wherein the cells overexpress Gal3 on their surface.
5. A method of activating immune response in a patient hosting a cancer comprising cells in a tumor microenvironment, wherein the cells overexpress Gal3 on the their surface, the method comprising administering to the patient a Gal3:TIM-3 inhibitor that interferes with the interaction between the Gal3 and TIM-3 on the immune cells in the tumor microenvironment wherein said inhibitor is administered in an amount sufficient to decrease the cancer load of the patient by activating the immune response.
6. The method of embodiment 2 or 5, wherein immune cells are T cells and/or NK cells.
7. A method of any of embodiments 3-5, wherein the cancer is a metastatic cancer or primary cancer.
8. The method of any of the preceding embodiments, wherein the inhibitor binds to TIM-3.
9. The method of any of the preceding embodiments, wherein the inhibitor binds to Gal3.
10. The method of any of the preceding embodiments, wherein the TIM-3:Gal3 inhibitor is an antibody.
11. The method of embodiment 5, wherein the antibody recognizes a peptide comprising a sequence selected from the group consisting of SEQ ID NOs: 5-8.
12. The method of embodiment 5, wherein the antibody is a single chain antibody or a Fab.
13. The method of embodiment 5, wherein the antibody is a humanized antibody or a human antibody.
14. The method of any of the preceding embodiments, wherein the administering of the Gal3:TIM-3 inhibitor is by intravenous infusion.
15. The method of any of the preceding embodiments, wherein the Gal3:TIM-3 inhibitor is administered in combination with one or more other therapies.
16. The method of embodiment 15, wherein the one or more other therapies are selected from the group consisting of a chemotherapy, a radiotherapy, a checkpoint inhibitor therapy.
17. The method of embodiment 15 or 16, wherein the checkpoint inhibitor therapy is selected from the group consisting of an anti-PD-1 therapy and an anti-CTLA4 therapy.
18. The method of any of the preceding embodiments, wherein the administration of the inhibitor is administered a dose of between 100 μg/kg to 40 mg/kg body weight every other week.
19. A method for determining if a patient's cancer is suitable for treatment with a Gal3:TIM-3 inhibitor, said method comprising:
    combining cells obtained from a tumor microenvironment of a known type from a patient with an antibody specific for the Gal3;
    determining the level of Gal3 on the cells;
    comparing the level of Gal3 on the surface of the cells with a first threshold activity value of Gal3; and
    determining the patient's cancer as suitable for treatment with a Gal3:TIM-3 inhibitor if the level of Gal3 on the surface of the cells is higher than the first threshold activity value.
20. The method of embodiment 19, wherein the first threshold activity value of Gal3 is derived from a cohort of at least 100 test individuals with the same type of cancer as the patient.
21. The method of embodiment 20, wherein the determining the patient's cancer as suitable for treatment step further comprises determining if the level of Gal3 on the surface of the cells obtained from the tumor microenvironment is 25% or greater as compared to a second threshold activity value of Gal3, wherein the second threshold activity value is derived from samples comprising corresponding cells from healthy patients.
22. The method of any of embodiments 19-21, wherein the cells obtained from the tumor microenvironment comprises at least cancer cells and/or tumor-associated macrophages.

23. The method of embodiment 21, wherein the determining the patient's cancer as suitable for treatment step further comprises determining if the level of Gal3 on the surface of the cells obtained from the tumor microenvironment is 75% or greater as compared to the second threshold activity value.

24. A sterile solution that is able to interfere with the interaction between the Gal3 and TIM-3 on T-cells in a cancer patient, where the solution comprises between 10 μg and 100 mg of antibody per kilogram of patient body weight in a solution of 100 ml suitable for intravenous delivery over a 1-4 hour period, wherein the antibody can interfere with the interaction between the Gal3 and TIM-3 on the T-cells.

25. The sterile solution of embodiment 23, wherein the sterile solution further comprises one or more other checkpoint inhibitor antibodies.

26. The sterile solution of embodiment 23, wherein one or more other checkpoint inhibitor antibodies is selected from the group consisting of anti PD-1 and anti CTLA-4 antibodies.

27. The sterile solution of any of embodiments 23-25, wherein the sterile solution further comprises a nanoparticles of between 10 and 100 nm in diameter.

28. The sterile solution of embodiment 23, wherein the antibody is an anti-Gal3 antibody.

29. The sterile solution of embodiment 23, wherein the antibody is an anti-TIM-3 antibody.

30. A method of producing an anti-Gal3 antibody that can interfere with the interaction between Gal3 and TIM-3, the method comprising: introducing a peptide comprising a sequence selected from the group consisting of SEQ ID NOs: 5-8 to an animal, wherein the animal produces the Gal3 antibody.

31. A humanized or chimeric anti-Gal3 antibody, wherein the antibody comprises
(1) a light chain variable region comprising a complementary determining region (CDR) L1, a CDR L2, and a CDR L3 and (2) a heavy chain variable region comprising a CDR H1, a CDR H2, and a CDR H3, wherein
the CDR L1 comprises the amino acid sequence of SEQ ID NO:17,
the CDR L2 comprises the amino acid sequence of SEQ ID NO:18,
the CDR L3 comprises the amino acid sequence of SEQ ID NO:19,
the CDR H1 comprises the amino acid sequence of SEQ ID NO:9,
the CDR H2 comprises the amino acid of SEQ ID NO:10, and
the CDR H3 comprises the amino acid sequence of SEQ ID NO:11.

32. The humanized or chimeric anti-Gal3 antibody of embodiment 31, wherein the heavy chain variable region has a sequence having at least 90% identity to the amino acid sequence of SEQ ID NO: 25.

33. The humanized or chimeric anti-Gal3 antibody of embodiment 31 or 32, wherein the light chain variable region has a sequence having at least 90% identity to the amino acid sequence of SEQ ID NO: 26.

34. A method of selecting compounds that can block interaction between Gal3 and TIM-3, activating immune response and/or treating cancer in a patient comprising
(a) contacting a library of compounds with Gal3 and TIM-3, and
(b) selecting one or more candidate compounds from the library that are capable of blocking the interaction between Gal3 and TIM-3.

35. The method of embodiment 34, further comprising
(c) contacting the one or more candidate compounds selected from step (b) with a mixture comprising T cells, and allogeneic antigen presenting cells, and identifying one or more compounds that are capable of stimulating the T cells, and/or
(d) administering the one or more candidate compounds selected from (b) to a mammal hosting a tumor and identifying one or more compounds that are capable of reducing tumor load of the mammal, and optionally
(e) administering an effective amount of a compound that is capable of stimulating the T cells and/or capable of reducing tumor load of the mammal to the patient, thereby activating immune response and/or treating cancer in the patient.

36. The method of embodiment 35, wherein the compounds are antibodies.

37. A method of activating immune response in a patient comprising administering to the patient a Gal3:TIM-3 inhibitor that interferes with the interaction between Gal3 and TIM-3, wherein said inhibitor is administered in an amount sufficient to activate immune response, wherein the inhibitor comprises the humanized antibody of any embodiment of embodiments 31-33.

38. A method of activating immune response in a patient comprising administering to the patient an antibody, wherein the antibody includes a means for inhibiting the interaction between Gal3 and TIM-3.

39. The method of embodiment 38, wherein the antibody further includes a means for binding Gal3 or TIM-3.

EXAMPLES

The present invention is described by reference to the following Examples, which are offered by way of illustration and are not intended to limit the invention in any manner. Unless otherwise stated, standard techniques well known in the art or the techniques specifically described below were utilized.

Example 1. Generation Of Gal3-Overexpressing Cell Lines

A20, a mouse B lymphoma cell line, obtained from American Tissue and cell culture Collection (ATCC, Manassas, Va.), was transfected with nucleic acid construct encoding a Flag-tagged human Gal3 protein or a Flag-tagged human PDL1 protein. The constructs additionally contain an antibiotics-resistant marker. The transformed cells were selected based on the antibiotics resistance to create A20 cells stably expressing the Flag-tagged human Gal3 protein (A20 Gal3 cells) or A20 cells stably expressing the Flag-tagged human PDL1 protein (A20 hPDL1 cells).

Example 2. Gal3 Specifically Binds to TIM-3

This example describes various assays that have been conducted to evaluate the interaction between Gal3 and TIM-3.

Binding Assays—Co-Immunoprecipitation

Co-immunoprecipitation experiments were performed to test whether TIM-3 specifically interacts with Gal3. 293T cells were co-transfected with a plasmid encoding HA-tagged TIM-3 and a plasmid encoding Flag-tagged Gal3, Flag-tagged Gal9, or Flag-tagged CEACAM1. The transfection was performed using lipofectamine 3000 (Waltham, Mass.) following manufacturer's protocols. The transfected cells were grown over night and then washed and lysed in 1 ml lysis buffer. The lysed cells were centrifuged and supernatant (the lysate) was collected. The lysates were prepared and separated on SDS PAGE and probed with anti-HA (FIG. 1A) and anti-Flag antibodies (FIG. 1B), respectively. Both the anti-Flag and the anti-HA antibodies were purchased from Sigma. The arrows in FIGS. 1A and 1B indicate the presence of the various proteins.

For immunoprecipitation, anti-Flag agarose beads (Abcam, Cambridge, Mass.) were added to the supernatant (the lysate) produced above. The beads and the lysates were incubated by rotating at 4° C. overnight to allow the Flag-tagged proteins to attach. The beads were then washed 3× with lysis buffer and mixed with 1×SDS PAGE sample buffer, boiled and separated on SDS-PAGE. The SDS-PAGE gel was transferred onto a membrane which was probed with ant-HA antibody (FIG. 1C). In FIGS. 1A-1C, lanes 1-3 represents the results from lysate produced from the cells co-transfected with a plasmid encoding HA-tagged TIM-3 and a plasmid encoding Flag-tagged Gal3; cells co-transfected with a plasmid encoding HA-tagged TIM-3 and a plasmid encoding Flag-tagged Gal9, or cells co-transfected with a plasmid encoding HA-tagged TIM-3 and a plasmid encoding Flag-tagged CEACAM1, respectively.

The results, as shown in FIG. 1, indicate that human Gal3 specifically pulled down human TIM-3, while human CEACAM1 was not able to pull down the HA-tagged human TIM-3. Although it appeared that human Gal9 also pulled down human TIM-3 (lane 2 of FIG. 1C), this appeared to be non-specific due to Gal9 protein aggregation—the molecular weight of Gal9 appears to be much larger than it actual size of 40kD. The conclusion that the interaction between Gal9 and TIM-3 is non-specific in nature is also supported by the evidence shown in FIG. 5B, below.

Figure 2:
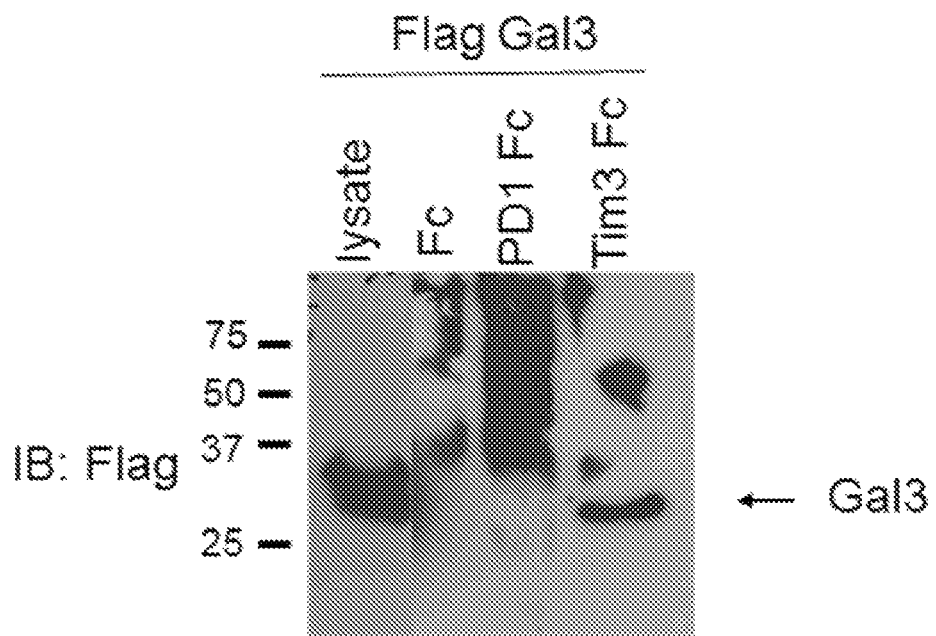
FIG. 2 shows the results of pull-down assays using a fusion protein composed of a hTIM-3 extracellular domain fused with the Fc portion of hIgG (hTIM-3 Fc). The results show that the binding between Gal3 and TIM-3 was specific. As shown in this figure, hTIM-3 Fc, but not hFc or hPD1 Fc, pulled down the over-expressed, Flag-tagged hGal3 protein from 293T cells.
Figure 3:
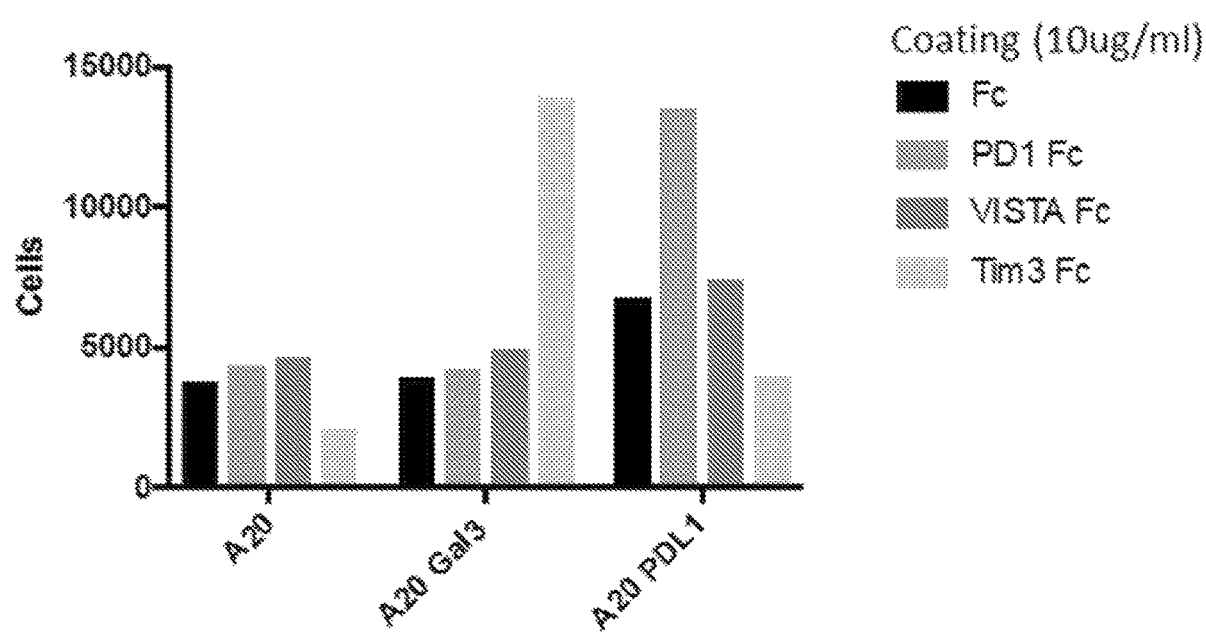
FIG. 3 shows the results of cell adhesion assay indicating the specific interaction between hGal3 and hTim3. As shown in the figure, a significantly higher number of A20 cells expressing hGal3 (A20 Gal3 cells) were able to adhere to plates coated with hTIM-3 Fc than to plates coated with hVISTA Fc or hPD1 Fc. The results also indicate that a higher number of A20 PDL1 cells were able to adhere to plates coated with hPD1 Fc than to plates coated with human VISTA Fc (hVISTA Fc) or plates coated with hTIM-3 Fc.

Additional co-immunoprecipitation experiments were performed to test if Gal3 specifically interacts with TIM-3. Flag-human Gal3 plasmid (OriGene, Rockville, Md.) was transfected into 293T cells, which were at 80% confluency. The transfections were performed in 10 cm plates using lipofectamine 3000 as described above. After overnight transfection, the cells were replaced on 10 cm plates that had been coated with human Fc, human PD1-Fc, or human TIM-3 Fc for 3 hours. The cells were washed once in 1×PBS, and then lysed in 1 ml lysis buffer. Cell lysates were collected and centrifuged. Protein G beads was added to the supernatant formed after the centrifugation and incubated by rotating at 4° C. for 4 hours. The beads were then washed 3× with lysis buffer, followed by addition of 1×SDS PAGE sample buffer. The samples containing the beads were boiled and separated on SDS-PAGE, transferred onto membrane. The membrane was then probed with ant-Flag antibodies. As shown in FIG. 2, human TIM-3 specifically pulled down Flag-tagged Gal3. In contrast, neither human Fc nor human PD1 Fc was able to pull down TIM-3. This shows that Gal3 does not bind to Fc or PD1 Fc and that the binding between Gal3 and TIM-3 is specific.

Binding Assays—Cell Adhesion Assay

Next, cell adhesion assays were performed to confirm the binding of Gal3 and TIM-3. In this experiment, 96-well plates were coated with human Fc, human PD1-Fc, human VISTA-Fc, human TIM-3-Fc at 4° C. overnight, then blocked with 2% BSA in PBS at 37° C. for 2 hours. A20, A20 cells overexpressing human Gal3 (A20 Gal3), or A20 cells overexpressing human PDL1 (A20 PDL1) cells were seeded into the wells that were coated with the various Fc proteins as described above. The plates were then centrifuged at 720 rpm and then were stopped. The plates were incubated at 37° C. for 30 minutes and then submerged into PBS. The plates were slowly flipped 180 degrees and kept at the flipped position for 30 min. After plates were flipped back and removed from PBS, 200 µl solution from each well was removed and discarded and the remaining solution, about 100 µl in volume, was transfer into a 96-well plate. The cells were counted by flow cytometry analysis.

The results show that the number of A20 expressing human Gal3 (A20 Gal3) cells that were adhered to human TIM-3 Fc coated plates were significantly greater than that of the cells adhered to plates coated with human VISTA Fc or human PD1 Fc. As expected, since PDL1 is a known ligand for PD1, the number of A20 PDL1 cells that were shown to be adhered to hPD1 Fc was significantly greater than those adhered to plates coated with human VISTA Fc or human TIM-3 Fc. These results further confirmed the interaction between Gal3 and TIM-3 is specific.

Blocking Assays—Flow Cytometry

Flow cytometry analysis was performed to evaluate the binding between TIM-3 and Gal3 using A20 cells. A20 Gal3 cells were incubated with 10% FBS HBSS solution that contains with or without mouse TIM-3 Fc on ice for 20 minutes. There are five experimental groups: in group 1, A20 Gal3 cells were incubated without mTIM-3 Fc protein as control; in group 2, A20 Gal3 cells were incubated with mTIM-3 Fc protein; in groups 3, 4, 5, in addition to mTIM-3 Fc protein, anti-mouse TIM-3 polyclonal antibody (R&D System, Minneapolis, Minn.) (group 3), monoclonal antibody RMT3-23 (Bio X cell, West Lebanon, N.H.) (group 4), monoclonal antibody 215015 (R&D Systems) (group 5), were also added to test if these antibodies could block Gal3 and Tim3 binding. For blocking, cells were incubated with 10% FBS HBSS containing mentioned antibodies, then were added with 10% FBS HBSS containing mTIM-3 Fc for 20 min. Samples were centrifuged and pellet were added 10% FBS HBSS containing APC conjugated anti-hFc antibodies (Jackson ImmunoResearch, West Grove, Pa.) for 20 min. After spinning, live/dead cells were stained with Violet dead cell stain kit (Life Technologies). Stained cells were subjected to flow analysis.

FIG. 4 shows that mTIM-3 was able to bind to dead cells and the Gal 3 protein on live cells and that Gal3 and dead cells bind different epitopes on TIM-3. In this assay, TIM-3 Fc binds both dead cells (FIG. 4C, row 2) and Gal3 expressed on live cells (FIG. 4B, row 2). However, mTIM-3 monoclonal antibody RMT3-23 blocked the binding of TIM-3 to dead cells (FIG. 4C, row 4), but not to Gal3 expressed on live cells (FIG. 4B, row 4). This shows that the Gal3 and dead cells bind to different epitopes on TIM-3. As controls, neither mTIM-3 polyclonal antibody nor monoclonal antibody 215015 (R&D System, Minneapolis, Minn.) has any effect on Tim3 binding to Gal3 (FIG. 4B, rows 3 and 5) or to dead cells (FIG. 4C, row 3 and 5), respectively.

Blocking Assays—ELISA

Figure 5A:
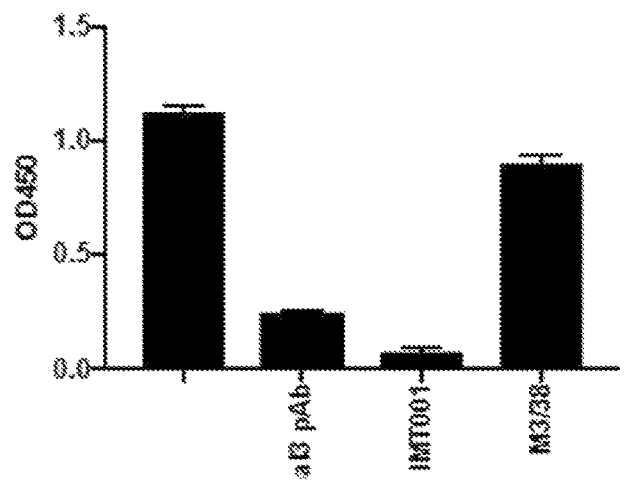
FIGS. 5A-5C show the ELISA results indicating the specific binding of Gal3 on TIM-3.

ELISA assays were also performed to test the interaction between Gal3 and TIM-3. 96 well ELISA plates (ThermoFisher Scientific) were coated with mouse Gal3 protein (BioLegend, San Diego, Calif.) in PBS or human Gal9 protein (R&D systems) in PBS or phosphatidylserine (PS) (Sigma) in ethanol and incubated at 4° C. for overnight. The plate was washed three times with TBST and then blocked with PBS buffer containing 2% BSA at room temperature for 1 hour. In FIG. 5A, different anti Gal3 antibodies, i.e. mGal3 polyclonal antibody (R&D sytems), mAb IMT001, mAb M3/38 (Thermofisher Scientific) (FIG. 5A), were added to well that has been coated with Gal3. The antibodies were incubated for 10 minutes and mouse TIM-3 Fc were then added to the plates and incubated for an additional one-hour incubation. Plates were then washed for three times and followed by incubation with anti human-IgG-HRP (Jackson ImmunoResearch) for 1 h at room temperature. The color was developed with TMB subtract (GeneTex, Irvine, Calif.) after three time washes with TBST and the reaction was terminated with 1N HCl. The optical density (OD) was read at 450 nm. The results were expressed as the average OD of duplicates±SD. The results in FIG. 5A showed that among all antibodies tested, mouse Gal3 polyclonal antibody and monoclonal antibody IMT001 blocked the interaction between Gal3 and TIM-3 (FIG. 5A).

Figure 5B:
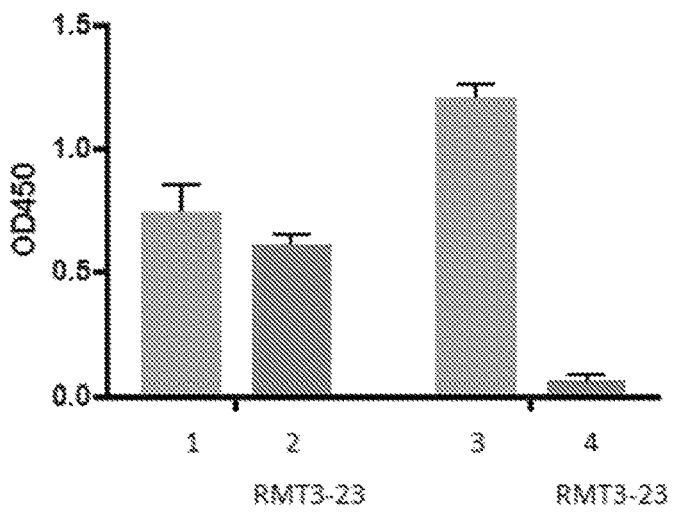

In FIG. 5B, mouse Gal3 protein (BioLegend) in PBS (groups 1 and 2) or PS (Sigma-Aldrich, St. Louis, Mo.) in ethanol (groups 3 and 4) were coated on the plates and incubated at 4° C. overnight. Anti mTIM-3 mouse antibodies, mAb RMT3-23 (Bio X cell), was added to the coated plates for groups 2 and 4 only. Secondary anti human-IgG-HRP antibody and substrates were added as described above to detect the binding of the mTIM-3 to mGal3 or PS. The results showed a dramatic reduction in signal in group 4 as compared to group 3, indicating that RMT3-23 blocked PS from binding to TIM-3; meanwhile the results showed no significant reduction in signal in group 2 as compared to group 1, indicating that RMT3-23 did not block Gal3 from binding to TIM-3. Since TIM-3 binds to dead cells through its interaction with PS externalized and exposed on dead cell surface, these experiments corroborated the observations in FIGS. 4A-4C that Gal3 and PS bind to different epitopes on TIM-3.

Figure 5C:
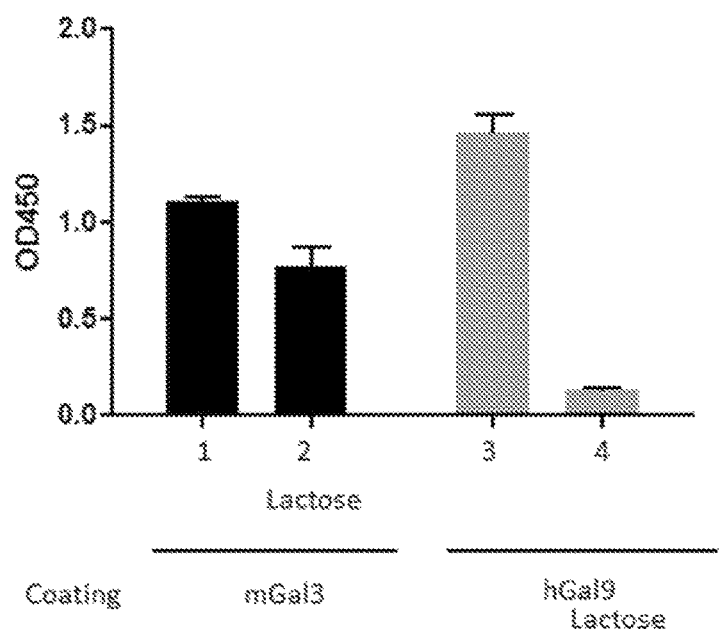

For sugar-dependence assay, ELISA plates were coated with either mGal3 (groups 1 and 2, or hGal9 (groups 3 and 4). Mouse TIM-3 Fc protein (R&D systems) was added to the coated ELISA plates with (groups 2 and 4) or without (groups 1 and 3) 25 mM of α-Lactose (Sigma-Aldrich) at room temperature for 1 h. Secondary anti human-IgG-HRP antibody and substrates were added as described above to detect the binding of mTIM-3-Fc to mGal3 or hGal9. FIG. 5C showed that lactose blocked Gal9 from binding to TIM-3, as shown by a dramatic, more than 10 fold reduction in signal in group 4 (lactose is present) as compared to group 3 (lactose is absent), indicating sugar dependent binding between Gal9 and TIM-3. In contrast, while lactose's blocking effect on Gal3 from binding to TIM-3 was minimal—there was no significant difference in signal produced from the binding of TIM-3 and Gal3 between group 2 (lactose was present) and group 1 (lactose was absent). This shows that the interaction between Gal3 and TIM-3 was not affected by the presence of sugar, i.e., the interaction was sugar-independent.

Example 3. Overexpress Gal3 Suppresses T Cell Activation

This example describes experiments that were conducted to evaluate the functional properties of overexpression of Gal3 in A20 cells.

Figure 6A:
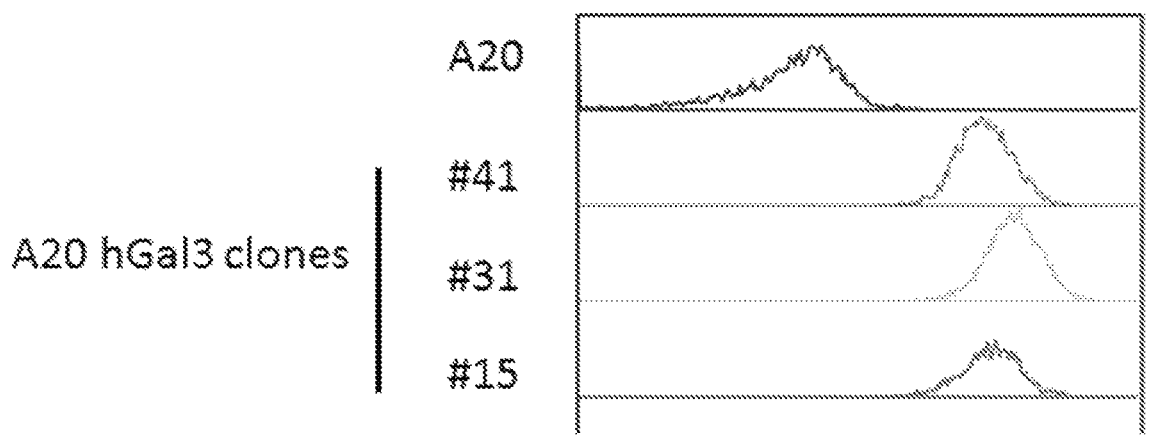
FIGS. 6A and 6B show that over-expressed Gal3 suppressed T cell activation.
Figure 6B:
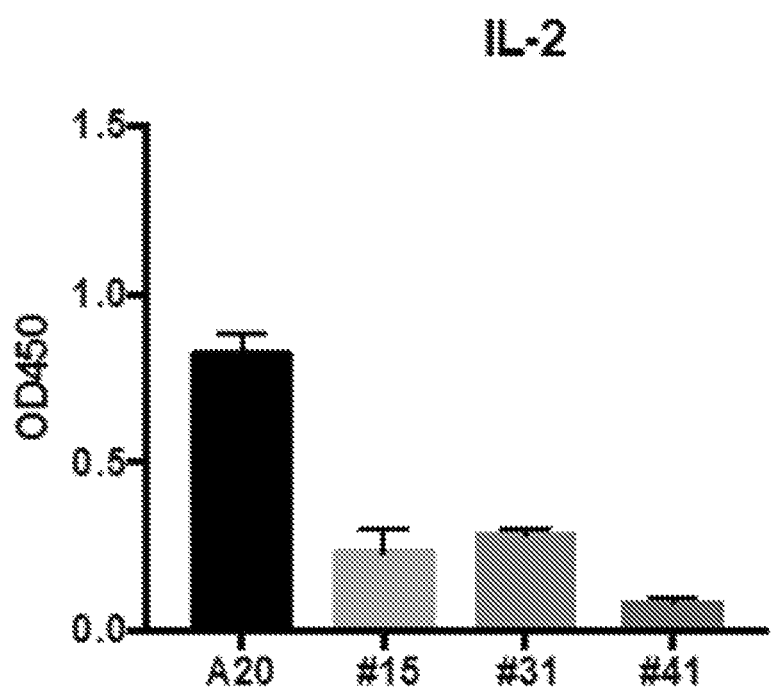

A20 clones, #41, #31, and #15, stably overexpressing hGal3 were generated as described above. FIG. 6A shows results of flow cytometry analysis that shows hGal3 expression level in these clones. Cells of A20 or the A20 Gal3 clones were mixed with mouse DO11.10 T cells. The mixture was placed to each well of flat 96-well plates and OVA323-339 peptide (Invivogen, San Diego, Calif.) was then added to the plates. After overnight incubation, supernatant was used for measuring IL-2 production of the T cells by ELISA (Thermo Fisher Scientific). As shown in FIG. 6B, the IL-2 production by the mouse DO11.10 T cells were significantly reduced when mixed with any of the three mouse A20 cell clones as compared to when the T cells were mixed with parental A20 cells (FIG. 6B).

Example 4. An Anti-Gal3 Antibody Shows Anti-Tumor Activity in Mouse Lung Metastasis Model The experiments in this example were conducted to evaluate the anti-tumor efficacy of Gal3:TIM-3 inhibitor in vivo. The animal experiments were conducted according to a protocol approved by the Molecular Medicine Research Institute Institutional Animal Care and Use Committee. C57BL/6 mice were placed in a facility accredited by the Association for Assessment and Accreditation of Laboratory Animal Care upon arrival. Thirty six of 7-week old female mice were randomly assigned into three groups (n=12). On day 0, B16F10 cells ($2\times10^5$ in 0.1 mL PBS) were washed and resuspended in PBS before injection into the tail veins of mice using a syringe with a 27-ga needle. Following injection of the B16F10 cells, the animals were administrated intraperitoneally with 10 mg/Kg of mouse IgG2b (Bio X Cell, West Lebanon, N.H.) on day 0, 3, 7 and 10, mPD1 antibody (Bio X Cell, West Lebanon, N.H.) on day 0, 3 and 7 or Gal3 antibody IMT001 on day 0, 3, 7, 10 and 15. The Gal3 antibody clone IMT001 used in this experiment that recognizes an epitope (SEQ ID NO: 5) on Gal3. On day 21, the animals were humanely sacrificed and lung tissues were removed and fixed in a 10% buffered formaldehyde solution. The number of black metastatic colonies on one surface of the left lobes in the lungs were counted (FIG. 7B). Results were expressed as mean±SEM. The statistical analysis was performed in comparison with IgG control group using one-way ANOVA.

Figure 7A:
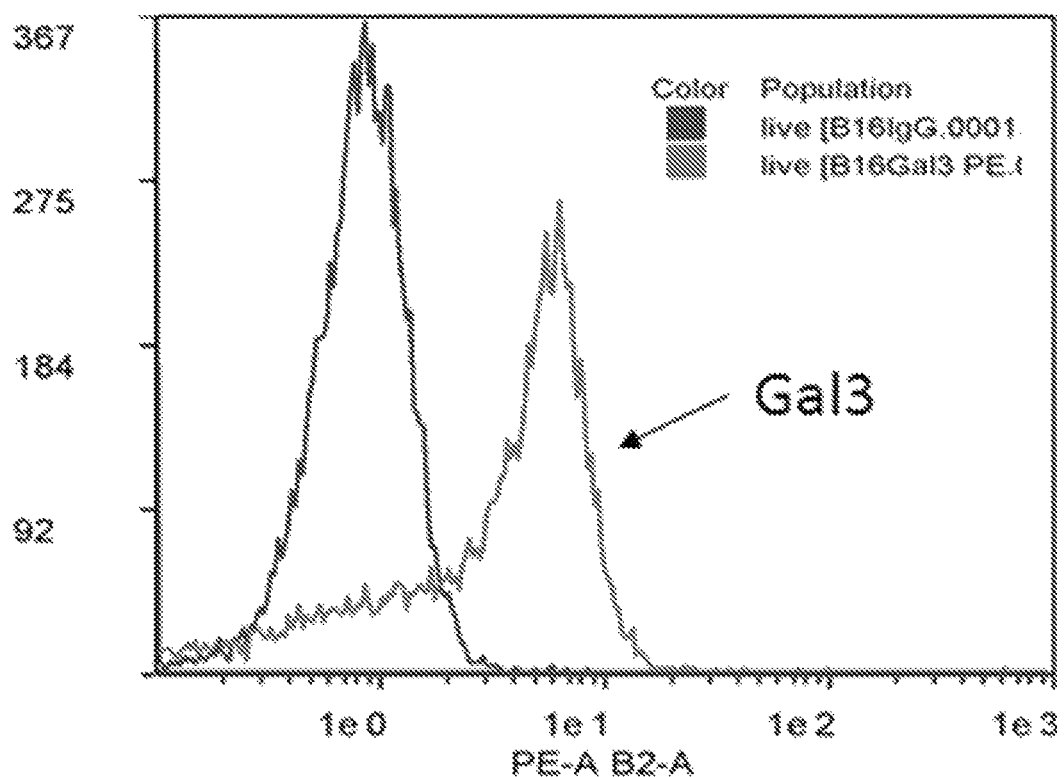
FIGS. 7A-7E show that Gal3 antibody has anti-tumor activity in a lung metastasis model.
Figure 7B:
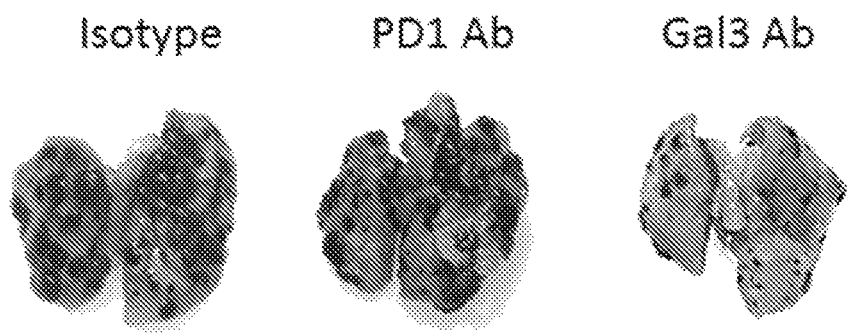
Figure 7C:
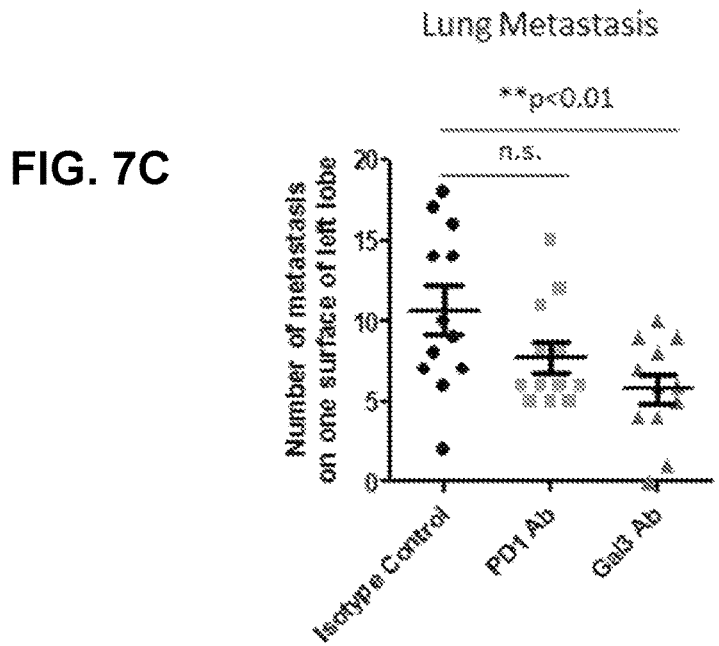
Figure 7D:
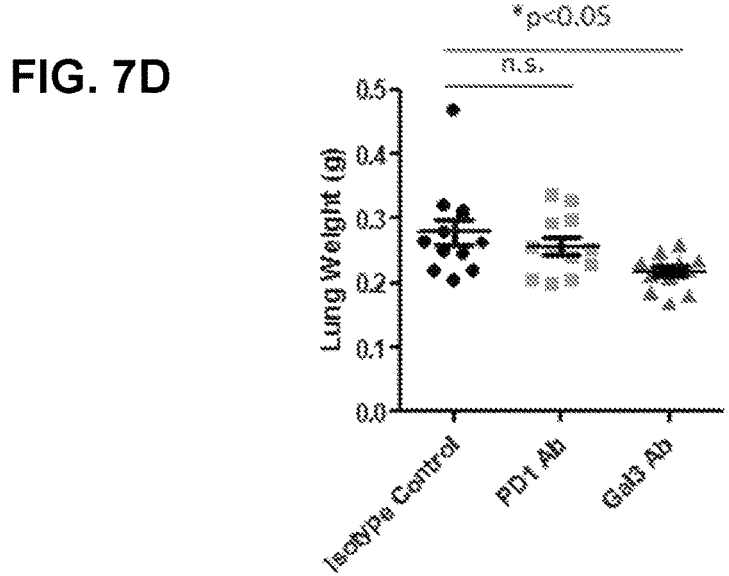
Figure 7E:
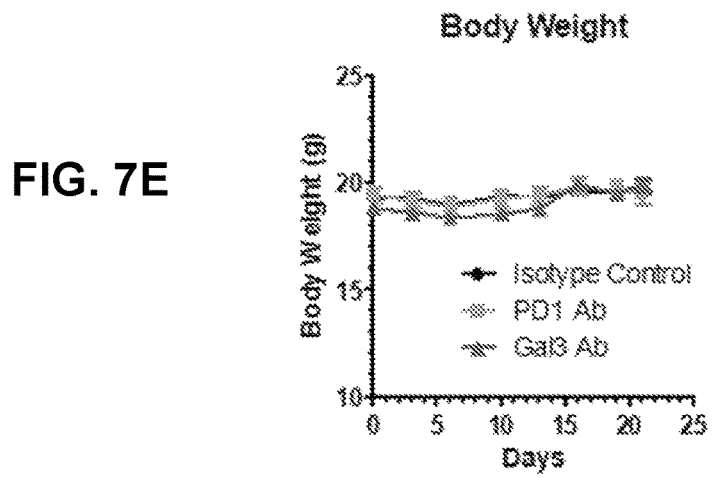

FIG. 7A shows that the mean fluorescence intensity (MFI) of B16F10 cells stained with anti mGAL3 antibody is nearly ten-fold higher than that of cells stained with isotype control antibody. In details, B16F10 cells were incubated with 10% FBS HBSS solution that contains control rat IgG PE or rat anti mouse Gal3 PE antibody (Thermo Fisher Scientific, Waltham, Mass.) on ice for 20 minutes. After spinning, live/dead cells were stained with Violet dead cell stain kit (Thermo Fisher Scientific, Waltham, Mass.). Stained cells were subjected to flow analysis. FIG. 7B shows representative images of the whole lung from three treated groups. FIG. 7C shows numbers of metastatic colonies on surface of the left lung lobe (Mean±SEM). FIG. 7D and FIG. 7E shows lung weight and body weight of different treatment groups (Mean±SEM). As compared to isotype control group, the Gal3 antibody treated group showed significant (about 46%) reduction of tumor number ($p<0.01$) as indicated by the number of black metastatic colonies. However, in comparison with isotype control group, anti mouse PD1 antibody 29F did not show significant anti-tumor effect in this lung metastasis model ($p>0.05$).

Example 5. An Anti-Gal3 Antibody Shows Anti-Tumor Activity in 4T1 Orthotopic Tumor Induced Lung Metastasis Model The animal experiment followed a protocol approved by the Molecular Medicine Research Institute Institutional Animal Care and Use Committee. 7-week old female Balb/c mice were placed in a facility accredited by the Association for Assessment and Accreditation of Laboratory Animal Care upon arrival. On the day of tumor implantation, 4T1 cells were collected, washed and resuspended in PBS. Mice were anesthetized by inhalation anesthetic (3 to 5% Isoflurane in medical grade air). $2\times10^5$ cells in 0.1 mL PBS were subcutaneously injected into the mammary gland by using a syringe with a 25-ga needle. Mice were randomly assigned into two groups (n=10). Following injection of the 4T1 cells, the mice were administrated intraperitoneally with 10 mg/Kg of mouse IgG2b (Bio X Cell) on day 0, 3 and 7 or Gal3 antibody IMT001 on day 0, 3, 7, 10 and 14. The tumor volumes and body weights were monitored twice per week. On day 30, the mice were humanely sacrificed and lung tissues were inflated with 30% sucrose, removed and fixed in Bouin's solution (Sigma-Aldrich). The number of metastatic colonies on one surface of the left lobes in the lungs were counted. Results were expressed as mean±SEM. The statistical analysis was performed in comparison with IgG control group using unpaired T test.

Figure 8A:
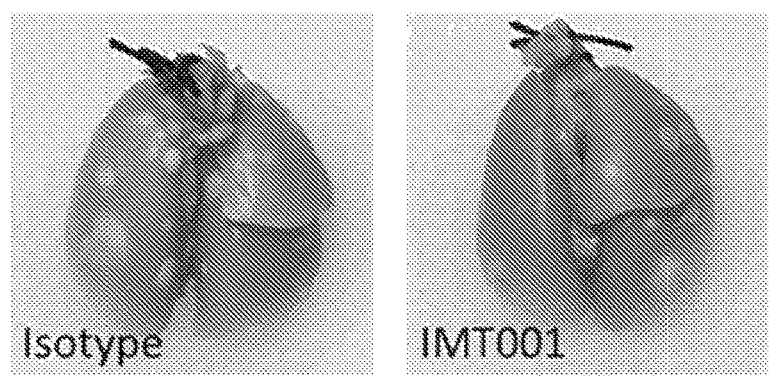
FIGS. 8A-8C show the anti-tumor activity of Gal3 antibody in 4T1 orthotopic tumor induced lung metastasis.
Figure 8B:
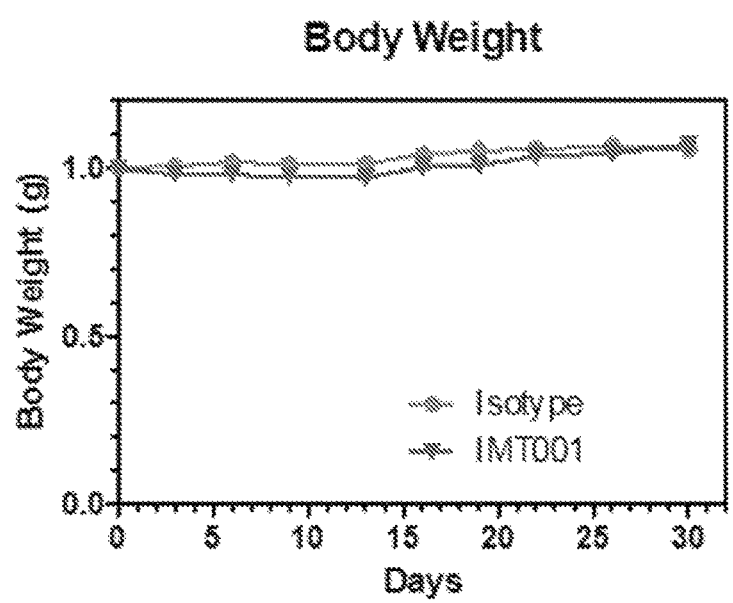
Figure 8C:
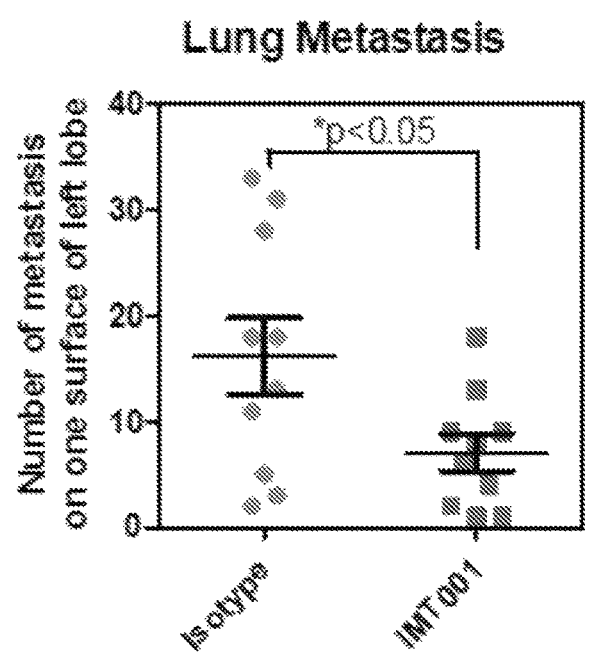

FIG. 8A shows representative images of the whole lung from the treated groups. FIG. 8B shows body weight of different treatment groups (Mean±SEM). FIG. 8C shows numbers of metastatic colonies on one surface of the left lung lobe (Mean±SEM). As compared to mice treated with the isotype control antibody, animals treated with the monoclonal anti-human Gal3 antibody showed significant reduction of lung metastatic number (p<0.05).

Figure 9:
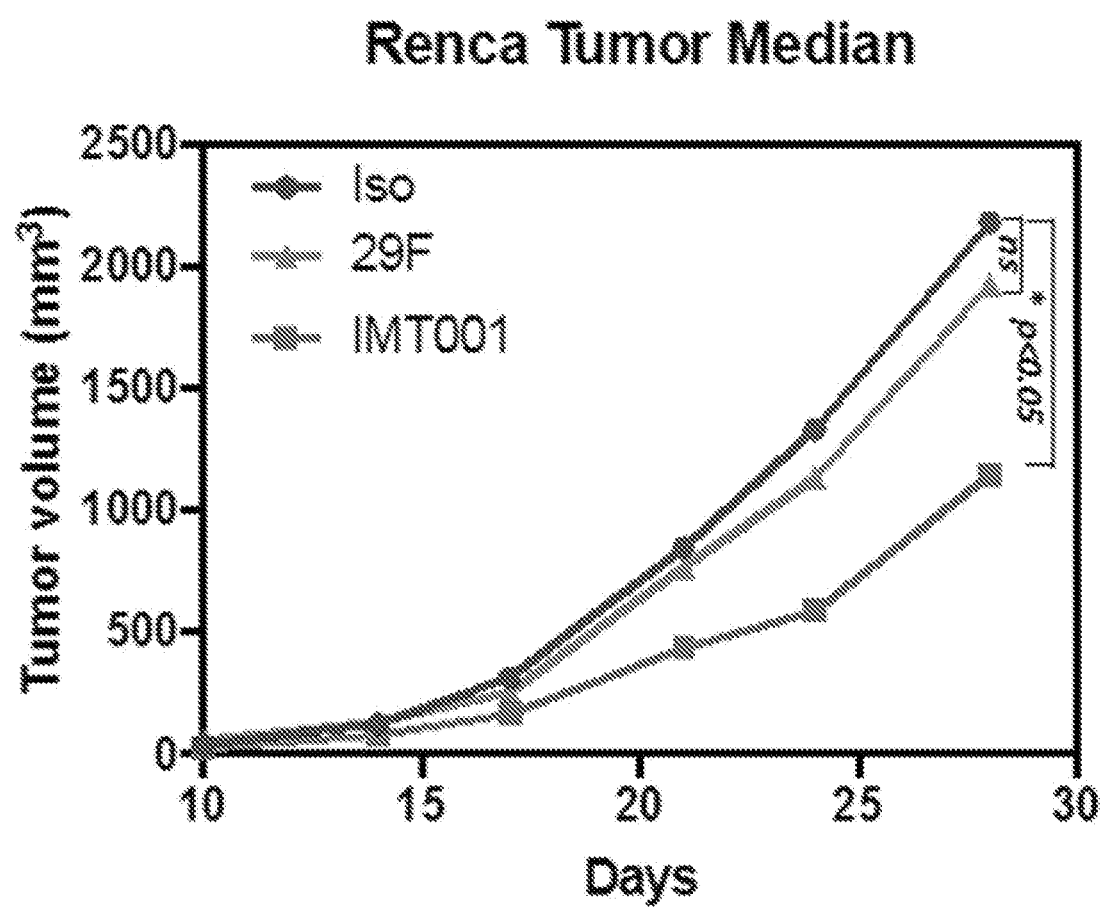
FIG. 9 shows the tumor growth in mice implanted with Renca tumor cells and treated with Gal3 antibody. As compared to mice implanted with Renca tumor cells and treated with the isotype control antibody ("iso"), mice treated with Gal3 antibody ("IMT001") showed much reduced tumor size (p<0.05), while anti mouse PD-1 antibody 29F had no effects (p>0.05).

Example 6. An Anti-Gal3 Antibody Shows Anti-Tumor Activity in Primary Mouse Renca Renal Tumor Model The experiments were conducted to evaluate the anti-tumor efficacy of Gal3:TIM-3 inhibitor in primary tumor model (FIG. 9). The animal experiments were conducted according to a protocol approved by the Molecular Medicine Research Institute Institutional Animal Care and Use Committee. Balb/c mice were placed in a facility accredited by the Association for Assessment and Accreditation of Laboratory Animal Care upon arrival. Seven-week old female mice were randomly assigned into three groups (n=15). On the day of tumor implantation, mice were anesthetized by inhalation anesthetic (3 to 5% Isoflurane in medical grade air), Renca cells were washed and resuspended in PBS before subcutaneously injecting $2\times10^5$ cells in 0.1 mL PBS using a syringe with a 25-ga needle. Following injection of the Renca cells, mice were i.p. administrated with either 10 mg/Kg of mouse IgG2b (Bio X Cell) or mPD1 antibody (BioXCell) on day 0, 3 and 7 or Gal3 antibody IMT001 antibody on day 0, 3, 7, 10 and 14. The animals were humanely sacrificed when tumor volume in the control group reached between 2000-2500 mm³. Results were expressed as mean±SEM, The statistical analysis was performed in comparison with IgG2b control group using unpaired t test.

The results show the anti-tumor activity of Gal3 antibody (IMT001) in a renal carcinoma model. As compared to isotype control group, the anti-Gal3 antibody treated group showed significant (about 35%) reduction of tumor growth (p<0.05), while anti-PD-1 antibody had no effect (FIG. 9).

Example 7. An Anti-Gal3 Antibody Shows Anti-Tumor Activity in Primary Mouse Mc38 Colon Tumor Model The animal experiment followed a protocol approved by the Molecular Medicine Research Institute Institutional Animal Care and Use Committee. 7-week old female C57BL/6 mice were placed in a facility accredited by the Association for Assessment and Accreditation of Laboratory Animal Care upon arrival. On the day of tumor implantation, MC38 murine colon adenocarcinoma cells were collected, washed and resuspended in PBS. Mice were anesthetized by inhalation anesthetic (3 to 5% Isoflurane in medical grade air). $5\times10^5$ cells in 0.1 mL PBS were subcutaneously injected into the right flank of mice by using a syringe with a 25-ga needle. On day 7, the tumor volumes were measured and mice were randomly assigned into two groups (n=8). The mice were administrated intraperitoneally with 10 mg/Kg of mouse IgG2b (BioXCell) or Gal3 antibody IMT001 on day 7, 10, 14, 17 and 22. The tumor volumes and body weights were monitored twice per week. The animals were humanely sacrificed when tumor volume reached 3000 mm³. Results were expressed as mean±SEM. The statistical analysis was performed in comparison with IgG control group using unpaired T test.

Figure 10:
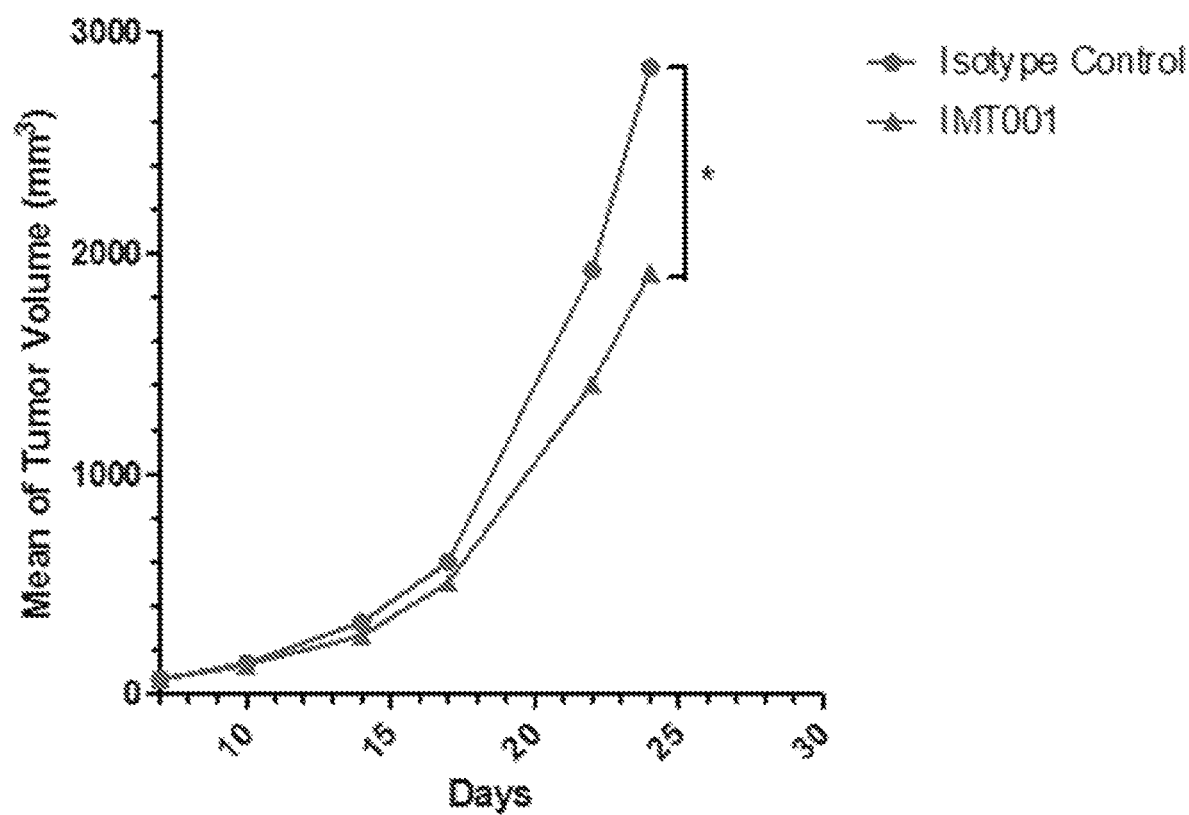
FIG. 10 shows the tumor growth in mice implanted with MC38 colon cancer cells and treated with the anti Gal3 antibody. As compared to mice implanted with MC38 tumor cells and treated with the isotype control antibody ("iso"), mice treated with Gal3 antibody ("IMT001") showed much reduced tumor size (p<0.05).

The results in FIG. 10 shows that IMT001 antibody has anti-tumor activity in the MC38 colon cancer model. As compared to mice that were treated with the isotype control antibody, IMT001 antibody treated mice showed significant reduction (about 33%) of tumor burden on day 24 (p<0.05).

Example 8. Epitope Binding Of Gal3 Antibody Clone IMT-001

A peptide array containing 24 20 amino acid peptides overlapping by 10 amino acid and covering the whole human Gal3 protein sequence was synthesized (Genscript, Piscataway, N.J.) (FIG. 11A). 20 µg of each peptide was dot blotted onto a membrane. After blocking with 5% milk in PBS, the membrane was incubated with 1 µg/ml IMT001 antibody at 4C for overnight. After three times of washes, the membrane was incubated with 1:8000 diluted anti mIgG HRP antibody (Southern Biotech, Birmingham, Ala.) for one hour. After three times of washes, the membrane was incubated with Western ECL blotting substrates (Bio-Rad, Hercules, Calif.) and developed (FIG. 11B). Peptides 5 and 6 showed good signal, indicating the epitope on hGal3 to which IMT001 binds is PGAYPGQAPPGAYPGQAPPGAYPGAPGAYP (SEQ ID NO: 7).

To further define binding epitope of IMT001 on the above peptide, 8 shorter peptides derived from it were synthesized (Genscript, Piscataway, N.J.) (FIG. 11C) and their binding by IMT001 was determined by ELISA (FIG. 11D). 96 well Elisa plate (Thermo Scientific) was coated with these peptides in PBS buffer and incubated at 4° C. for overnight. The plate was washed three times with TBST and then blocked with PBST buffer containing 2% BSA at room temperature for 1 h. IMT001 at 10 µg/mL was incubated in the coated Elisa plate at room temperature for 1 h. The plate was washed for three times and followed by incubation with 1:8000 dilution of anti-mouse-IgG-HRP for 1 h at room temperature. The color was developed with 100 µL of TMB subtract (GeneTex) after three time washes with TBST and stopped by 50 µL of 1 N HCl. The optical density (OD) was read at 450 nm. The results were expressed as the average OD of duplicates±SD. Pep-2 showed good signal, indicating the binding epitope of IMT001 on human Gal3 is GQAPP-GAYPG (SEQ ID NO: 8).

Example 9. Immune Profiling In B16F10 Lung Metastasis Mice Tumor

Figure 12:
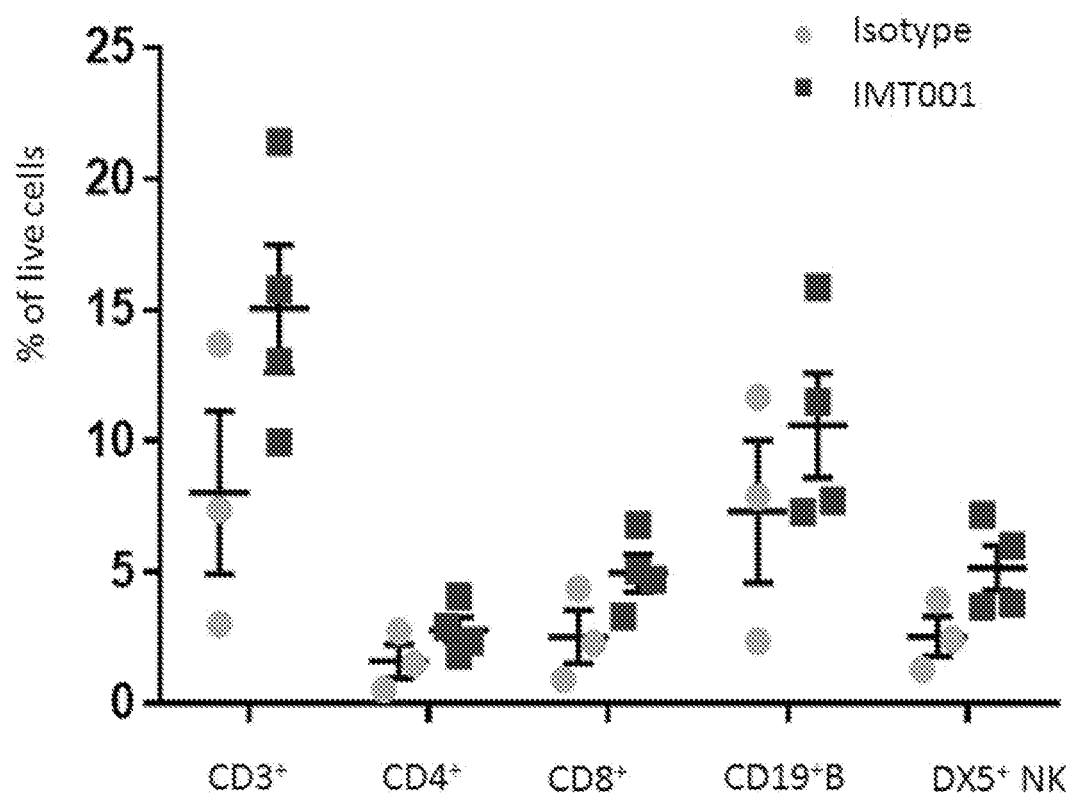
FIG. 12 summarizes the number of immune cells from mice implanted with B16F10 cells that express various lymphocyte markers: CD3, CD4, CD8, CD19, or DX5. These mice have been treated with the isotype control antibody or IMT001.

Mice were implanted with 1 million B16F10 cells I.V. Mice were then treated with IMT001 or isotype control (10 mg/kg I.P.) on Day 0, 1, 3 and 7 and sacrificed on day 8 for lung immune cell isolation and phenotyping. Cells were isolated from the lungs, and then stained with fluorescently labeled antibodies against lymphocyte markers CD3, CD4, CD8, CD19, DX5 and analyzed by flow cytometry. The results in FIG. 12 show that the anti-Gal3 antibody IMT001 treatment, as compared to isotype control antibody treatment, increased the number of various immune effector cell, including CD3 T lymphocytes, CD4 T helpers, CD8 cytotoxic T cells, CD19 B cells and DX5 Natural Killer cells in lungs that host the tumors. This indicates that the anti-Gal3 antibody was able to activate immune cells.

Example 10. Gal3 Expression Detected on Human Lung Cancer Associated Macrophages Immunohistochemistry (IHC) experiment was conducted to detect Gal3 expression in human lung cancers. The frozen tissue slides of human lung cancers (US Biomax Inc.) were fixed in 10% neutral buffered formalin (Fisher Scientific) at room temperature for 10 min and washed twice for 5 min in PBS. Endogenous peroxidase was blocked by immersing slides in 3% $H_2O_2$ at room temperature for 10 min. After washing twice in PBS for 5 min, the slides were incubated in streptavidin reagent (Molecular Probes) for 15 min at room temperature, followed by rinse thoroughly with PBS, incubation in biotin reagent (Molecular Probes) for 15 min and another rinse in PBS to block the endogenous biotin background. The slides were blocked with 10% FBS, 200 µg/mL mIgG and 200 µg/mL hIgG for 1 h, incubated with 1st antibody IMT001-biotin (5 µg/mL) at 4° C. for overnight, washed three times, then followed by incubation with $2^{nd}$ antibody HRP avidin (BioLegend) at 1:100 for 1 h and washes for three time. The staining was developed by incubating with DAB substrate (Vector Laboratories) and stopped by immersing slides in distilled water. Human lung cancer slides were finally counterstained in Hematoxylin QS (Vector Laboratories), washed in distilled water, dehydrated in a graded series of ethanol and xylenes solutions, and mounted in VectaMount™ Mounting Medium (Vector Laboratories).

Figures 13A, 13B:
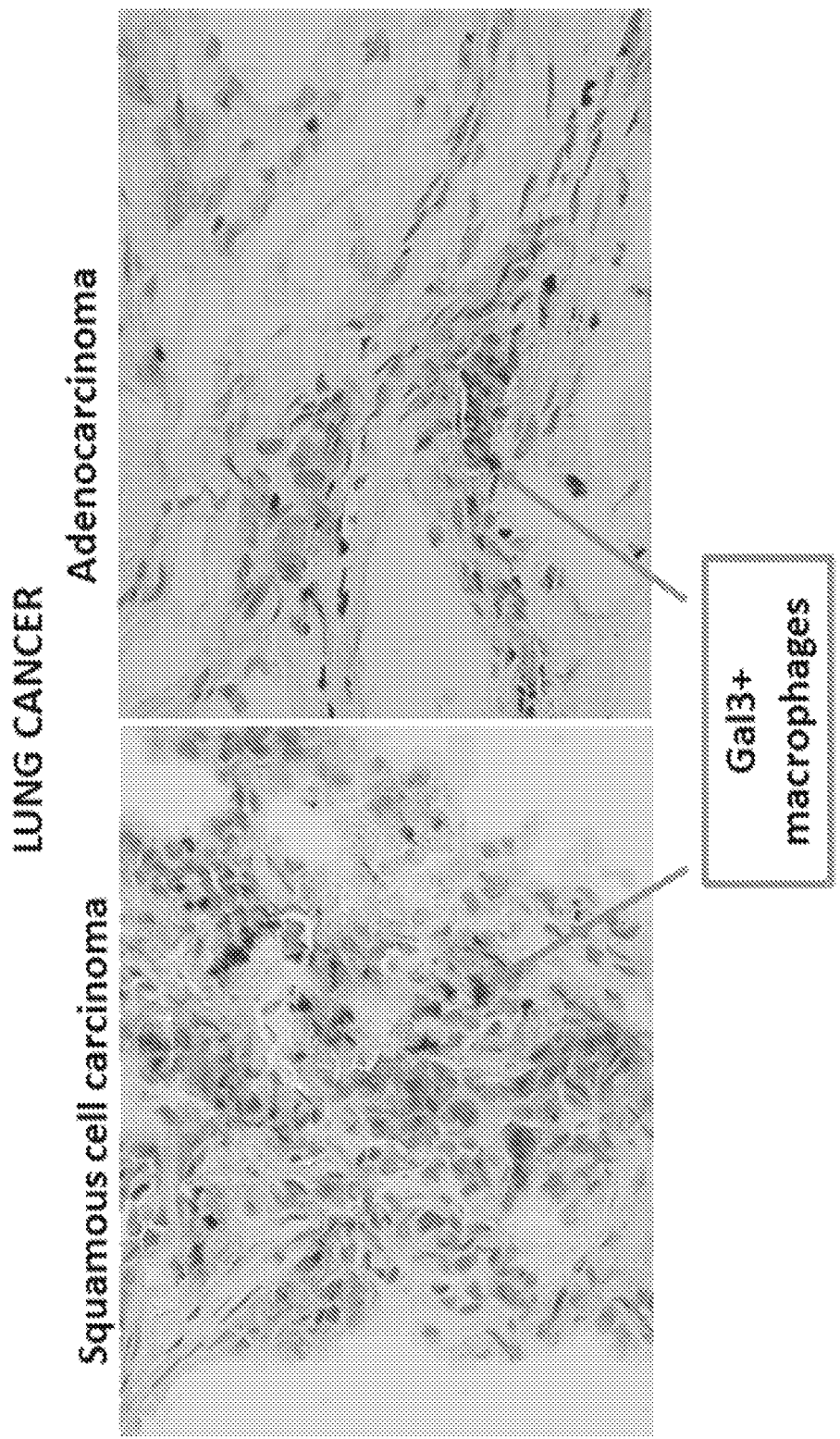
FIGS. 13A and 13B show Gal3 expression on tumor associated macrophages in human lung cancer in immunohistochemistry (IHC) assays. IMT001 was used to stain human lung cancer frozen slides to detect Gal3 expression on tumor associated macrophages.

Results in FIG. 13 shows that the canopy shaped tumor associated macrophages in those human lung cancer slides (squamous cell carcinoma and adenocarcinoma) express Gal3, as evidenced by their positive staining by IMT001.

Example 11. Gal3 Expression on Human M2 Macrophages

Figure 14A:
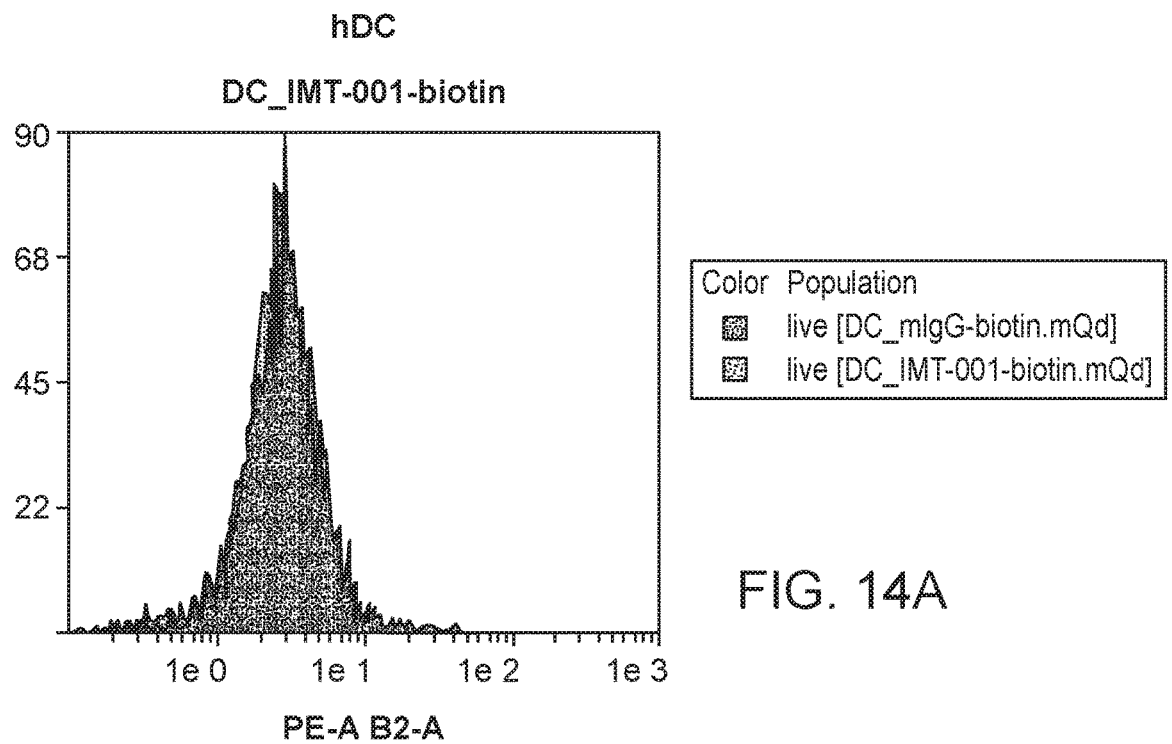
FIGS. 14A-14C show that expression of Gal3 was detected on human M2 macrophages (FIG. 14C), but not on Dendritic cells (DC) (FIG. 14A) or M1 macrophages (FIG. 14B).
Figure 14B:
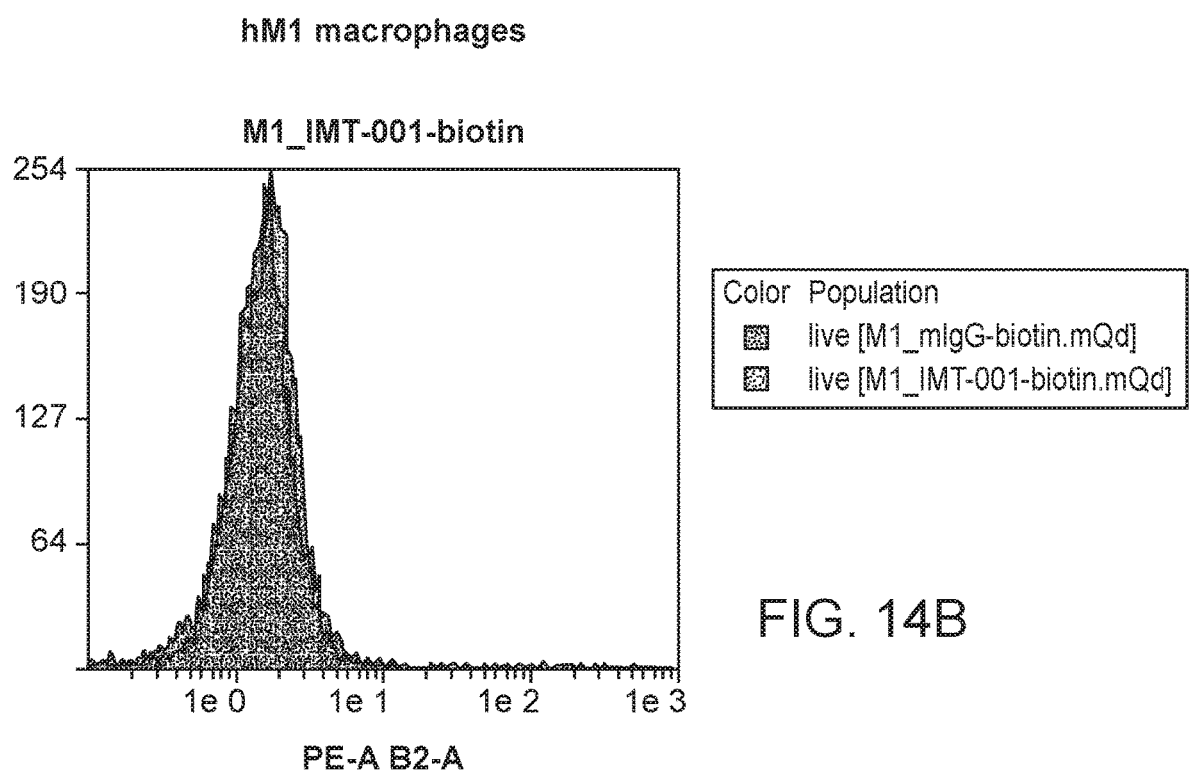
Figure 14C:
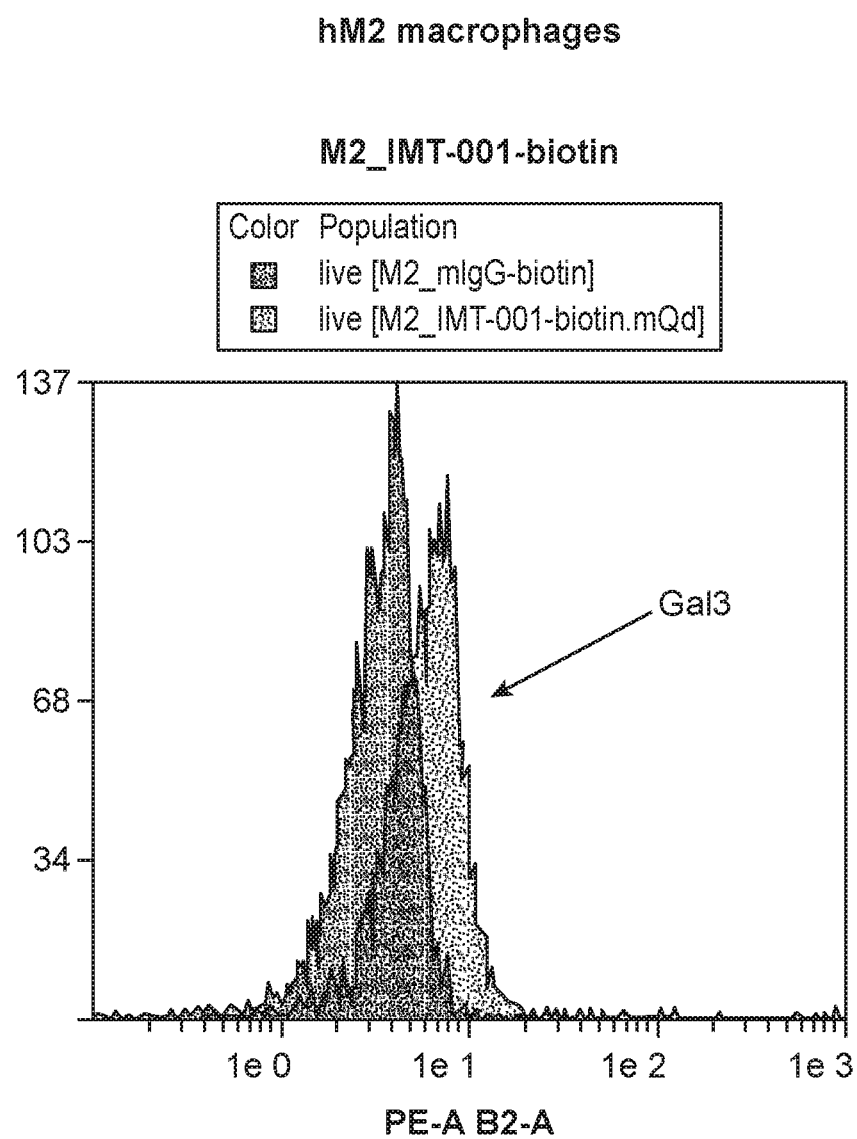

First Human CD14 monocytes were isolated from peripheral blood mononuclear cells (PBMC) with a CD14 cell positive selection kit (Miltenyi, Auburn, Calif.) and differentiated into dendritic cells (DC), or into M1 macrophages, or into M2 macrophages in the presence of GM-CSF plus IL-4, or GM-CSF, or M-CSF (Rocky Hill, N.J.), respectively. Then flow cytometry analysis was performed to detect Gal3 expression on human dendritic cells (DC), M1 and M2 macrophage cells. In details, 100,000 DC, M1 or M2 cells were incubated with 100 µl 10% FBS HBSS solution that contains with control mIgG-biotin (BioLegend) or IMT001-biotin at 10 µg/ml on ice for 20 minutes. Then cells were washed and incubated with PE-streptavidin (BioLegend) at 1:1000 on ice for 20 min. After spinning, live/dead cells were stained with Violet dead cell stain kit (Life Technologies). Stained cells were subjected to flow analysis. Results in FIG. 14C. shows that the mean fluorescence intensity (MFI) of M2 cells stained with IMT001 is much higher than that of cells stained with isotype control antibody, indicating the specific binding of IMT001 with M2 cells, while dendritic cells (FIG. 14A) and M1 macrophages (FIG. 14B) could not be stained.

Figure 15A:
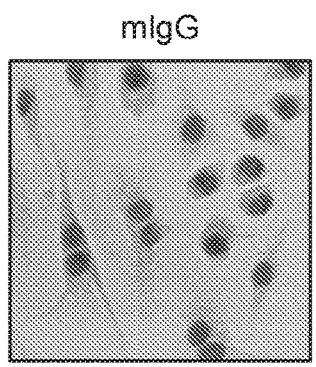
FIG. 15 shows the immune activity of Gal3 antibody ("IMT001") in mouse macrophage/T cell reaction.
FIG. 15B shows detection of expression of Gal3 by IHC on mouse macrophage cell line RAW264.7, as compared to control (FIG. 15A).
FIG. 15C shows the expression of Gal 3 on mouse macrophage cell line by flow cytometry using cells stained with IMT001. The anti Gal3 antibody IMT001, but not anti mouse PD-1 antibody 29F, enhanced IL-2 production in RAW macrophages/DO11.10 T cell mixed reaction (FIG. 15D).
Figure 15B:
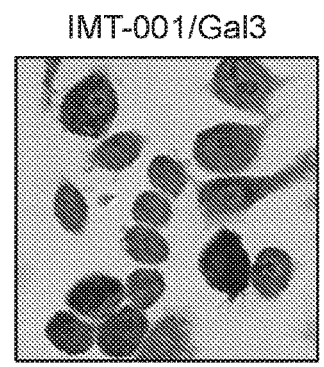

Example 12. Anti Gal3 Antibody Enhances Mouse T Cell Activity in Macrophage/T Cell Reaction The expression of Gal3 on mouse macrophages was detected by both IHC and Flow cytometry analysis. In the details of IHC, 100,000 cells per well were seeded overnight. On the second day, cells were washed once with PBS, fixed with 3% formaldehyde at room temperature for 10 min, then washed twice with PBS and blocked in PBS containing 10% FBS and 200 µg/mL for 1 h at room temperature. After blocking, cells were incubated with 10 µg/mL of $1^{st}$ antibody mIgG-biotin (BioLegend) or IMT001-biotin at 4° C. overnight, washed three times with PBST, stained with avidin-HRP (1:1000) at room temperature for 1 h and then washed three times again with PBST. The staining was developed using peroxidase substrate and counterstained with Hematoxylin QS (Vector Laboratories). Results shows that, as compared to mIgG control (FIG. 15A), IMT001 clearly detected Gal3 expression on macrophages (FIG. 15B).

Figure 15C:
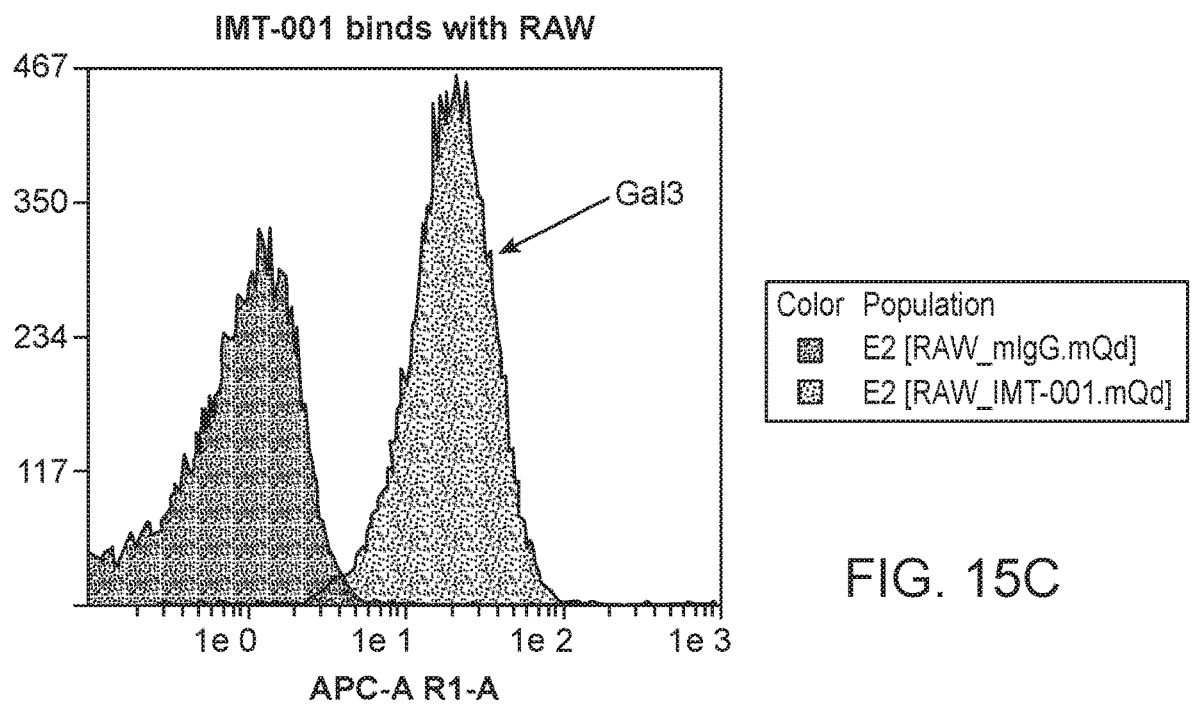

In the experiment of flow cytometry, 100,000 RAW cells were blocked with 10% FBS plus 200 µg/mL hIgG on ice for 20 min, and then incubated with 100 µl 10% FBS HBSS solution that contains control mIgG (BD Biosciences) or IMT001 at 10 µg/ml on ice for 20 minutes. Then cells were washed and incubated with APC conjugated anti-mFc antibodies (Jackson ImmunoResearch) at 1:100 on ice for 20 min. After spinning, live/dead cells were stained with Violet dead cell stain kit (Life Technologies). Stained cells were subjected to flow analysis. FIG. 15C shows that, as compared to that of cells stained with isotype control antibody, the mean fluorescence intensity (MFI) of RAW cells stained with IMT001 is more than 10-folds higher.

The ability of IMT001 to activate T cell was demonstrated by Mixed Lymphocyte Reaction (MLR) assay. RAW mouse macrophage cells were mixed with DO11 mouse T cells at 1:1 ratio, treated with OVA peptide, and cultured in the presence of mIgG (BD Biosciences), anti mPD1 antibody 29F (BioXCell) or IMT001 at 10 µg/ml for overnight 37° C. 50 µl of the culture medium was taken for mIL-2 measurement. The mIL-2 production was measured according to the commercial kit mouse IL-2 Elisa Ready-SET-Go from eBioscience.

Figure 15D:
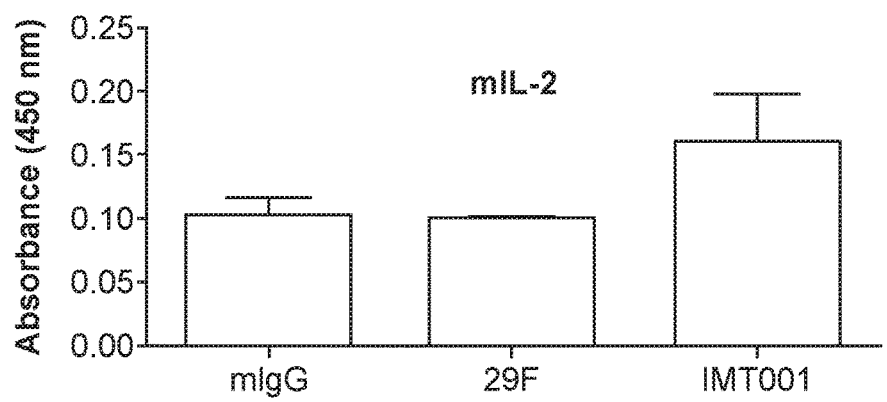

FIG. 15D shows that in comparison of mIgG or mPD1 antibody treated cells, IMT001 antibody, but not mouse PD-1 antibody 29F, enhanced the production of IL-2, indicating the reversion of macrophage induced T-cell inactivation.

Although the forgoing invention has been described in some detail by way of illustration and example for clarity and understanding, it will be readily apparent to one of ordinary skill in the art in light of the teachings of this invention that certain variations, changes, modifications and substitutions of equivalents may be made thereto without necessarily departing from the spirit and scope of this invention. As a result, the embodiments described herein are subject to various modifications, changes and the like, with the scope of this invention being determined solely by reference to the embodiments appended hereto. Those of skill in the art will readily recognize a variety of non-critical parameters that could be changed, altered or modified to yield essentially similar results. It is also to be understood that the terminology used herein is for the purpose of describing particular embodiments only, and is not intended to be limiting, since the scope of the present invention will be limited only by the appended embodiments. In addition, each reference provided herein is incorporated by reference in its entirety to the same extent as if each reference was individually incorporated by reference. Where a conflict exists between the instant application and a reference provided herein, the instant application shall dominate.

INFORMAL SEQUENCE LISTINGS

SEQ ID NO: 1 the *Mus musculus* Gal3 nucleic acid (cDNA) sequence (the start and stop codons are underlined.)
GGGAGGGCGG GCCCGGGGAA AAGAGTACTA GAAGCGGCCG AGCCACCGCC CAGCTCTGAC
AGCTAGCGGA GCGGCGGGTG GAGCACTAAT CAGGTGAGCG GCACAGAGAG CACTACCCAG
GAAAATGGCA GACAGCTTTT CGCTTAACGA TGCCTTAGCT GGCTCTGGAA ACCCAAACCC
TCAAGGATAT CCGGGTGCAT GGGGGAACCA GCCTGGGGCA GGGGGCTACC CAGGGGCTGC
TTATCCTGGG GCCTACCCAG GACAAGCTCC TCCAGGGGCC TACCCAGGAC AGGCTCCTCC
AGGGGCCTAC CCAGGACAGG CTCCTCCTAG TGCCTACCCC GGCCCAACTG CCCCTGGAGC
TTATCCTGGC CCAACTGCCC CTGGAGCTTA TCCTGGCTCA ACTGCCCCTG GAGCCTTCCC
AGGGCAACCT GGGGCACCTG GGGCCTACCC CAGTGCTCCT GGAGGCTATC CTGCTGCTGG
CCCTTATGGT GTCCCCGCTG GACCACTGAC GGTGCCCTAT GACCTGCCCT TGCCTGGAGG
AGTCATGCCC CGCATGCTGA TCACAATCAT GGGCACAGTG AAACCCAACG CAAACAGGAT
TGTTCTAGAT TTCAGGAGAG GGAATGATGT TGCCTTCCAC TTTAACCCCC GCTTCAATGA
GAACAACAGG AGAGTCATTG TGTGTAACAC GAAGCAGGAC AATAACTGGG GAAAGGAAGA
AAGACAGTCA GCCTTCCCCT TGAGAGTGG CAAACCATTC AAAATACAAG TCCTGGTTGA
AGCTGACCAC TTCAAGGTTG CGGTCAACGA TGCTCACCTA CTGCAGTACA ACCATCGGAT
GAAGAACCTC CGGGAAATCA GCCAACTGGG GATCAGTGGT GACATAACCC TCACCAGCGC
TAACCACGCC ATGATCTAAG CCAGAAGGGG CGGCACCGAA ACCGGCCCTG TGTGCCTTAG
GAGTGGGAAA CTTTGCATTT CTCTCTCCTT ATCCTTCTTG TAAGACATCC ATTTAATAAA
GTCTCATGCT GAGAGATACC CATCGCTTTG GGGGTTTTTA TGATACTGGA TGTCAAATCT
TAGGACTGCT CGTGACTGCT AGGCAAGTGT TCTCTCACTG AGCTACACAT CCCTAGCCTT
TTAAACTTTG TGTGTTGTGT GTCTGTGCAC ATGGGTACAG GTGCCTGCTC ACTTGAGAGG
CACCAGGCCT CCTGGAGCTG GAGTTACAGG TGGTTGTAAG TAAGCTGTGT GACCAGGTTG
CTGGGAACCA GTCTCAGATC CTCCTGAGAC AGGTCAGGTC CACTGATGCC TCCAGCTGCC
TGTCTTTATA TGCCCTTTGA TTTGGTGCAG TTTTATATAA AGGGAACTAT GTAATTATCA
ATAAACCATC CTGATTTTTA CAAAGG SEQ ID NO: 2: the *Mus musculus* Gal3 polypeptide sequence
MADSFSLNDALAGSGNPNPQGYPGAWGNQPGAGGYPGAAYPGAY
PGQAPPGAYPGQAPPGAYPGQAPPSAYPGPTAPGAYPGPTAPGAYPGSTAPGAFPGQP
GAPGAYPSAPGGYPAAGPYGVPAGPLTVPYDLPLPGGVMPRMLITIMGTVKPNANRIV
LDFRRGNDVAFHFNPRFNENNRRVIVCNTKQDNNWGKEERQSAFPFESGKPFKIQVLV
EADHFKVAVNDAHLLQYNHRMKNLREISQLGISGDITLTSANHAMI SEQ ID NO: 3: the *Homo sapiens* Gal3 nucleic acid (cDNA) sequence (the start and stop codons are underlined.)
GAGTATTTGA GGCTCGGAGC CACCGCCCCG CCGGCGCCCG CAGCACCTCC TCGCCAGCAG
CCGTCCGGAG CCAGCCAACG AGCGGAAAAT GGCAGACAAT TTTTCGCTCC ATGATGCGTT
ATCTGGGTCT GGAAACCCAA ACCCTCAAGG ATGGCCTGGC GCATGGGGGA ACCAGCCTGC
TGGGGCAGGG GGCTACCCAG GGGCTTCCTA TCCTGGGGC TACCCGGGC AGGCACCCCC
AGGGGCTTAT CCTGGACAGG CACCTCCAGG CGCCTACCCT GGAGCACCTG GAGCTTATCC
CGGAGCACCT GCACCTGGAG TCTACCCAGG GCCACCCAGC GGCCCTGGGG CCTACCCATC
TTCTGGACAG CCAAGTGCCA CCGGAGCCTA CCCTGCCACT GGCCCCTATG GCGCCCCTGC
TGGGCCACTG ATTGTGCCTT ATAACCTGCC TTTGCCTGGG GGAGTGGTGC CTCGCATGCT
GATAACAATT CTGGGCACGG TGAAGCCCAA TGCAAACAGA ATTGCTTTAG ATTTCCAAAG
AGGGAATGAT GTTGCCTTCC ACTTTAACCC ACGCTTCAAT GAGAACAACA GGAGAGTCAT
TGTTTGCAAT ACAAAGCTGG ATAATAACTG GGGAAGGGAA GAAAGACAGT CGGTTTTCCC
ATTTGAAAGT GGGAAACCAT TCAAAATACA AGTACTGGTT GAACCTGACC ACTTCAAGGT
TGCAGTGAAT GATGCTCACT TGTTGCAGTA CAATCATCGG GTTAAAAAAC TCAATGAAAT
CAGCAAACTG GGAATTTCTG GTGACATAGA CCTCACCAGT GCTTCATATA TCATGATATA
ATCTGAAAGG GGCAGATTAA AAAAAAAAAA AGAATCTAAA CCTTACATGT GTAAAGGTTT
CATGTTCACT GTGAGTGAAA ATTTTACAT TCATCAATAT CCCTCTTGTA AGTCATCTAC
TTAATAAATA TTACAGTGAA TTACCTGTCT CAATATGTCA AAAAAAAAA AAAAAA SEQ ID NO: 4: the *Homo sapiens* Gal3 polypeptide sequence
MADNFSLHDALSGSGNPNPQGWPGAWGNQPAGAGGYPGASYPGA
YPGQAPPGAYPGQAPPGAYPGAPGAYPGAPAPGVYPGPPSGPGAYPSSGQPSATGAYP
ATGPYGAPAGPLIVPYNLPLPGGVVPRMLITILGTVKPNANRIALDFQRGNDVAFHFN
PRFNENNRRVIVCNTKLDNNWGREERQSVFPFESGKPFKIQVLVEPDHFKVAVNDAHL
LQYNHRVKKLNEISKLGISGDIDLTSASYTMI SEQ ID NO: 5: hGal3 epitope, corresponding to peptide_5 in FIG. 11A
PGAYPGQAPPGAYPGQAPPG SEQ ID NO: 6: hGal3 epitope, corresponding to peptide_6 in FIG. 11A
GAYPGQAPPGAYPGAPGAYP

| INFORMAL SEQUENCE LISTINGS |
| --- |

SEQ ID NO: 7: hGal3 epitope
PGAYPGQAPPGAYPGQAPPGAYPGAPGAYP

Figures 11C, 11D:
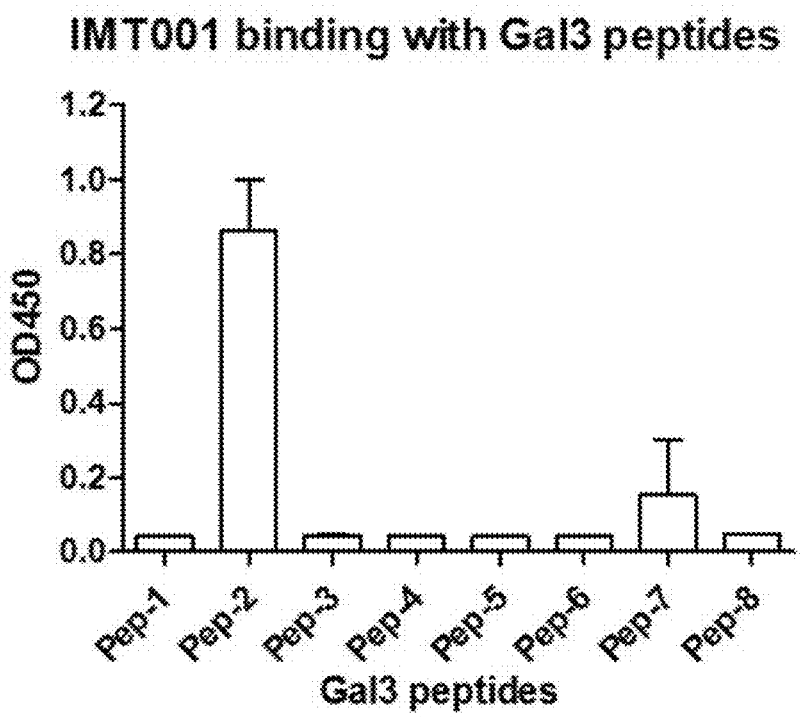

SEQ ID NO: 8: hGal3 epitope, corresponding to Pep-2 in FIG. 11C
GQAPPGAYPG

| Humanized IMT001 in hIgG4 isotype |
| --- |

SEQ ID NO: 9: Heavy chain CDR1
GYTFTNY

SEQ ID NO: 10 Heavy chain CDR2
NTNTGE

SEQ ID NO: 11 Heavy chain CDR3
YDNFFAY

SEQ ID NO: 12 Heavy chain FR1
QVQLVQSGSELKKPGASVKVSCKAS

SEQ ID NO: 13 Heavy chain FR2
GMNWVRQAPGQGLKWMGWI

SEQ ID NO: 14 Heavy chain FR3
PTYAQEFTGRFVFSLDTSVSTAYLQISSLKAEDTAVYFCAP

SEQ ID NO: 15 Heavy chain FR4
WGQGTTVTVS

SEQ ID NO: 16 heavy chain
QVQLVQSGSELKKPGASVKVSCKASGYTFTNYGMNWVRQAPGQGLKWMGWINTNTGEPTYAQEFTG
RFVFSLDTSVSTAYLQISSLKAEDTAVYFCAPYDNFFAYWGQGTTVTVSSASTKGPSVFPLAPCSRSTSESTA
ALGCLVKDYFPEPVTVSWNSGALTSGVHTFPAVLQSSGLYSLSSVVTVPSSSLGTKTYTCNVDHKPSNTKVD
KRVESKYGPPCPPCPAPEFLGGPSVFLFPPKPKDTLMISRTPEVTCVVVDVSQEDPEVQFNWYVDGVEVH
NAKTKPREEQFNSTYRVVSVLTVLHQDWLNGKEYKCKVSNKGLPSSIEKTISKAKGQPREPQVYTLPPSQE
EMTKNQVSLTCLVKGFYPSDIAVEWESNGQPENNYKTTPPVLDSDGSFFLYSRLTVDKSRWQEGNVFSCS
VMHEALHNHYTQKSLSLSLG**

SEQ ID NO: 17 light chain CDR1
RSSKSLLYKDGKTYLN

SEQ ID NO: 18 light chain CDR2
LMSTHAS

SEQ ID NO: 19 light chain CDR3
QQLVDYPLT

SEQ ID NO: 20 light chain FR1
DIVLTQSPLSLPVTPGEPASISC

SEQ ID NO: 21 light chain FR2
WFLQKPGQSPQLLIY

SEQ ID NO: 22 Light chain FR3
GVPDRFSGSGSGTDFTLKISRVEAEDVGVYYC

SEQ ID NO: 23 light chain FR4
FGGGTKLEIK

SEQ ID NO: 24 light chain
DIVLTQSPLSLPVTPGEPASISCRSSKSLLYKDGKTYLNWFLQKPGQSPQLLIYLMSTHASGVPDRFSGSGSG
TDFTLKISRVEAEDVGVYYCQQLVDYPLTFGGGTKLEIKRTVAAPSVFIFPPSDEQLKSGTASVVCLLNNFYP
REAKVQWKVDNALQSGNSQESVTEQDSKDSTYSLSSTLTLSKADYEKHKVYACEVTHQGLSSPVTKSFNR
GEC SEQ ID NO: 25: heavy chain variable region
QVQLVQSGSELKKPGASVKVSCKASGYTFTNYGMNWVRQAPGQGLKWMGWINTNTGEPTYAQEFTG
RFVFSLDTSVSTAYLQISSLKAEDTAVYFCAPYDNFFAYWGQGTTVTVS SEQ ID NO: 26: light chain variable region
DIVLTQSPLSLPVTPGEPASISCRSSKSLLYKDGKTYLNWFLQKPGQSPQLLIYLMSTHASGVPDRFSGSGSG
TDFTLKISRVEAEDVGVYYCQQLVDYPLTFGGGTKLEIK SEQ ID NO: 27: peptide_1, as disclosed in FIG. 11A
ADNFSLHDALSGSGNPNPQG -continued

| INFORMAL SEQUENCE LISTINGS |
|---|

SEQ ID NO: 28: peptide_2, as disclosed in FIG. 11A
SGSGNPNPQGWPGAWGNQPA

SEQ ID NO: 29: peptide_3, as disclosed in FIG. 11A
WPGAWGNQPAGAGGYPGASY

SEQ ID NO: 30: peptide_4, as disclosed in FIG. 11A
GAGGYPGASYPGAYPGQAPP

SEQ ID NO: 31: peptide_7, as disclosed in FIG. 11A
AYPGAPGAYPGAPAPGVYPG

SEQ ID NO: 32: peptide_8, as disclosed in FIG. 11A
GAPAPGVYPGPPSGPGAYPS

SEQ ID NO: 33: peptide_9, as disclosed in FIG. 11A
PPSGPGAYPSSGQPSATGAY

SEQ ID NO: 34: peptide_10, as disclosed in FIG. 11A
SGQPSATGAYPATGPYGAPA

SEQ ID NO: 35: peptide_11, as disclosed in FIG. 11A
PATGPYGAPAGPLIVPYNLP

SEQ ID NO: 36: peptide_12, as disclosed in FIG. 11A
GPLIVPYNLPLPGGVVPRML

SEQ ID NO: 37: peptide_13, as disclosed in FIG. 11A
LPGGVVPRMLITILGTVKPN

SEQ ID NO: 38: peptide_14, as disclosed in FIG. 11A
ITILGTVKPNANRIALDFQR

SEQ ID NO: 39: peptide_15, as disclosed in FIG. 11A
ANRIALDFQRGNDVAFHFNP

SEQ ID NO: 40: peptide_16, as disclosed in FIG. 11A
GNDVAFHFNPRFNENNRRVI

SEQ ID NO: 41: peptide_17, as disclosed in FIG. 11A
RFNENNRRVIVCNTKLDNNW

SEQ ID NO: 42: peptide_18, as disclosed in FIG. 11A
VCNTKLDNNWGREERQSVFP

SEQ ID NO: 43: peptide_19, as disclosed in FIG. 11A
GREERQSVFPFESGKPFKIQ

SEQ ID NO: 44: peptide_20, as disclosed in FIG. 11A
FESGKPFKIQVLVEPDHFKV

SEQ ID NO: 45: peptide_21, as disclosed in FIG. 11A
VLVEPDHFKVAVNDAHLLQY

SEQ ID NO: 46: peptide_22, as disclosed in FIG. 11A
AVNDAHLLQYNHRVKKLNEI

SEQ ID NO: 47: peptide_23, as disclosed in FIG. 11A
NHRVKKLNEISKLGISGDID

SEQ ID NO: 48: peptide_24, as disclosed in FIG. 11A
SKLGISGDIDLTSASYTMI

SEQ ID NO: 49: Pep-1, as disclosed in FIG. 11C
PGAYPGQAPP

SEQ ID NO: 50: Pep-3, as disclosed in FIG. 11C
GAYPGQAPPGA

SEQ ID NO: 51: Pep-4, as disclosed in FIG. 11C
APPGAYPGAP

SEQ ID NO: 52: Pep-5, as disclosed in FIG. 11C
YPGAPGAYP

SEQ ID NO: 53: Pep-6, as disclosed in FIG. 11C
APPGAY

INFORMAL SEQUENCE LISTINGS

SEQ ID NO: 54: Pep-7, as disclosed in FIG. 11C
GAYPGQ

SEQ ID NO: 55: Pep-8, as disclosed in FIG. 11C
PGQAPP

What is claimed is:

1. A method of activating an immune response in a patient with a cancer, comprising:
   administering to the patient an effective amount of an anti-Gal3 antibody that interferes with the interaction between Gal3 and TIM-3, wherein the anti-Gal3 antibody comprises
   (1) a light chain variable region comprising a complementary determining region (CDR) L1, a CDR L2, and a CDR L3 and
   (2) a heavy chain variable region comprising a CDR H1, a CDR H2, and a CDR H3,
   wherein
   the CDR L1 comprises the amino acid sequence of SEQ ID NO:17,
   the CDR L2 comprises the amino acid sequence of SEQ ID NO:18,
   the CDR L3 comprises the amino acid sequence of SEQ ID NO:19,
   the CDR H1 comprises the amino acid sequence of SEQ ID NO:9,
   the CDR H2 comprises the amino acid of SEQ ID NO:10, and
   the CDR H3 comprises the amino acid sequence of SEQ ID NO:11;
   wherein the Gal3 is overexpressed on cells in a tumor microenvironment,
   the TIM-3 is expressed on immune cells, and
   the effective amount is sufficient to activate the immune response in the patient
   wherein the anti-Gal3 antibody is a humanized antibody or a human antibody.

2. The method of claim 1, wherein the interaction between Gal3 and TIM-3 occurs in a tumor microenvironment, and wherein the activation of the immune response decreases the cancer load of the patient.

3. The method of claim 1, wherein the immune cells are T cells or NK cells and activating the immune response is through activating the T cells or NK cells.

4. The method of claim 1, wherein the cancer is a metastatic cancer or a primary cancer.

5. The method of claim 1, wherein the antibody is a single chain antibody or a Fab.

6. The method of claim 1, wherein the anti-Gal3 antibody-is administered intravenously.

7. The method of claim 1, wherein the anti-Gal3 antibody is administered in combination with at least one of a chemotherapy, radiotherapy, or a checkpoint inhibitor therapy.

8. The method of claim 7, wherein the checkpoint inhibitor therapy is an anti-PD-1 therapy or an anti-CTLA-4 therapy.

9. The method of claim 1, wherein the anti-Gal3 antibody-is administered at a dose of between 10 μg to 100 mg per kilogram of body weight of the patient every other week.

10. A method of activating immune response in a patient comprising administering to the patient an anti-Gal3 antibody that interferes with the interaction between Gal3 and TIM-3,
    wherein said anti-Gal3 antibody is administered in an amount sufficient to activate immune response,
    wherein the anti-Gal3 antibody is a humanized antibody; and
    wherein the anti-Gal3 antibody comprises
    (1) a light chain variable region comprising a complementary determining region (CDR) L1, a CDR L2, and a CDR L3 and
    (2) a heavy chain variable region comprising a CDR H1, a CDR H2, and a CDR H3,
    wherein
    the CDR L1 comprises the amino acid sequence of SEQ ID NO:17,
    the CDR L2 comprises the amino acid sequence of SEQ ID NO:18,
    the CDR L3 comprises the amino acid sequence of SEQ ID NO:19,
    the CDR H1 comprises the amino acid sequence of SEQ ID NO:9,
    the CDR H2 comprises the amino acid of SEQ ID NO:10, and
    the CDR H3 comprises the amino acid sequence of SEQ ID NO:11.

11. A method of activating immune response in a patient comprising administering to the patient an antibody, wherein the antibody includes a means for inhibiting the interaction between Gal3 and TIM-3, wherein the means for inhibiting the interaction comprises a light chain variable region comprising a CDR L1, a CDR L2, and a CDR L3, and a heavy chain variable region comprising a CDR H1, a CDR H2, and a CDR H3, wherein the CDR L1 comprises the amino acid sequence of SEQ ID NO:17,
the CDR L2 comprises the amino acid sequence of SEQ ID NO:18,
the CDR L3 comprises the amino acid sequence of SEQ ID NO:19,
the CDR H1 comprises the amino acid sequence of SEQ ID NO:9,
the CDR H2 comprises the amino acid of SEQ ID NO:10, and
the CDR H3 comprises the amino acid sequence of SEQ ID NO:11.

12. The method of claim 10, wherein the heavy chain variable region has a sequence having at least 90% identity to the amino acid sequence of SEQ ID NO: 25.

13. The method of claim 10, wherein the light chain variable region has a sequence having at least 90% identity to the amino acid sequence of SEQ ID NO: 26.

14. The method of claim 1, wherein the heavy chain variable region has a sequence having at least 90% identity to the amino acid sequence of SEQ ID NO: 25.

15. The method of claim 1, wherein the light chain variable region has a sequence having at least 90% identity to the amino acid sequence of SEQ ID NO: 26.

* * * * *

UNITED STATES PATENT AND TRADEMARK OFFICE
CERTIFICATE OF CORRECTION

PATENT NO. : 12,227,567 B2
APPLICATION NO. : 16/633530
DATED : February 18, 2025
INVENTOR(S) : Dongxu Sun et al.

Page 1 of 4

It is certified that error appears in the above-identified patent and that said Letters Patent is hereby corrected as shown below:

On the Title Page

In U.S. Patent Documents, Under Column 2, Page 4, Line 37, delete "Iikow et al." and insert -- Ilkow et al. --.

In Other Publications, Under Column 2, Page 7, Line 59, delete "Chem. Sec. 119" and insert -- Chem. Soc. 119 --.

In Other Publications, Under Column 1, Page 8, Line 3, delete "bioRxiv prepreint doi:" and insert -- bioRxiv preprint doi: --.

In Other Publications, Under Column 1, Page 8, Line 38, delete "bioRxiv prepreint doi:" and insert -- bioRxiv preprint doi: --.

In Other Publications, Under Column 1, Page 8, Line 55, delete "in phabdomyosarcomas: rationale" and insert -- in rhabdomyosarcomas: rationale --.

In Other Publications, Under Column 2, Page 8, Line 15, delete "Shaiaby et" and insert -- Shalaby et --.

In Other Publications, Under Column 2, Page 8, Line 22, delete "muscle ceils, Molecular" and insert -- muscle cells, Molecular --.

In Other Publications, Under Column 2, Page 8, Line 24, delete "enhances initimal translocation" and insert -- enhances intimal translocation --.

In Other Publications, Under Column 2, Page 8, Line 37, delete "oligodendrocyte differention and" and insert -- oligodendrocyte differentiation and --.

Signed and Sealed this
Twenty-ninth Day of April, 2025

Coke Morgan Stewart
*Acting Director of the United States Patent and Trademark Office*

CERTIFICATE OF CORRECTION (continued)
U.S. Pat. No. 12,227,567 B2

In Other Publications, Under Column 2, Page 9, Line 23, delete "with hypofribinolysis and" and insert -- with hypofibrinolysis and --.

In Other Publications, Under Column 2, Page 9, Line 56, delete "and amyioid-β" and insert -- and amyloid-β --.

In Other Publications, Under Column 2, Page 9, Line 64, delete "and immunoaiiergic injury" and insert -- and immunoallergic injury --.

In Other Publications, Under Column 1, Page 10, Line 15, delete "inhibits gaiectin-3" and insert -- inhibits galectin-3 --.

In Other Publications, Under Column 1, Page 10, Line 58, delete "of gelactin-3" and insert -- of galectin-3 --.

In Other Publications, Under Column 2, Page 10, Line 17, delete "microglia-mediated neuroinfiammation and" and insert -- microglia-mediated neuroinflammation and --.

In Other Publications, Under Column 2, Page 10, Line 45, delete "role ofc-reactive" and insert -- role of c-reactive --.

In Other Publications, Under Column 1, Page 11, Line 26, delete "in adenocarcimona liver" and insert -- in adenocarcinoma liver --.

In Other Publications, Under Column 1, Page 11, Line 53, delete "vaginalis lipopohosphoglycan exploits" and insert -- vaginalis lipophosphoglycan exploits --.

In Other Publications, Under Column 1, Page 11, Line 61, delete "Search Reporot dated" and insert -- Search Report dated --.

In Other Publications, Under Column 1, Page 11, Line 65, delete "3 antibody ab2785" and insert -- "3 antibody [A3A12] ab2785, --.

In Other Publications, Under Column 2, Page 11, Line 36, delete "Requstion by" and insert -- Requisition by --.

In Other Publications, Under Column 2, Page 11, Line 40, delete "PCT/US22/073594." and insert -- PCT/US22/073694. --.

In Other Publications, Under Column 2, Page 11, Line 42, delete "reduced xengeneic neutrophil" and insert -- reduced xenogeneic neutrophil --.

In Other Publications, Under Column 2, Page 11, Line 47, delete "combinatorial association, EMBO" and insert -- combinatorial associations, EMBO --.

CERTIFICATE OF CORRECTION (continued)
U.S. Pat. No. 12,227,567 B2

In Other Publications, Under Column 2, Page 11, Line 64, delete "of Immunlogy, 45" and insert -- of Immunology, 45 --.

In the Specification

Under Column 1, Line 18, delete "entitled SeqListingIMMUTOO2NP.TXT" and insert -- entitled SeqListingIMMUT002NP.TXT --.

Under Column 4, Line 3, delete "that hGal3, but" and insert -- that hGal3, but --.

Under Column 6, Line 54, delete "i.e., an a carbon" and insert -- i.e., an α carbon --.

Under Column 9, Line 13 (approx.), delete "FR4. framework region" and insert -- FR4. Framework region --.

Under Column 12, Line 18, delete ".beta.- glactosidase)" and insert -- beta-galactosidase) --.

Under Column 13, Line 12, delete "lung cancer" and insert -- lung cancer. --.

Under Column 16, Line 43, delete "The cominatorial libraries" and insert -- The combinatorial libraries --.

Under Column 17, Line 47, delete "(Biacore A B, Uppsala" and insert -- (Biacore AB, Uppsala, --.

Under Column 19, Line 50, delete "the genentic marker" and insert -- the genetic marker --.

Under Column 22, Line 22, delete "and mechloroethamine hydrochloride," and insert -- and mechlorethamine hydrochloride, --.

Under Column 22, Line 42, delete "Fluorouracil, Foxuridine, Cytarabine," and insert -- Fluorouracil, Floxuridine, Cytarabine, --.

Under Column 22, Line 50, delete "Daunorubicin (dauorubicin hydrochloride," and insert -- Daunorubicin (daunorubicin hydrochloride, --.

Under Column 23, Line 25, delete "1-(phenylmethy)ethyl]" and insert -- 1-(phenylmethyl)ethyl] --.

Under Column 23, Line 37, delete "NPC, campothecin, topotecan," and insert -- NPC, camptothecin, topotecan, --.

Under Column 24, Line 56, delete "and titatium dioxide." and insert -- and titanium dioxide. --.

Under Column 33, Line 6, delete "(R&D sytems), mAb" and insert -- (R&D systems), mAb --.

Under Column 35, Line 62, delete "mean±SEM, The" and insert -- mean±SEM. The --.

CERTIFICATE OF CORRECTION (continued)
U.S. Pat. No. 12,227,567 B2

Under Column 37, Lines 60-61, delete "from perpheral blood" and insert -- from peripheral blood --.

In the Claims

Under Column 74, Claim 6, Lines 29-30, delete "Gal3 antibody-is administered" and insert -- Gal3 antibody is administered --.

Under Column 74, Claim 9, Lines 38-39, delete "Gal3 antibody-is administered" and insert -- Gal3 antibody is administered --.

SEQUENCE LISTING

<160> NUMBER OF SEQ ID NOS: 55

<210> SEQ ID NO 1
<211> LENGTH: 1406
<212> TYPE: DNA
<213> ORGANISM: Mus musculus

<400> SEQUENCE: 1

```
gggagggcgg gcccggggaa aagagtacta gaagcggccg agccaccgcc cagctctgac      60
agctagcgga gcggcgggtg gagcactaat caggtgagcg gcacagagag cactacccag     120
gaaaatggca gacagctttt cgcttaacga tgccttagct ggctctggaa acccaaaccc     180
tcaaggatat ccgggtgcat gggggaacca gcctggggca gggggctacc caggggctgc     240
ttatcctggg gcctacccag acaagctcc tccaggggcc tacccaggac aggctcctcc     300
aggggcctac ccaggacagg ctcctcctag tgcctacccc ggcccaactg cccctggagc     360
ttatcctggc ccaactgccc ctggagctta tcctggctca actgcccctg gagccttccc     420
agggcaacct ggggcacctg ggcctaccc cagtgctcct ggaggctatc ctgctgctgg     480
cccttatggt gtccccgctg gaccactgac ggtgccctat gacctgccct gcctggagg     540
agtcatgccc cgcatgctga tcacaatcat gggcacagtg aaacccaacg caaacaggat     600
tgttctagat tcaggagag ggaatgatgt tgccttccac tttaaccccc gcttcaatga     660
gaacaacagg agagtcattg tgtgtaacac gaagcaggac aataactggg gaaaggaaga     720
aagacagtca gccttcccct tgagagtgg caaaccattc aaaatacaag tcctggttga     780
agctgaccac ttcaaggttg cggtcaacga tgctcaccta ctgcagtaca accatcggat     840
gaagaacctc cgggaaatca gccaactggg gatcagtggt gacataaccc tcaccagcgc     900
taaccacgcc atgatctaag ccagaagggg cggcaccgaa accggccctg tgtgccttag     960
gagtgggaaa ctttgcattt ctctctcctt atccttcttg taagacatcc atttaataaa    1020
gtctcatgct gagagatacc catcgctttg ggggttttta tgatactgga tgtcaaatct    1080
taggactgct cgtgactgct aggcaagtgt tctctcactg agctacacat ccctagcctt    1140
ttaaactttg tgtgttgtgt gtctgtgcac atgggtacag gtgcctgctc acttgagagg    1200
caccaggcct cctggagctg gagttacagg tggttgtaag taagctgtgt gaccaggttg    1260
ctgggaacca gtctcagatc ctcctgagac aggtcaggtc cactgatgcc tccagctgcc    1320
tgtctttata tgcccttga tttggtgcag ttttatataa agggaactat gtaattatca    1380
ataaaccatc ctgatttta caaagg                                          1406
```

<210> SEQ ID NO 2
<211> LENGTH: 264
<212> TYPE: PRT
<213> ORGANISM: Mus musculus

<400> SEQUENCE: 2

```
Met Ala Asp Ser Phe Ser Leu Asn Asp Ala Leu Ala Gly Ser Gly Asn
1               5                   10                  15

Pro Asn Pro Gln Gly Tyr Pro Gly Ala Trp Gly Asn Gln Pro Gly Ala
            20                  25                  30

Gly Gly Tyr Pro Gly Ala Ala Tyr Pro Gly Ala Tyr Pro Gly Gln Ala
        35                  40                  45

Pro Pro Gly Ala Tyr Pro Gly Gln Ala Pro Pro Gly Ala Tyr Pro Gly
    50                  55                  60

Gln Ala Pro Pro Ser Ala Tyr Pro Gly Pro Thr Ala Pro Gly Ala Tyr
65                  70                  75                  80

Pro Gly Pro Thr Ala Pro Gly Ala Tyr Pro Gly Ser Thr Ala Pro Gly
                85                  90                  95

Ala Phe Pro Gly Gln Pro Gly Ala Pro Gly Ala Tyr Pro Ser Ala Pro
            100                 105                 110

Gly Gly Tyr Pro Ala Ala Gly Pro Tyr Gly Val Pro Ala Gly Pro Leu
            115                 120                 125

Thr Val Pro Tyr Asp Leu Pro Leu Pro Gly Gly Val Met Pro Arg Met
130                 135                 140

Leu Ile Thr Ile Met Gly Thr Val Lys Pro Asn Ala Asn Arg Ile Val
145                 150                 155                 160

Leu Asp Phe Arg Arg Gly Asn Asp Val Ala Phe His Phe Asn Pro Arg
                165                 170                 175

Phe Asn Glu Asn Asn Arg Arg Val Ile Val Cys Asn Thr Lys Gln Asp
            180                 185                 190

Asn Asn Trp Gly Lys Glu Glu Arg Gln Ser Ala Phe Pro Phe Glu Ser
            195                 200                 205

Gly Lys Pro Phe Lys Ile Gln Val Leu Val Glu Ala Asp His Phe Lys
210                 215                 220

Val Ala Val Asn Asp Ala His Leu Leu Gln Tyr Asn His Arg Met Lys
225                 230                 235                 240

Asn Leu Arg Glu Ile Ser Gln Leu Gly Ile Ser Gly Asp Ile Thr Leu
                245                 250                 255

Thr Ser Ala Asn His Ala Met Ile
            260

<210> SEQ ID NO 3
<211> LENGTH: 1017
<212> TYPE: DNA
<213> ORGANISM: Homo sapiens

<400> SEQUENCE: 3
gagtatttga ggctcggagc caccgccccg ccggcgcccg cagcacctcc tcgccagcag    60
ccgtccggag ccagccaacg agcggaaaat ggcagacaat ttttcgctcc atgatgcgtt   120
atctgggtct ggaaacccaa accctcaagg atggcctggc gcatggggga accagcctgc   180
tggggcaggg ggctacccag gggcttccta tcctggggcc tacccggcc aggcaccccc    240 agggcttat cctggacagg cacctccagg cgcctaccct ggagcacctg gagcttatcc    300
cggagcacct gcacctggag tctacccagg gccaccagc ggccctgggg cctacccatc    360
ttctggacag ccaagtgcca ccggagccta ccctgccact ggcccctatg gcgcccctgc    420
tgggccactg attgtgcctt ataacctgcc tttgcctggg ggtggtgc ctcgcatgct     480 gataacaatt ctgggcacgg tgaagcccaa tgcaaacaga attgctttag atttccaaag   540
agggaatgat gttgccttcc actttaaccc acgcttcaat gagaacaaca ggagagtcat   600
```

```
tgtttgcaat acaaagctgg ataataactg gggaagggaa gaaagacagt cggttttccc      660
atttgaaagt gggaaaccat tcaaaataca agtactggtt gaacctgacc acttcaaggt      720
tgcagtgaat gatgctcact tgttgcagta caatcatcgg gttaaaaaac tcaatgaaat      780
cagcaaactg ggaattttctg tgacataga cctcaccagt gcttcatata ccatgatata      840
atctgaaagg ggcagattaa aaaaaaaaaa agaatctaaa ccttacatgt gtaaaggttt      900
catgttcact gtgagtgaaa atttttacat tcatcaatat ccctcttgta agtcatctac      960
ttaataaata ttacagtgaa ttacctgtct caatatgtca aaaaaaaaaa aaaaaaa       1017
```

<210> SEQ ID NO 4
<211> LENGTH: 250
<212> TYPE: PRT
<213> ORGANISM: Homo sapiens

<400> SEQUENCE: 4

```
Met Ala Asp Asn Phe Ser Leu His Asp Ala Leu Ser Gly Ser Gly Asn
1               5                   10                  15

Pro Asn Pro Gln Gly Trp Pro Gly Ala Trp Gly Asn Gln Pro Ala Gly
            20                  25                  30

Ala Gly Gly Tyr Pro Gly Ala Ser Tyr Pro Gly Ala Tyr Pro Gly Gln
        35                  40                  45

Ala Pro Pro Gly Ala Tyr Pro Gly Gln Ala Pro Pro Gly Ala Tyr Pro
    50                  55                  60

Gly Ala Pro Gly Ala Tyr Pro Gly Ala Pro Ala Pro Gly Val Tyr Pro
65                  70                  75                  80

Gly Pro Pro Ser Gly Pro Gly Ala Tyr Pro Ser Ser Gly Gln Pro Ser
                85                  90                  95

Ala Thr Gly Ala Tyr Pro Ala Thr Gly Pro Tyr Gly Ala Pro Ala Gly
            100                 105                 110

Pro Leu Ile Val Pro Tyr Asn Leu Pro Leu Pro Gly Gly Val Val Pro
        115                 120                 125

Arg Met Leu Ile Thr Ile Leu Gly Thr Val Lys Pro Asn Ala Asn Arg
130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Glu Arg Gln Ser Val Phe Pro Phe
            180                 185                 190

Glu Ser Gly Lys Pro Phe Lys Ile Gln Val Leu Val Glu Pro Asp His
        195                 200                 205

Phe Lys Val Ala Val Asn Asp Ala His Leu Leu Gln Tyr Asn His Arg
    210                 215                 220

Val Lys Lys Leu Asn Glu Ile Ser Lys Leu Gly Ile Ser Gly Asp Ile
225                 230                 235                 240

Asp Leu Thr Ser Ala Ser Tyr Thr Met Ile
                245                 250
```

<210> SEQ ID NO 5
<211> LENGTH: 21
<212> TYPE: PRT
<213> ORGANISM: Homo sapiens

<400> SEQUENCE: 5

```
Ala Pro Gly Ala Tyr Pro Gly Gln Ala Pro Gly Ala Tyr Pro Gly
1               5                   10                  15

Gln Ala Pro Pro Gly
            20

<210> SEQ ID NO 6
<211> LENGTH: 21
<212> TYPE: PRT
<213> ORGANISM: Homo sapiens

<400> SEQUENCE: 6

Ala Gly Ala Tyr Pro Gly Gln Ala Pro Pro Gly Ala Tyr Pro Gly Ala
1               5                   10                  15

Pro Gly Ala Tyr Pro
            20

<210> SEQ ID NO 7
<211> LENGTH: 30
<212> TYPE: PRT
<213> ORGANISM: Homo sapiens

<400> SEQUENCE: 7

Pro Gly Ala Tyr Pro Gly Gln Ala Pro Pro Gly Ala Tyr Pro Gly Gln
1               5                   10                  15

Ala Pro Pro Gly Ala Tyr Pro Gly Ala Pro Gly Ala Tyr Pro
            20                  25                  30

<210> SEQ ID NO 8
<211> LENGTH: 10
<212> TYPE: PRT
<213> ORGANISM: Homo sapiens

<400> SEQUENCE: 8

Gly Gln Ala Pro Pro Gly Ala Tyr Pro Gly
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic construct

<400> SEQUENCE: 9

Gly Tyr Thr Phe Thr Asn Tyr
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic construct

<400> SEQUENCE: 10

Asn Thr Asn Thr Gly Glu
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic construct
```

```
<400> SEQUENCE: 11

Tyr Asp Asn Phe Phe Ala Tyr
1               5

<210> SEQ ID NO 12
<211> LENGTH: 25
<212> TYPE: PRT
<213> ORGANISM: Artificial Sequence
<220> FEATURE:
<223> OTHER INFORMATION: Synthetic construct

<400> SEQUENCE: 12

Gln Val Gln Leu Val Gln Ser Gly Ser Glu Leu Lys Lys Pro Gly Ala
1               5                   10                  15

Ser Val Lys Val Ser Cys Lys Ala Ser
            20                  25

<210> SEQ ID NO 13
<211> LENGTH: 19
<212> TYPE: PRT
<213> ORGANISM: Artificial Sequence
<220> FEATURE:
<223> OTHER INFORMATION: Synthetic construct

<400> SEQUENCE: 13

Gly Met Asn Trp Val Arg Gln Ala Pro Gly Gln Gly Leu Lys Trp Met
1               5                   10                  15

Gly Trp Ile

<210> SEQ ID NO 14
<211> LENGTH: 41
<212> TYPE: PRT
<213> ORGANISM: Artificial Sequence
<220> FEATURE:
<223> OTHER INFORMATION: Synthetic construct

<400> SEQUENCE: 14

Pro Thr Tyr Ala Gln Glu Phe Thr Gly Arg Phe Val Phe Ser Leu Asp
1               5                   10                  15

Thr Ser Val Ser Thr Ala Tyr Leu Gln Ile Ser Ser Leu Lys Ala Glu
            20                  25                  30

Asp Thr Ala Val Tyr Phe Cys Ala Pro
        35                  40

<210> SEQ ID NO 15
<211> LENGTH: 10
<212> TYPE: PRT
<213> ORGANISM: Artificial Sequence
<220> FEATURE:
<223> OTHER INFORMATION: Synthetic construct

<400> SEQUENCE: 15

Trp Gly Gln Gly Thr Thr Val Thr Val Ser
1               5                   10

<210> SEQ ID NO 16
<211> LENGTH: 442
<212> TYPE: PRT
<213> ORGANISM: Artificial Sequence
<220> FEATURE:
<223> OTHER INFORMATION: Synthetic construct

<400> SEQUENCE: 16

Gln Val Gln Leu Val Gln Ser Gly Ser Glu Leu Lys Lys Pro Gly Ala
```

-continued

```
1               5                   10                  15
Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
            35                  40                  45

Gly Trp Ile Asn Thr Asn Thr Gly Glu Pro Thr Tyr Ala Gln Glu Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Pro Tyr Asp Asn Phe Phe Ala Tyr Trp Gly Gln Gly Thr Thr Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Pro
210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430
```

```
Thr Gln Lys Ser Leu Ser Leu Ser Leu Gly
        435                 440

<210> SEQ ID NO 17
<211> LENGTH: 16
<212> TYPE: PRT
<213> ORGANISM: Artificial Sequence
<220> FEATURE:
<223> OTHER INFORMATION: Synthetic construct

<400> SEQUENCE: 17

Arg Ser Ser Lys Ser Leu Leu Tyr Lys Asp Gly Lys Thr Tyr Leu Asn
1               5                   10                  15

<210> SEQ ID NO 18
<211> LENGTH: 7
<212> TYPE: PRT
<213> ORGANISM: Artificial Sequence
<220> FEATURE:
<223> OTHER INFORMATION: Synthetic construct

<400> SEQUENCE: 18

Leu Met Ser Thr His Ala Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic construct

<400> SEQUENCE: 19

Gln Gln Leu Val Asp Tyr Pro Leu Thr
1               5

<210> SEQ ID NO 20
<211> LENGTH: 23
<212> TYPE: PRT
<213> ORGANISM: Artificial Sequence
<220> FEATURE:
<223> OTHER INFORMATION: Synthetic construct

<400> SEQUENCE: 20

Asp Ile Val Leu Thr Gln Ser Pro Leu Ser Leu Pro Val Thr Pro Gly
1               5                   10                  15

Glu Pro Ala Ser Ile Ser Cys
            20

<210> SEQ ID NO 21
<211> LENGTH: 15
<212> TYPE: PRT
<213> ORGANISM: Artificial Sequence
<220> FEATURE:
<223> OTHER INFORMATION: Synthetic construct

<400> SEQUENCE: 21

Trp Phe Leu Gln Lys Pro Gly Gln Ser Pro Gln Leu Leu Ile Tyr
1               5                   10                  15

<210> SEQ ID NO 22
<211> LENGTH: 32
<212> TYPE: PRT
<213> ORGANISM: Artificial Sequence
<220> FEATURE:
<223> OTHER INFORMATION: Synthetic construct
```

<400> SEQUENCE: 22

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 23
<211> LENGTH: 10
<212> TYPE: PRT
<213> ORGANISM: Artificial Sequence
<220> FEATURE:
<223> OTHER INFORMATION: Synthetic construct

<400> SEQUENCE: 23

Phe Gly Gly Gly Thr Lys Leu Glu Ile Lys
1               5                   10

<210> SEQ ID NO 24
<211> LENGTH: 219
<212> TYPE: PRT
<213> ORGANISM: Artificial Sequence
<220> FEATURE:
<223> OTHER INFORMATION: Synthetic construct

<400> SEQUENCE: 24

Asp Ile Val Leu Thr Gln Ser Pro Leu Ser Leu Pro Val Thr Pro Gly
1               5                   10                  15

Glu Pro Ala Ser Ile Ser Cys Arg Ser Ser Lys Ser Leu Leu Tyr Lys
            20                  25                  30

Asp Gly Lys Thr Tyr Leu Asn Trp Phe Leu Gln Lys Pro Gly Gln Ser
        35                  40                  45

Pro Gln Leu Leu Ile Tyr Leu Met Ser Thr His Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Leu
                85                  90                  95

Val Asp Tyr Pro Leu Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 25
<211> LENGTH: 115
<212> TYPE: PRT
<213> ORGANISM: Artificial Sequence

```
<220> FEATURE:
<223> OTHER INFORMATION: Synthetic construct

<400> SEQUENCE: 25

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Asn Thr Gly Glu Pro Thr Tyr Ala Gln Glu Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Pro Tyr Asp Asn Phe Phe Ala Tyr Trp Gly Gln Gly Thr Thr Val
            100                 105                 110

Thr Val Ser
        115

<210> SEQ ID NO 26
<211> LENGTH: 112
<212> TYPE: PRT
<213> ORGANISM: Artificial Sequence
<220> FEATURE:
<223> OTHER INFORMATION: Synthetic construct

<400> SEQUENCE: 26

Asp Ile Val Leu Thr Gln Ser Pro Leu Ser Leu Pro Val Thr Pro Gly
1               5                   10                  15

Glu Pro Ala Ser Ile Ser Cys Arg Ser Ser Lys Ser Leu Leu Tyr Lys
            20                  25                  30

Asp Gly Lys Thr Tyr Leu Asn Trp Phe Leu Gln Lys Pro Gly Gln Ser
        35                  40                  45

Pro Gln Leu Leu Ile Tyr Leu Met Ser Thr His Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Leu
                85                  90                  95

Val Asp Tyr Pro Leu Thr Phe Gly Gly Gly Thr Lys Leu Glu Ile Lys
            100                 105                 110

<210> SEQ ID NO 27
<211> LENGTH: 20
<212> TYPE: PRT
<213> ORGANISM: Artificial Sequence
<220> FEATURE:
<223> OTHER INFORMATION: Synthetic construct

<400> SEQUENCE: 27

Ala Asp Asn Phe Ser Leu His Asp Ala Leu Ser Gly Ser Gly Asn Pro
1               5                   10                  15

Asn Pro Gln Gly
            20

<210> SEQ ID NO 28
<211> LENGTH: 20
```

```
<212> TYPE: PRT
<213> ORGANISM: Artificial Sequence
<220> FEATURE:
<223> OTHER INFORMATION: Synthetic construct

<400> SEQUENCE: 28

Ser Gly Ser Gly Asn Pro Asn Pro Gln Gly Trp Pro Gly Ala Trp Gly
1               5                   10                  15

Asn Gln Pro Ala
            20

<210> SEQ ID NO 29
<211> LENGTH: 20
<212> TYPE: PRT
<213> ORGANISM: Artificial Sequence
<220> FEATURE:
<223> OTHER INFORMATION: Synthetic construct

<400> SEQUENCE: 29

Trp Pro Gly Ala Trp Gly Asn Gln Pro Ala Gly Ala Gly Gly Tyr Pro
1               5                   10                  15

Gly Ala Ser Tyr
            20

<210> SEQ ID NO 30
<211> LENGTH: 20
<212> TYPE: PRT
<213> ORGANISM: Artificial Sequence
<220> FEATURE:
<223> OTHER INFORMATION: Synthetic construct

<400> SEQUENCE: 30

Gly Ala Gly Gly Tyr Pro Gly Ala Ser Tyr Pro Gly Ala Tyr Pro Gly
1               5                   10                  15

Gln Ala Pro Pro
            20

<210> SEQ ID NO 31
<211> LENGTH: 20
<212> TYPE: PRT
<213> ORGANISM: Artificial Sequence
<220> FEATURE:
<223> OTHER INFORMATION: Synthetic construct

<400> SEQUENCE: 31

Ala Tyr Pro Gly Ala Pro Gly Ala Tyr Pro Gly Ala Pro Ala Pro Gly
1               5                   10                  15

Val Tyr Pro Gly
            20

<210> SEQ ID NO 32
<211> LENGTH: 20
<212> TYPE: PRT
<213> ORGANISM: Artificial Sequence
<220> FEATURE:
<223> OTHER INFORMATION: Synthetic construct

<400> SEQUENCE: 32

Gly Ala Pro Ala Pro Gly Val Tyr Pro Gly Pro Pro Ser Gly Pro Gly
1               5                   10                  15

Ala Tyr Pro Ser
            20

<210> SEQ ID NO 33
```

<211> LENGTH: 20
<212> TYPE: PRT
<213> ORGANISM: Artificial Sequence
<220> FEATURE:
<223> OTHER INFORMATION: Synthetic construct

<400> SEQUENCE: 33

Pro Pro Ser Gly Pro Gly Ala Tyr Pro Ser Ser Gly Gln Pro Ser Ala
1               5                   10                  15

Thr Gly Ala Tyr
            20

<210> SEQ ID NO 34
<211> LENGTH: 20
<212> TYPE: PRT
<213> ORGANISM: Artificial Sequence
<220> FEATURE:
<223> OTHER INFORMATION: Synthetic construct

<400> SEQUENCE: 34

Ser Gly Gln Pro Ser Ala Thr Gly Ala Tyr Pro Ala Thr Gly Pro Tyr
1               5                   10                  15

Gly Ala Pro Ala
            20

<210> SEQ ID NO 35
<211> LENGTH: 20
<212> TYPE: PRT
<213> ORGANISM: Artificial Sequence
<220> FEATURE:
<223> OTHER INFORMATION: Synthetic construct

<400> SEQUENCE: 35

Pro Ala Thr Gly Pro Tyr Gly Ala Pro Ala Gly Pro Leu Ile Val Pro
1               5                   10                  15

Tyr Asn Leu Pro
            20

<210> SEQ ID NO 36
<211> LENGTH: 20
<212> TYPE: PRT
<213> ORGANISM: Artificial Sequence
<220> FEATURE:
<223> OTHER INFORMATION: Synthetic construct

<400> SEQUENCE: 36

Gly Pro Leu Ile Val Pro Tyr Asn Leu Pro Leu Pro Gly Gly Val Val
1               5                   10                  15

Pro Arg Met Leu
            20

<210> SEQ ID NO 37
<211> LENGTH: 20
<212> TYPE: PRT
<213> ORGANISM: Artificial Sequence
<220> FEATURE:
<223> OTHER INFORMATION: Synthetic construct

<400> SEQUENCE: 37

Leu Pro Gly Gly Val Val Pro Arg Met Leu Ile Thr Ile Leu Gly Thr
1               5                   10                  15

Val Lys Pro Asn
            20

<210> SEQ ID NO 38
<211> LENGTH: 20
<212> TYPE: PRT
<213> ORGANISM: Artificial Sequence
<220> FEATURE:
<223> OTHER INFORMATION: Synthetic construct

<400> SEQUENCE: 38

```
Ile Thr Ile Leu Gly Thr Val Lys Pro Asn Ala Asn Arg Ile Ala Leu
1               5                   10                  15
Asp Phe Gln Arg
            20
```

<210> SEQ ID NO 39
<211> LENGTH: 20
<212> TYPE: PRT
<213> ORGANISM: Artificial Sequence
<220> FEATURE:
<223> OTHER INFORMATION: Synthetic construct

<400> SEQUENCE: 39

```
Ala Asn Arg Ile Ala Leu Asp Phe Gln Arg Gly Asn Asp Val Ala Phe
1               5                   10                  15
His Phe Asn Pro
            20
```

<210> SEQ ID NO 40
<211> LENGTH: 20
<212> TYPE: PRT
<213> ORGANISM: Artificial Sequence
<220> FEATURE:
<223> OTHER INFORMATION: Synthetic construct

<400> SEQUENCE: 40

```
Gly Asn Asp Val Ala Phe His Phe Asn Pro Arg Phe Asn Glu Asn Asn
1               5                   10                  15
Arg Arg Val Ile
            20
```

<210> SEQ ID NO 41
<211> LENGTH: 20
<212> TYPE: PRT
<213> ORGANISM: Artificial Sequence
<220> FEATURE:
<223> OTHER INFORMATION: Synthetic construct

<400> SEQUENCE: 41

```
Arg Phe Asn Glu Asn Asn Arg Arg Val Ile Val Cys Asn Thr Lys Leu
1               5                   10                  15
Asp Asn Asn Trp
            20
```

<210> SEQ ID NO 42
<211> LENGTH: 20
<212> TYPE: PRT
<213> ORGANISM: Artificial Sequence
<220> FEATURE:
<223> OTHER INFORMATION: Synthetic construct

<400> SEQUENCE: 42

```
Val Cys Asn Thr Lys Leu Asp Asn Asn Trp Gly Arg Glu Glu Arg Gln
1               5                   10                  15
Ser Val Phe Pro
            20
```

<210> SEQ ID NO 43
<211> LENGTH: 20
<212> TYPE: PRT
<213> ORGANISM: Artificial Sequence
<220> FEATURE:
<223> OTHER INFORMATION: Synthetic construct

<400> SEQUENCE: 43

Gly Arg Glu Glu Arg Gln Ser Val Phe Pro Phe Glu Ser Gly Lys Pro
1               5                   10                  15

Phe Lys Ile Gln
            20

<210> SEQ ID NO 44
<211> LENGTH: 20
<212> TYPE: PRT
<213> ORGANISM: Artificial Sequence
<220> FEATURE:
<223> OTHER INFORMATION: Synthetic construct

<400> SEQUENCE: 44

Phe Glu Ser Gly Lys Pro Phe Lys Ile Gln Val Leu Val Glu Pro Asp
1               5                   10                  15

His Phe Lys Val
            20

<210> SEQ ID NO 45
<211> LENGTH: 20
<212> TYPE: PRT
<213> ORGANISM: Artificial Sequence
<220> FEATURE:
<223> OTHER INFORMATION: Synthetic construct

<400> SEQUENCE: 45

Val Leu Val Glu Pro Asp His Phe Lys Val Ala Val Asn Asp Ala His
1               5                   10                  15

Leu Leu Gln Tyr
            20

<210> SEQ ID NO 46
<211> LENGTH: 20
<212> TYPE: PRT
<213> ORGANISM: Artificial Sequence
<220> FEATURE:
<223> OTHER INFORMATION: Synthetic construct

<400> SEQUENCE: 46

Ala Val Asn Asp Ala His Leu Leu Gln Tyr Asn His Arg Val Lys Lys
1               5                   10                  15

Leu Asn Glu Ile
            20

<210> SEQ ID NO 47
<211> LENGTH: 20
<212> TYPE: PRT
<213> ORGANISM: Artificial Sequence
<220> FEATURE:
<223> OTHER INFORMATION: Synthetic construct

<400> SEQUENCE: 47

Asn His Arg Val Lys Lys Leu Asn Glu Ile Ser Lys Leu Gly Ile Ser
1               5                   10                  15

Gly Asp Ile Asp
            20

```
<210> SEQ ID NO 48
<211> LENGTH: 19
<212> TYPE: PRT
<213> ORGANISM: Artificial Sequence
<220> FEATURE:
<223> OTHER INFORMATION: Synthetic construct

<400> SEQUENCE: 48

Ser Lys Leu Gly Ile Ser Gly Asp Ile Asp Leu Thr Ser Ala Ser Tyr
1               5                   10                  15

Thr Met Ile

<210> SEQ ID NO 49
<211> LENGTH: 10
<212> TYPE: PRT
<213> ORGANISM: Artificial Sequence
<220> FEATURE:
<223> OTHER INFORMATION: Synthetic construct

<400> SEQUENCE: 49

Pro Gly Ala Tyr Pro Gly Gln Ala Pro Pro
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic construct

<400> SEQUENCE: 50

Gly Ala Tyr Pro Gly Gln Ala Pro Pro Gly Ala
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic construct

<400> SEQUENCE: 51

Ala Pro Pro Gly Ala Tyr Pro Gly Ala Pro
1               5                   10

<210> SEQ ID NO 52
<211> LENGTH: 9
<212> TYPE: PRT
<213> ORGANISM: Artificial Sequence
<220> FEATURE:
<223> OTHER INFORMATION: Synthetic construct

<400> SEQUENCE: 52

Tyr Pro Gly Ala Pro Gly Ala Tyr Pro
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic construct

<400> SEQUENCE: 53

Ala Pro Pro Gly Ala Tyr
```

```
<210> SEQ ID NO 54
<211> LENGTH: 6
<212> TYPE: PRT
<213> ORGANISM: Artificial Sequence
<220> FEATURE:
<223> OTHER INFORMATION: Synthetic construct

<400> SEQUENCE: 54

Gly Ala Tyr Pro Gly Gln
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic construct

<400> SEQUENCE: 55

Pro Gly Gln Ala Pro Pro
1               5
```